United States Patent [19]

Ondetti et al.

[11] 4,316,906
[45] Feb. 23, 1982

[54] MERCAPTOACYL DERIVATIVES OF SUBSTITUTED PROLINES

[75] Inventors: Miguel A. Ondetti, Princeton; John Krapcho, Somerset, both of N.J.

[73] Assignee: E. R. Squibb & Sons, Inc., Princeton, N.J.

[21] Appl. No.: 202,801

[22] Filed: Oct. 31, 1980

Related U.S. Application Data

[63] Continuation-in-part of Ser. No. 126,239, Mar. 3, 1980, abandoned, which is a continuation-in-part of Ser. No. 52,691, Jul. 2, 1979, abandoned, which is a continuation-in-part of Ser. No. 932,883, Aug. 11, 1978, abandoned.

[51] Int. Cl.$^3$ .................... A61K 31/40; C07D 207/12
[52] U.S. Cl. .................. 424/274; 260/326.2; 260/326.43; 260/326.47; 260/326.25; 260/326.22; 424/240; 424/246; 424/250; 424/251
[58] Field of Search ........... 260/326.2, 326.43, 326.25, 260/326.22, 326.47; 424/274

[56] References Cited

U.S. PATENT DOCUMENTS

| | | | |
|---|---|---|---|
| 4,046,889 | 9/1977 | Ondetti et al. | 260/326.2 |
| 4,105,776 | 8/1978 | Ondetti et al. | 424/274 |
| 4,154,935 | 5/1979 | Ondetti et al. | 546/189 |

OTHER PUBLICATIONS

Neuberger, "The Stereochemistry of Hydroxyprolines", J. Chem. Soc., (1945) pp. 429–432.
Patchett, et al., "Studies on Hydroxyproline", J. Amer. Chem. Soc., vol. 79, pp. 185–192 (1957).
Baer, "Derivatives of Hydroxy-L-Proline," Can. J. Biochem. Physiol., vol. 37, pp. 583–587 (1959).
Sheehan et al., "The Synthesis of cis and trans 3-Hydroxy-L Proline," J. Amer. Chem. Soc., vol. 85, p. 3863, 1963.
Magerlein, "Lincomycin VII . . . ", J. Med. Chem., vol. 10, pp. 1161–1163, (1967).
Mauger, et al., "Analogs and Homologs of Proline and Hydroxyproline", Chem. Rev., vol. 66, pp. 47–86, 1966.

*Primary Examiner*—Jane T. Fan
*Attorney, Agent, or Firm*—Lawrence S. Levinson; Stephen B. Davis

[57] ABSTRACT

New mercaptoacyl derivatives of substituted prolines which have the general formula

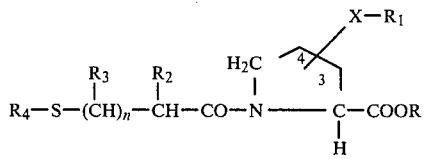

are useful as hypotensive agents.

61 Claims, No Drawings

1

MERCAPTOACYL DERIVATIVES OF SUBSTITUTED PROLINES

RELATED APPLICATIONS

This application is a continuation-in-part of application Ser. No. 126,239 filed Mar. 3, 1980 now abandoned, which is a continuation-in-part of application Ser. No. 52,691 filed July 2, 1979, now abandoned, which is a continuation-in-part of application Ser. No. 932,883, filed Aug. 11, 1978, now abandoned.

BACKGROUND OF THE INVENTION

U.S. Pat. No. 4,105,776, issued Aug. 8, 1978 to Miguel Angel Ondetti and David W. Cushman, and its parent U.S. Pat. No. 4,046,889, issued Sept. 6, 1977, disclose certain mercaptoacyl derivatives of the naturally occurring amino acids proline and hydroxyproline. These compounds are angiotensin converting enzyme inhibitors which can be used for the reduction of blood pressure.

Ondetti et al. in U.S. Pat. No. 4,154,935 and in application Ser. No. 37,255, filed May 9, 1979, disclose certain mercaptoacyl derivatives of pipecolic acid and proline wherein the hetero ring can have one or more halogen substituents and the mercaptoacyl sidechain can have a halogen, alkyl, or trifluoromethyl substituent. These compounds are also angiotensin converting enzyme inhibitors which can be used for the reduction of blood pressure.

SUMMARY OF THE INVENTION

This invention relates to new ether and thioether mercaptoacyl prolines of the formula

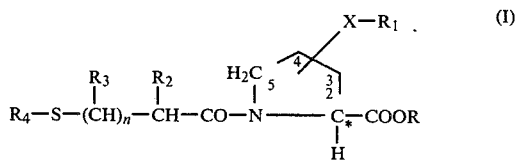

wherein the group X—$R_1$ is located at the 3- or 4-position in the ring;

X is oxygen or sulfur;

R is hydrogen or lower alkyl;

$R_1$ is lower alkyl, lower alkenyl, lower alkynyl, cycloalkyl, 1- or 2-adamantyl, aryl, substituted aryl, phenyl-lower alkylene or substituted phenyl-lower alkylene.

$R_2$ and $R_3$ are independently selected from hydrogen, lower alkyl, and trifluoromethyl;

$R_4$ is hydrogen, $R_5$—CO— or

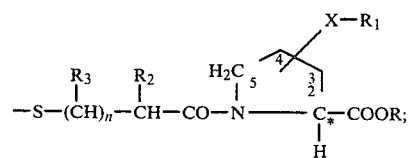

$R_5$ is lower alkyl, phenyl, phenyl-lower alkylene; substituted phenyl, or substituted phenyl-lower alkylene;

n is 0, 1 or 2; and salts thereof.

DETAILED DESCRIPTION OF THE INVENTION

The invention in its broadest aspects relates to the ether and thioether mercaptoacyl prolines having formula I above, to compositions containing such compounds and to the method for using such compounds as anti-hypertensive agents.

The term lower alkyl as used in defining the symbols R, $R_1$, $R_2$ and $R_3$ are straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl being most preferred.

The term lower alkenyl as used in defining the symbol $R_1$ are mono-unsaturated straight or branched chain hydrocarbon groups of from 2 to 7 carbons such as ethenyl, propenyl, isopropenyl, butenyl, and the like. The lower alkynyl groups are straight or branched chain hydrocarbon groups of from 2 to 7 carbons having one triple bond, e.g., propargyl. The preferred lower alkenyl groups are from 2 to 5 carbons and the preferred lower alkynyl groups are from 3 to 4 carbon atoms.

The term cycloalkyl as used in defining the symbol $R_1$ are saturated hydrocarbon rings of 3 to 7 carbons with cyclohexyl being most preferred.

The term aryl as used in defining the symbol $R_1$ includes phenyl, 1-naphthyl, 2-naphthyl, and biphenyl. The terms substituted aryl, substituted phenyl, and substituted phenyl-lower alkylene includes such groups having one or two, preferably one, substituent on the ring. Suitable substituents include lower alkyl groups of 1 to 4 carbons, especially methyl, lower alkoxy groups of 1 to 4 carbons, especially methoxy, lower alkylthio groups of 1 to 4 carbons, especially methylthio, halogens, especially chloro or fluoro, trifluoromethyl, acetyloxy, and hydroxy. The hydroxy substituted aryl, phenyl and phenyl-lower alkylenes are obtained by hydrolysis of the corresponding acetyloxy substituted phenyl compounds as the last step of the synthetic procedure.

The term halogen includes the four common members, i.e., chloro, bromo, fluoro, and iodo, with chloro, bromo, and fluoro being preferred.

The term phenyl-lower alkylene as used in defining the symbols $R_1$ and $R_5$ include groups such as

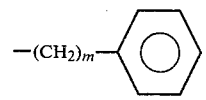

wherein m is an integer from 1 to 4. Preferred phenyl-lower alkylene groups are phenylmethyl and phenylethyl, especially phenylmethyl.

The lower alkanoyl groups represented by $R_5$—CO— are those having the acyl radicals of the lower ($C_2$-$C_7$) fatty acids, for example, acetyl, propionyl, butyryl, isobutyryl, and the like. The lower alkanoyl groups having up to four carbons are preferred with acetyl being especially preferred. Similarly, when $R_5$ in the group $T_5$—CO— is phenyl-lower alkylene, benzoyl is especially preferred.

The asterisk in formula I indicates as asymmetric center which is present in the proline ring. Of course, an additional asymmetric center can be present in the mercapto sidechain depending upon the substituents $R_2$ and $R_3$. The products of formula I accordingly exist in stereoisomeric forms or as racmic mixtures thereof. All of these are within the scope of the invention. The synthesis described below can utilize the racemate or one of the enantiomers as starting materials. When the racemic starting material is used in the synthesis procedure, the stereoisomers obtained in the final product can be separated by conventional chromatographic or fractional crystallization methods. The $X$-$R_1$ group also gives rise to cis-trans isomerism.

Preferably the asymmetric center in the proline ring is in the L-configuration and if there is an asymmetric center in the mercaptoacyl sidechain it is in the D-configuration.

Preferred compounds of formula I are those wherein R is hydrogen; $R_1$ is lower alkyl of 1 to 4 carbons, substituted or unsubstituted phenyl or phenyl-lower alkylene of the formula

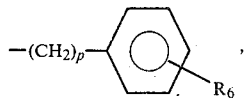

substituted or unsubstituted biphenyl of the formula

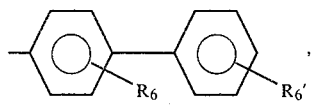

or substituted or unsubstituted 1- or 2-naphthyl of the formula

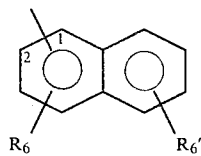

wherein p is zero, 1, or 2; $R_6$ and $R_6'$ are selected from hydrogen, methyl, methoxy, methylthio, chloro, fluoro, trifluoromethyl, and hydroxy provided that only one of $R_6$ and $R_6'$ is other than hydrogen; $R_2$ is hydrogen, methyl, or trifluoromethyl; $R_3$ is hydrogen; n is zero or one; and $R_4$ is hydrogen, acetyl or benzoyl.

More preferred are the above compounds wherein n is one; $R_2$ is hydrogen or methyl, especially methyl; $R_3$ is hydrogen; and the $X$—$R_1$ group is at the 4-position of the L-proline ring, especially wherein the —$X$—$R_1$ group is in the cis configuration.

Most preferred due to its high level of activity and duration of activity as an angiotensin converting enzyme inhibitor are the above compounds wherein X is sulfur and $R_1$ is phenyl.

In these preferred groupings, the compounds wherein $R_4$ is hydrogen are especially useful as final products. The compounds wherein $R_4$ is acetyl are especially useful as intermediates. The compounds wherein $R_4$ is benzoyl are useful as intermediates and are especially useful as final products due to their chemical stability and ease in which they can be handled and formulated.

The ethers and thioethers of formula I can be prepared by various procedures. For example, the ether or thioether proline of the formula

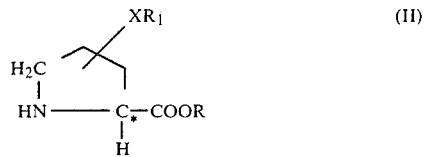

can be coupled with an acid or its chemical equivalent of the formula

wherein $R_4'$ is hydrogen or $R_5$—CO—, to yield the product of the formula

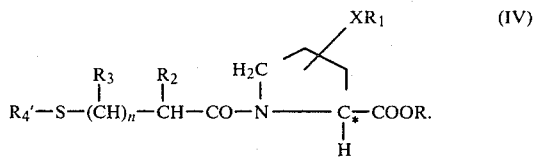

This reaction can be effected in the presence of a coupling agent like dicyclohexylcarbodiimide or the like, or the acid can be activated by formation of its mixed anhydride, symmetrical anhydride, acid halide, active ester or use of Woodward reagent K, N-ethoxycarbonyl-2-ethoxy-1,2-dihydroquinoline or the like. For a review of the methods of acylation, see Methoden der Organishchen Chemie (Houben-Weyl), Vol. XV, part II, page 1 et seq. (1974). Preferably, the acid halide, especially the acid chloride, of formula III is reacted with the acid of formula II.

The ester compounds of formula IV, i.e., R is alkyl, can be converted to the free acid, i.e., R is hydrogen, by conventional means. For example, if R is t-butyl treatment with trifluoroacetic acid and anisole gives the free acid.

The product of formula IV is preferably isolated and purified by crystallization, e.g., by forming the dicyclohexylamine salt and then converting the salt to the free acid form by treatment with an aqueous solution of an acid, such as potassium acid sulfate.

The product of formula IV bearing the acyl group $R_5$—CO— can be converted to the products of formula I wherein $R_4$ is hydrogen by conventional hydrolysis or by ammonolysis.

The products of formula I wherein $R_4$ is

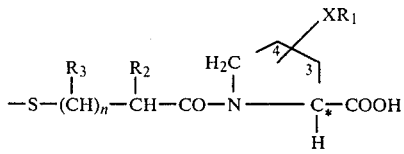

are obtained by directly oxidizing with iodine a product of formula I wherein $R_4$ is hydrogen.

The esters of formula I wherein R is lower alkyl can be obtained from the carboxylic acid compounds, i.e., wherein R is hydrogen, by conventional esterification procedures, e.g., by esterification with a diazoalkane like diazomethane, 1-alkyl-3-p-tolyltriazene, like 1-n-butyl-3-p-tolyltriazene, or the like. The esters can also be prepared by treating the acid with an alcohol of the formula R—OH in the presence of a Lewis acid such as sulfuric acid, boron trifluoride, etc., at room temperature.

The proline reactants of formula II can be prepared by various means. For example, a hydroxy or mercapto proline of the formula

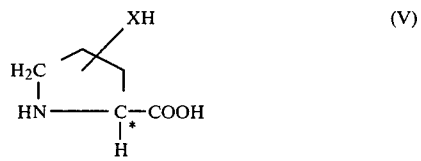

is acylated with an acylating agent such as acetic anhydride, acetyl chloride, propionic anhydride, butyric anhydride, benzylchloroformate, or the like, so as to protect the nitrogen. The $R_1$ group is then introduced by reacting the N-protected form of the compound of formula V with a halide, $R_1$-hal, wherein hal represents a halogen, preferably iodine, in the presence of silver oxide, sodium hydride, sodium hydroxide or the like, to obtain the intermediate having the formula

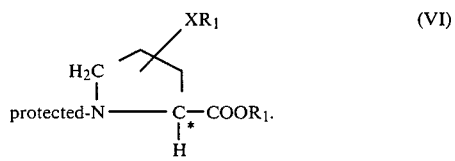

Alkaline hydrolysis of the intermediate of formula VI with a base such as barium hydroxide, sodium hydroxide, potassium hydroxide or the like first yields the free acid (COOH) and then hydrolysis with a mineral acid, such as sulfuric acid, yields the starting material of formula II.

Another method for preparing the proline reactants of formula II is by treating the N-protected tosyloxy proline ester, preferably the methyl ester of the formula

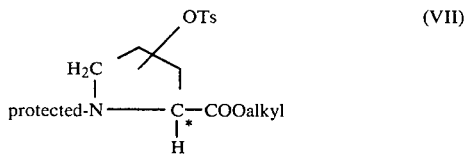

with the sodium salt of the formula (VIII)

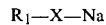

to yield the intermediate of the formula

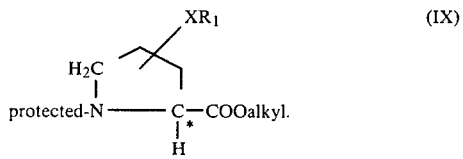

In formula VII the symbol Ts represents

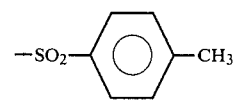

and the N-protecting group is benzyloxycarbonyl, which is preferred, or other commonly employed acyl protecting groups. In this reaction, if the tosylate group is in the cis configuration the $XR_1$ group will be in the trans configuration and if the tosyloxy group is in the trans configuration the $XR_1$ group will be in the cis configuration. The intermediate of formula IX is then treated to remove the alkyl ester group and is then reacted with hydrogen bromide to yield the HBr salt of the proline reactant of formula II which can then be coupled with the acid, preferably the acid chloride, of formula III.

The proline starting materials of formula II where $R_1$ is aryl, substituted aryl, phenyl-lower alkylene or substituted phenyl-lower alkylene can also be obtained by treating the benzyl or alkyl ester of the N-protected proline of formula V with the alcohol $R_1$—OH in the presence of triphenylphosphine and diethylazodicarboxylate according to the procedure of Bittner et al., Chemistry and Industry, Mar. 15, 1975, page 281. Removal of the N-protecting group and the ester group yields the starting material of formula II.

The products of formula I wherein $R_1$ is aryl or substituted aryl and X is oxygen can also be obtained by treating the substituted acylmercaptoacyl proline of the formula

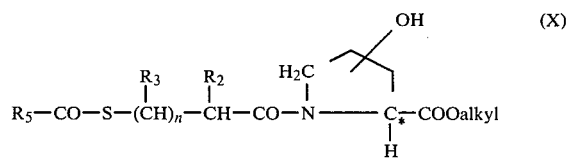

with the alcohol $R_1$—OH in the presence of triphenylphosphine and diethylazodicarboxylate as described above. Removal of the ester group and the acyl group $R_5$—CO—, as described above, yields the desired final products.

The products of formula I wherein X is sulfur and $R_1$ is aryl, substituted aryl, phenyl-lower alkylene or substituted phenyl-lower alkylene can also be obtained by treating the hydroxy substituted acylmercaptoacyl proline of formula X, i.e., X is oxygen, with a disulfide of the formula (XI)

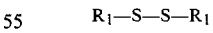

or a sulfide of the formula (XII)

wherein Y is an activating group such as succinimido, which is preferred, phthalimido, etc., or a halide such as Cl or Br. These reactions are performed in the presence of tributylphosphine. In these reactions, if the XH group is in the trans configuration the $XR_1$ group will be in the cis configuration.

The proline starting materials of formula II wherein the $XR_1$ group is attached at the 3-position of the proline can be obtained by treating a 1,2-dehydroproline ester, preferably the t-butyl ester of the formula

(XIII)

with n-bromosuccinimide to yield the corresponding 3-bromo-1,2-dehydroproline ester which is then reacted with a thallium, which is preferred, or potassium salt of the $XR_1$ compound to yield the intermediate of the formula

(XIV)

Treatment with a base such as sodium hydroxide to remove the ester group and a reducing agent such as sodium borohydride yields the desired starting materials.

The proline starting materials of formula II wherein X is sulfur and the $XR_1$ group is attached at the 3-position of the proline can also be obtained by treating the 1,2-dehydroproline ester, preferably the t-butyl ester, of formula XIII with an acylating agent such as benzyl chloroformate, acetyl chloride, etc., to yield the 4,5-dehydro compound

(XV)

which is then reacted with the mercaptan $R_1$—SH to yield

(XVI)

wherein the —S—$R_1$ substituent is in the trans configuration. The N-protecting and alkyl groups are then removed to yield the desired starting material.

Reference is also made to the following publications for additional illustrative information with respect to the production of starting materials and intermediates: Ondetti et al., U.S. Pat. Nos. 4,046,889, 4,105,776 and 4,154,935; Neuberger, J. Chem. Soc., 1945, p. 429–432; Patchett et al., J. Amer. Chem. Soc. 79, p. 185–192 (1957); Baer et al., Can. J. Biochem. and Phys., 37, p 583–587 (1959); Sheehan et al., J. Amer. Chem. Soc. 85, p. 3863–3865 (1963); Magerlein, J. Med. Chem. 10, p. 1161–1163 (1967). The procedures illustrated therein can be utilized as general methods for the synthesis and stereoconversion of compounds utilizable in the invention of this application.

Additional experimental details are found in the examples which are preferred embodiments and also serve as models for the preparation of other members of the group.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example, aralkylamines like, dibenzylamine, N,N-dibenzylethylenediamine, lower alkylamines like methylamine, t-butylamine, procaine, hydroxy substituted lower alkylamines like tris (hydroxymethyl)aminoethane, lower alkyl-piperidines like N-ethylpiperidine, cycloalkylamines like cyclohexylamine or dicyclohexylamine, 1-adamantanamine, benzathine, or salts derived from basic amino acids like arginine, lysine or the like. The physiologically acceptable salts like the sodium, potassium, calcium, magnesium, aluminum, arginine and lysine salts can be used medicinally as described below and are preferred. These are other salts which are not necessarily physiologically acceptable are useful in isolating or purifying a product acceptable for the purposes described below, as illustrated with the dicyclohexylamine salt and the cyclohexylamine salt in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of this invention inhibit the conversion of the decapeptide angiotensin I to angiotensin II and therefore are useful in reducing or relieving hypertension. The compounds of this invention intervene in the renin→angiotensinogen→angiotensin I→angiotensin II sequence by inhibiting angiotensin converting enzyme and reducing or eliminating the formation of the pressor substance angiotensin II. Thus by administration of a hypotensively effective amount of a composition containing one or a combination of compounds of formula I or physiologically acceptable salt thereof, hypertension in the species of mammal suffering therefrom is reduced or alleviated.

A single dose, or preferably two to four divided daily doses, provided in a basis of about 0.1 to about 100 mg. per kilogram per day, preferably about 1 to about 50 mg. per kilogram per day, most preferably about 1 to about 15 mg. per kilogram per day, is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to about 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate or microcrystalline cellulose; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc.

The compounds of this invention can also be formulated in combination with a diuretic for the treatment of hypertension. A combination product comprising a compound of this invention and a diuretic can be administered in a effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, bendroflumethiazide, methchlothiazide, trichlorothiazide, polythiazide or benthiazide, as well as ethacrynic acid, ticrynafen, chlorthalidone, furosemide, musolimine, bumetanide, triamterene, amiloride and spironolactone, and salts of such compounds.

The following examples are illustrative of the invention and constitute preferred embodiments. They also serve a models for the preparation of other members of the group which can be produced by replacement of the given reactants with suitably substituted analogs. All temperatures are in degree Celsius.

EXAMPLE 1

1-(3-Acetylthio-1-oxopropyl)-trans-4-methoxy-L-proline (a) N-Acetyl-trans-4-hydroxy-L-proline A stirred suspension of 26.2 g. (0.2 mole) of trans-4-hydroxy-L-proline in 400 ml. of acetic acid is treated with 26 ml. of acetic anhydride. The solid gradually dissolves after 2 hours of stirring at room temperature. The solution is transferred to a 2 liter flask and the solvent is removed on a rotary evaporator at a bath temperature of 45°. The syrupy residue (57.5 g.) is diluted with 100 ml. of ether to give a crystalline solid. After cooling overnight, the solid is filtered, washed with cold ether and dried in a desiccator. This material (35.7 g.) is pulverized and suspended in 100 ml. of ether, cooled and filtered to give 33.8 g. (98%) of N-acetyl-trans-4-hydroxy-L-proline, 128°-131°. Recrystallization of 0.5 g. of this material from 5 ml. of acetonitrile gives 0.45 g. of colorless solid, m.p. 130°-132°; $[\alpha]_D^{25}$ −92° (c, 1% in EtOH).

(b) N-Acetyl-trans-4-methoxy-L-proline, methyl ester

A mixture of 30.0 g. (0.17 mole) of N-acetyltrans-4-hydroxy-L-proline and 130 g. of silver oxide is pulverized in a mortar and this intimate mixture is added to a 1-liter flask with 300 ml. of acetone. The slurry is stirred, treated portionwise with 130 ml. of methyl iodide and the temperature maintained below 40° by cooling with a cold water bath. After stirring for 7 hours, the mixture is allowed to stand overnight. The solid is filtered, washed well with acetone and the filtrate concentrated on a rotary evaporator to give 38.3 g. of syrupy residue. The latter is redissolved in 350 ml. of acetone and again treated with 130 g. of silver oxide and 130 ml. of methyl iodide to give 41 g. of residue. The latter is distilled to yield 32.2 g. of distillate; b.p. 130°-140° (0.3 mm). After digestion in 30 ml. of cyclohexane and cooling, the nearly colorless solid N-acetyl-trans-4-methoxy-L-proline methyl ester weighs 31.4 g., m.p. 71°-75°. Recrystallization from 31 ml. of ethyl acetate gives 25.1 g. (66%) of colorless solid, m.p. 76°-77°. $[\alpha]_D^{25}$ −83° (c, 1% in EtOH).

(c) trans-4-Methoxy-L-proline

To a stirred solution of 27.0 g. (0.085 mole) of barium hydroxide 8H$_2$O in 525 ml. of water (approx. 3.3 N) is added 11.0 g. (0.05 mole) of N-acetyl-trans-4-methoxy-L-proline methyl ester. The resulting solution is stirred at 18°-20° for 3 hours, cooled and treated with dilute sulfuric acid (8.8 g. of conc. H$_2$SO$_4$ in 20 ml. of water). The acidic suspension is allowed to stand overnight. The mixture is filtered through a thick layer of Celite to give a "milky" filtrate. The latter is concentrated on a rotary evaporator at 50° using a high vacuum pump to give a milky residue weighing 121 g. This material is treated with dilute sulfuric acid (19.0 g. of conc. H$_2$SO$_4$ in 75 ml. of water) and the resulting mixture is stirred and refluxed for 3 hours. After cooling to 30°, the mixture is treated portionwise with 48 g. of barium hydroxide 8H$_2$O and the pH then adjusted from 6.0 to 4.0 with dilute sulfuric acid. After standing overnight, the mixture is filtered through a thick layer of Celite. The "milky" filtrate is concentrated as above to give 50 g. of colorless dry residue. The latter is digested with 200 ml. of hot chloroform and filtered through a bed of Celite to remove the barium sulfate. The slightly turbid filtrate is concentrated on a rotary evaporator to give a gelatinous material (17.7 g.), suspended in 100 ml. of ether, and filtered to give 7.5 g. (94%) of nearly colorless solid, m.p. 185°-190° (dec.). This material is suspended in 30 ml. of warm acetonitrile, cooled and filtered to give 4.0 g. (50%) of a colorless solid, trans-4-methoxy-L-proline, m.p. 209°-211° (dec.); $[\alpha]_D^{25}$ −75° (c, 1% in EtOH).

(d) 1-(3-Acetylthio-1-oxopropyl)-trans-4-methoxy-L-proline

A solution of 3.5 g. (0.024 mole) of trans-4-methoxy-L-proline in 50 ml. of water is stirred, cooled to 5° and 3 g. of sodium carbonate are added. This mixture is treated with a solution of 4.0 g. (0.024 mole) of 3-acetylthiopropionyl chloride in 5 ml. of ether during the course of 10 minutes with the intermittent addition of 3 g. of sodium carbonate to maintain the pH at about 8.0. The mixture is stirred in the ice-bath for an additional hour, 25 ml. of water are added and then a solution of 5 ml. of concentrated hydrochloric acid in 25 ml. of water (CO$_2$ evolution). The strongly acid solution is saturated with sodium chloride and extracted with 50 ml. of ethyl acetate (four times). The organic phases are combined, dried (MgSO$_4$), filtered and the solvent evaporated to give 6.0 g. (90%) of colorless syrupy 1-(3-acetylthio-1-oxopropyl)-trans-4-methoxy-L-proline. This acid is dissolved in 25 ml. of ethyl acetate and treated with 4.7 g. of dicyclohexylamine to give a solution which rapidly becomes a solid mass. An additional 15 ml. of ethyl acetate are added and the mixture is digested on a steam bath, cooled and filtered to give 8.7 g. of the dicyclohexylamine salt, m.p. 170°–172°. After crystallization from 60 ml. of acetonitrile the colorless solid weighs 8.3 g. (75%) m.p. 171°–173°; $[\alpha]_D^{25} -35°$ (c, 1% in EtOH).

The dicyclohexylamine salt is converted to 1-(3-acetylthio-1-oxopropyl)trans-4-methoxy-L-proline by suspending 8.0 g. in 60 ml. of ethyl acetate cooled in an ice bath and treating portionwise with 60 ml. of 10% potassium bisulfate. The clear layers are separated and the aqueous portion extracted with 60 ml. of ethyl acetate (2X). The organic phases are combined, dried ($MgSO_4$), filtered and the solvent is evaporated to give 4.6 g. (80%) of a colorless syrup.

EXAMPLE 2

1-(3-Mercapto-1-oxopropyl)-trans-4-methoxy-L-proline

To the 1-(3-acetylthio-1-oxopropyl)-trans-4-methoxy-L-proline obtained in Example 1 (4.6 g., 0.017 mole) is added a cold solution of 9 ml. of concentrated ammonia in 22 ml. of water. The base dissolves in about 30 minutes and the resulting solution (under Argon) is allowed to stand for 2 hours at room temperature. This solution is cooled, extracted with 25 ml. of ethyl acetate (2X) and the ethyl acetate extract is discarded. The solution is again layered with 25 ml. of ethyl acetate and acidified with 17 ml. of 1:1 hydrochloric acid. The mixture is shaken, separated and the aqueous phase extracted with 25 ml. of ethyl acetate (3X). The organic phases are combined, dried ($MgSO_4$), filtered and the solvent removed on the rotary evaporator to give 2.3 g. (59%) of colorless syrup, 1-(3-mercapto-1-oxopropyl)-trans-4-methoxy-L-proline, $[\alpha]_D^{25} -60°$ (c, 1% in EtOH); $R_f$ 0.49 (MeOH on silica gel, visualized with nitroprusside reagent).

Anal. Calc'd. for $C_9H_{15}NO_4S \cdot \frac{1}{4}H_2O$: C, 45.46; H, 6.57; N, 5.87; S, 13.48. Found: C, 45.42; H, 6.78; N, 5.96; S, 13.27.

An additional 1.1 g. of product (total 3.4 g., 87%) is obtained by saturating the aqueous phase with sodium chloride and extracting with 25 ml. of ethyl acetate (2X).

The sodium salt is formed by treating the syrup with aqueous sodium bicarbonate and freeze drying.

EXAMPLE 3

(trans)-1-[D-3-(Acetylthio)-2-methyl-1-oxopropyl]-4-methoxy-L-proline

A solution of 4.3 g. (0.029 mole) of trans-4-methoxy-L-proline in 50 ml. of water is stirred, cooled to 5° and 3 g. of sodium carbonate are added. This solution is treated with 5.2 g. (0.029 mole) of D-3-(acetylthio)-2-methylpropionyl chloride in 5 ml. of ether during the course of 10 minutes with the intermittent addition of 3 g. of sodium carbonate to maintain the pH at about 8.0. This mixture is stirred in the ice-bath for 1.5 hours, 25 ml. of water are added and then a solution of 6 ml. of concentrated hydrochloric acid in 25 ml. of water ($CO_2$ evolution). The resulting strongly acidic solution is extracted with 50 ml. of ethyl acetate (four times). The organic phases are combined, dried ($MgSO_4$), filtered and the solvent evaporated to give 6.1 g. (73%) of (trans)-1-[D-3-(acetylthio)-2-methyl-1-oxopropyl]-4-methoxy-L-proline as a pale yellow syrupy residue. This acid is dissolved in 50 ml. of ethyl acetate and treated with a solution of 4.0 g. of dicyclohexylamine in 20 ml. of ethyl acetate. The product begins to crystallize from the solution in about a minute. After cooling overnight the nearly colorless solid is filtered and dried, yield 6.7 g., m.p. 175°–177°; $[\alpha]_D^{25} -55°$ (c, 1% in EtOH). Following crystallization from 60 ml. of acetonitrile the nearly colorless solid dicyclohexylamine salt weighs 5.6 g. (41%), m.p. 179°–181°, $[\alpha]_D^{25} -62°$ (c, 1% in EtOH).

The dicyclohexylamine salt is converted to the acid by suspending 5.5 g. in 50 ml. of ethyl acetate, cooling in an ice-bath and treating with 50 ml. of 10% potassium bisulfate. The layers are separated and the aqueous portion is extracted with 50 ml. of ethyl acetate (2X). The organic phases are combined, dried ($MgSO_4$), filtered and the solvent evaporated to give 3.4 g. (41%) of nearly colorless (trans)-1-[D-3-(acetylthio)-2-methyl-1-oxopropyl]-4-methoxy-L-proline as a syrup.

EXAMPLE 4

(trans)-4-Methoxy-1-(D-3-mercapto-2-methyl-1-oxopropyl)-L-proline

To (trans)-1-[D-3-(acetylthio)-2-methyl-1-oxopropyl]-4-methoxy-L-proline (3.4 g.) is added a cold solution of 8 ml. of concentrated ammonia in 20 ml. of water. The base dissolves in about 10 minutes and the resulting solution (under Argon) is allowed to stand at room temperature for two hours. This solution is cooled, extracted with 20 ml. of ethyl acetate (2X), layered with 20 ml. of ethyl acetate and acidified with 15 ml of 1:1 hydrochloric acid. This mixture is saturated with sodium chloride, the layers are separated and the aqueous phase is extracted with 20 ml. of ethyl acetate (3X). The organic phases are combined, dried ($MgSO_4$), filtered and the solvent evaporated to give 2.9 g. (100%) of nearly colorless (trans)-4-methoxy-1-(D-3-mercapto-2-methyl-1-oxopropyl)-L-proline, $[\alpha]_D^{25} -80°$ (c, 1% in EtOH); $R_f$ 0.53 (MeOH on silica gel, visualized with nitroprusside reagent).

Anal. Calc'd. for $C_{10}H_{17}NO_4S \cdot \frac{1}{4}H_2O$: C, 47.69; H, 6.83; N, 5.56; S, 12.73. Found: C, 47.90; H, 6.84; N, 5.85; S, 12.76.

EXAMPLE 5

(trans)-1-[D-3-(Acetylthio)-2-methyl-1-oxopropyl]-4-ethoxy-L-proline

Utilizing the procedure described in Example 3 but substituting an equivalent quantity of trans-4-ethoxy-L-proline (J. Med. Chem., 10, 1161 (1967), for (trans)-4-methoxy-L-proline, (trans)-1-[D-3-(acetylthio)-2-methyl-1-oxopropyl]-4-ethoxy-L-proline is obtained. The product is purified as the dicyclohexylamine salt, m.p. 170°–172° (crystallized from isopropyl alcohol); $[\alpha]_D^{25} -64°$ (c, 1% in EtOH).

This salt (7.75 g.) is converted to the free acid by treating with potassium bisulfate solution as described in Example 4 to give 4.85 g. of nearly colorless (trans)-1-[D-3-(acetylthio)-2-methyl-1-oxopropyl]-4-ethoxy-L-proline as a syrup.

EXAMPLE 6

(trans)-4-Ethoxy-1-(D-3-mercapto-2-methyl-1-oxopropyl)-L-proline

To the material from Example 5 (4.85 g.) is added a cold solution of 9 ml. of concentrated ammonia in 22 ml. of water (under Argon). The mixture is treated in the same manner as Example 4 to give 4.2 g. (100%) of nearly colorless (trans)-4-ethoxy-1-(D-3-mercapto-2-methyl-1-oxopropyl)-L-proline as a syrup, $[\alpha]_D^{25}$ −80° (c, 1% in EtOH); $R_f$ 0.64 (MeOH on silica gel, visualized with nitroprusside reagent).

Anal. Calc'd. for $C_{11}H_{19}NO_4S$: C, 50.55; H, 7.33; N, 5.36; S, 12.27. Found: C, 50.34; H, 7.34; N, 5.39; S, 12.11.

EXAMPLE 7

(cis)-1-[D-3-(Acetylthio)-2-methyl-1-oxopropyl]-4-methoxy-L-proline (a) N-Carbobenzyloxy-cis-4-hydroxy-L-proline N-Carbobenzyloxy-4-keto-L-proline (10 g., 0.038) is dissolved in 300 ml. of methanol and reduced with 5.8 g. (0.15 mole) of sodium borohydride in 20 ml. of water as described in JACS, 79, 189 (1957) to give 8.7 g. of a foamy product. This material is dissolved in 30 ml. of ethanol, treated with 3.5 g. of cyclohexylamine in some ethanol, and diluted to 500 ml. with ether. On seeding and rubbing, the crystalline cyclohexylamine salt separates rapidly to give 10.8 g.; m.p. 163°–165°. This cyclohexylamine salt is then treated with 30 ml. of 2 N HCl and extracted with ethyl acetate (4×50 ml.) to yield as a glass-like material 8 g. of N-carbobenzyloxy-cis-4-hydroxy-L-proline.

(b) N-Carbobenzyloxy-cis-4-methoxy-L-proline, methyl ester

N-Carbobenzyloxy-cis-4-hydroxy-L-proline (13.9 g., 0.052 mole) is treated with 40 g. of silver oxide and 40 ml. of methyl iodide (2x) in acetone (100 ml. initially, then 120 ml.) as described in Example 1(b) to yield 17.5 g. (100%) of N-carbobenzyloxy-cis-4-methoxy-L-proline, methyl ester as a yellow oil.

(c) N-Carbobenzyloxy-cis-4-methoxy-L-proline

The N-carbobenzyloxy-cis-4-methoxy-L-proline, methyl ester (17.5 g., approximately 0.052 mole) is dissolved in 135 ml. of methanol, treated dropwise at −1° to 4° with 32 ml. (0.064 mole) of 2 N sodium hydroxide, then kept at 0° for one hour, and at room temperature overnight. After removing about half of the solvent on a rotary evaporator, the solution is diluted with 300 ml of water, washed with ether (wash discarded), acidified while cooling with 12.5 ml. of 1:1 hydrochloric acid to pH 2, and extracted with ethyl acetate (4×150 ml.). The extracts are combined, dried (MgSO4), filtered and the solvent evaporated to give 15 g. of an orange-yellow syrup. The latter is dissolved in 60 ml. of ethanol, treated with 6 g. of cyclohexylamine in 10 ml. of ethanol and diluted to 900 ml. with ether. On seeding and rubbing, crystalline N-carbobenzyloxy-cis-4-methoxy-L-proline, cyclohexylamine salt separates: weight after cooling overnight 10.2 g., m.p. 148°–150° (s. 144°), $[\alpha]_D^{26}$ −35° (c, 1% in ethanol). Following recrystallization from 40 ml. of acetonitrile, the nearly colorless solid weighs 8.8 g., m.p. 150°–152° (s. 145°), $[\alpha]_D^{26}$ −34° (c, 1% in ethanol).

The cyclohexylamine salt is treated with hydrochloric acid to yield 6.9 g. (48%) of N-carbobenzyloxy-cis-4-methoxy-L-proline as a pale yellow viscous syrup, $[\alpha]_D^{26}$ −32° (c, 1% in ethanol).

(d) cis-4-Methoxy-L-proline

A mixture of 6.8 g. of N-carbobenzyloxy-cis-4-methoxy-L-proline, 210 ml. of 2:1 methanol and water, and 2.3 g. of 5% Pd-C is placed on a hydrogenator at 3 atmospheres of hydrogen for four hours. The mixture is filtered to remove the catalyst and the filtrate evaporated to give 3.15 g. of a grayish solid; m.p. 218°–220° (dec.). A sample is crystallized from methanol-ether to yield colorless cis-4-methoxy-L-proline, m.p. 224°–226° (dec.), $[\alpha]_D^{25}$ −42° (c, 1% in methanol).

Anal. Calc'd. for $C_6H_{11}NO_3$: C, 49.64; H, 7.64; N, 9.65. Found: C, 49.63; H, 7.71; N, 9.54.

(e) (cis)-1-[D-3-(Acetylthio)-2-methyl-1-oxopropyl]-4-methoxy-L-proline cis-4-Methoxy-L-proline (3 g., 0.021 mole) and 4.2 g. (0.023 mole) of D-3-acetylthio-2-methylpropionyl chloride in 5 ml. of ether are reacted in 60 ml. of water in the presence of sodium bicarbonate as described in Example 3. Approximately 20 ml. of 25% sodium carbonate (w/v) is required to bring the pH initially to 8.5 and to maintain it at 7.5 to 8.4 during the acylation. The resulting crude viscous product (6.4 g.) is dissolved in 50 ml. of ethyl acetate and treated with 3.9 g. of dicyclohexylamine in 20 ml. of ethyl acetate. The product crystallizes from the solution and is filtered and dried to yield 6.6 g. of dicyclohexylamine salt, m.p. 172°–174° (s. 170°), $[\alpha]_D^{26}$ −60° (c, 1% in ethanol). 6.5 g. of this material is recrystallized from 35 ml. of acetonitrile to yield 6 g. of colorless solid dicyclohexylamine salt; m.p. 173°–175° (s. 170°), $[\alpha]_D^{26}$ −60° (c, 1% in ethanol).

Anal. Calc'd. for $C_{12}H_{19}NO_5S.C_{12}H_{23}N$: C, 61.24; H, 9.00; N, 5.95; S, 6.81. Found: C, 61,16; H, 8.81; N, 5.95; S, 6.67.

Utilizing the procedure of Example 3, the dicyclohexylamine salt is converted to the acid by suspending 5.9 g. in 60 ml. of ethyl acetate, cooling in an ice-bath and treating with 60 ml. of 10% potassium bisulfate. The layers are separated and the aqueous phase is extracted with 50 ml. of ethyl acetate (4x). The organic phases are combined, dried (MgSO4), filtered and the solvent evaporated to give 3.5 g. (60%) of colorless (cis)-1-[D-3-(acetylthio)-2-methyl-1-oxopropyl]-4-methoxy-L-proline; m.p. 90°–92° (triturated with ether), $[\alpha]_D^{26}$ −139° (c, 1% in ethanol), $R_f$ 0.63 (methanol on silica gel).

Anal. Calc'd. for $C_{12}H_{19}NO_5S$: C, 49.81; H, 6.62; N, 4.84. Found: C, 49.85; H, 6.66; N, 4.97.

EXAMPLE 8

(cis)-4-Methoxy-1-(D-3-mercapto-2-methyl-1-oxopropyl)-L-proline

The (cis)-1-[D-3-(acetylthio)-2-methyl-1-oxopropyl]-4-methoxy-L-proline (2.9 g., 0.01 mole) is hydrolyzed in 15 ml. water containing 6.5 ml. of concentrated ammonia as described in Example 4 to give 2.3 g. (93%) of extremely viscous (cis)-4-methoxy-1-(D-3-mercapto-2-methyl-1-oxopropyl)-L-proline which becomes waxy on standing; $[\alpha]_D^{26}$ −88° (c, 1% in ethanol).

EXAMPLE 8a

(cis)-4-Methoxy-1-(D-3mercapto-2-methyl-1-oxopropyl)-L-proline, 1-adamantanamine salt A solution of 0.55 g. (0.0022 mole) of cis-4-methoxy-1-(D-3-mercapto-2-methyl-1-oxopropyl)-L-proline in 15 ml. of ethyl acetate is treated under an atmosphere of argon with a warm solution of 0.34 g. (0.0022 mole) of 1-adamantaneamine in 10 ml. of ethyl acetate to precipitate the salt. After three hours in the cold, the colorless solid is filtered under argon (solvent held tenaciously), washed with some cold ethyl acetate, and dried in vacuo for twenty hours to yield 0.7 g. (79%) of (cis)-4-methoxy-1-(D-3-mercapto-2-methyl-1-oxopropyl)-L- proline, 1-adamantanamine salt, m.p. 215°–217° (s. 210°, dec. 220°), $[\alpha]_D^{26}$ −60° (c, 1% in methanol).

EXAMPLE 9

(cis)-4-Methoxy-1-(3-mercapto-2-methyl-1-oxopropyl)-L-proline (a) (cis)-4-Methoxy-1-[3-(benzoylthio)-2-methyl-1-oxopropyl]-L-proline Interaction of 3-benzoylthio-2-methylpropionyl acid chloride (prepared by treating 3-benzoylthio-2-methylpropanoic acid with thionyl chloride) with cis-4-methoxy-L-proline according to the general procedure of Example 3 yields (cis)-4-methoxy-1-[3-(benzoylthio)-2-methyl-1-oxopropyl]-L-proline.

(b) (cis)-4-Methoxy-1-(3-mercapto-2-methyl-1-oxopropyl)-L-proline

Hydrolysis of (cis)-4-methoxy-1-[3-(benzoylthio)-2-methyl-1-oxopropyl]-2-proline with an aqueous ammonia solution according to the general procedure of Example 4 yields (cis)-4-methoxy-1-(3-mercapto-2-methyl-1-oxopropyl)-L-proline.

EXAMPLE 10

(trans)-1-[D-3-(Acetylthio)-2-methyl-1-oxopropyl]-4-propoxy-L-proline (a) N-acetyl-trans-4-propoxy-L-proline, propyl ester Interaction of 30 g. of N-acetyl-trans-4-hydroxy-L-proline from Example 1(a) with 110 g. of silver oxide and 110 ml. of propyl iodide in 300 ml. of acetone according to the procedure of Example 1(b) gives 19.6 g. (41%) of pale yellow-orange N-acetyl-trans-4-propoxy-L-proline, propyl ester; b.p. 155°–165° (0.2 mm.).

(b) N-Acetyl-trans-4-propoxy-L-proline

A solution of 6 g. (0.15 mole) of sodium hydroxide in 150 ml. of water is added to 19.4 g. (0.075 mole) of N-acetyl-trans-4-propoxy-L-proline, propyl ester to give a pale orange solution. After standing overnight at room temperature, the solution is extracted with 60 ml. of ethyl acetate (wash discarded), then acidified with 1:1 hydrochloric acid, then saturated with sodium chloride and extracted with 50 ml. of chloroform (3x). The organic phases are combined, dried (MgSO$_4$), filtered and the solvent evaporated to give 12.6 g. of a brown oil. The latter is dissolved in 80 ml. of ethyl acetate and treated with a solution of 10.7 g. of dicyclohexylamine in 20 ml. of ethyl acetate. The salt crystallizes at room temperature. After standing overnight under refrigeration, the dicyclohexylamine salt is filtered and washed with cold ethyl acetate to give 17.3 g. of nearly colorless solid dicyclohexylamine salt; m.p. 148°–153°. Recrystallization of this material from 125 ml. of ethyl acetate gives 14.5 g. of colorless dicyclohexylamine salt; m.p. 157°–159°, $[\alpha]_D^{25}$ −30° (c, 1% in ethanol).

Anal. Cald'd. for $C_{10}H_{17}NO_4 \cdot C_{12}H_{23}N$: C, 66.63; H, 10.17; N, 7.07. Found: C, 66.47; H, 10.22; N, 7.06.

The dicyclohexylamine salt (14.4 g.) is converted to the free acid by pulverizing, suspending in 100 ml. of ethyl acetate and treating the slurry portionwise with 100 ml. of 10% potassium bisulfate. The organic phase is separated and the aqueous phase is extracted with 100 ml. of ethyl acetate (2x). The organic phases are combined, dried (MgSO$_4$), filtered, and the solvent evaporated to give 6.7 g. (41%) of N-acetyl-trans-4-propoxy-L-proline as a pale brown liquid.

(c) (trans)-1-[D-3-(Acetylthio)-2-methyl-1-oxopropyl]-4-propoxy-L-proline

N-Acetyl-trans-4-propoxy-L-proline (6.4 g., 0.03 mole) is treated with a solution of 10 g. of concentrated sulfuric acid in 100 ml. of water and the resulting solution is stirred and refluxed for three hours. The solution is then cooled to 15°, treated portionwise with 12 g. of sodium carbonate to bring the pH to 8.0, and then treated with a solution of 5.4 g. (0.03 mole) of D-3-acetylthio-2-methylpropionyl chloride in 5 ml. of ether during 10 minutes while 7 g. of sodium carbonate are added to maintain the pH at about 8.0. The mixture is then stirred in the ice-bath for 30 minutes and at room temperature for one hour. The product is then isolated and purified as a dicyclohexylamine salt according to the procedure of Example 3 to yield 6.3 g. of dicyclohexylamine salt; m.p. 165°–167° (from acetonitrile), $[\alpha]_D^{25}$ −56° (c, 1% in ethanol).

Anal. Calc'd. for $C_{14}H_{23}NO_5S \cdot C_{12}H_{23}N$: C, 62.62; H, 9.30; N, 5.61; S, 6.43. Found: C, 62.35; H, 9.48; N, 5.88; S, 6.45.

The dicyclohexylamine salt (6.1 g.) is converted to the free acid by suspending in 60 ml. of ethyl acetate, cooling in an ice-bath and treating with 60 ml. of 10% potassium bisulfate. The layers are separated and the aqueous phase is extracted with 60 ml. of ethyl acetate (2x). The organic phases are combined, dried (MgSO$_4$), filtered and the solvent evaporated to give 4.0 g. (42%) of (trans)-1-[D-3-(acetylthio)-2-methyl-1-oxopropyl]-4-propoxy-L-proline as a nearly colorless syrup.

EXAMPLE 11

1-(D-3-Mercapto-2-methyl-1-oxopropyl)-trans-4-propoxy-L-proline

Hydrolysis of 4.0 g. of (trans)-1-[D-3-(acetylthio)-2-methyl-1-oxopropyl]-4-propoxy-L-proline with 8 ml. of concentrated ammonia in 20 ml. of water under argon according to the procedure of Example 4 gives 3.42 g. (97%) of 1-(D-3-mercapto-2-methyl-1-oxopropyl)-trans-4-propoxy-L-proline as a nearly colorless syrup, $[\alpha]_D^{25}$ −72° (c, 1% in ethanol).

Anal. Calc'd. for $C_{12}H_2NO_4S \cdot \frac{1}{4} H_2O$: C, 51.49; H, 7.74; N, 5.05; S, 11.46. Found: C, 51.66; H, 7.76; N, 5.94; S, 10.51.

EXAMPLE 12

1-(3-Mercapto-1-oxopropyl)-cis-4-methoxy-L-proline (a) 1-(3-Acetylthio-1-oxopropyl)-cis-4-methoxy-L-proline Following the procedure of Example 1 (d), cis-4-methoxy-L-proline is treated with a solution of 3-acetylthiopropyl chloride in the presence of sodium carbonate to yield 1-(3-acetylthio-1-oxopropyl)-cis-4-methoxy-L-proline.

(b) 1-(3-Mercapto-1-oxopropyl)-cis-4-methoxy-L-proline

The 1-(3-acetylthio-1-oxopropyl)-cis-4-methoxy-L-proline is hydrolyzed with an aqueous solution of ammonia according to the procedure of Example 2 to yield 1-(3-mercapto-1-oxopropyl)-cis-4-methoxy-L-proline.

EXAMPLE 13

(cis)-4-Ethoxy-1-(D-3-mercapto-2-methyl-1-oxopropyl)-L-proline (a) cis-4-Ethoxy-L-proline Following the procedure of Example 7, parts (a) to (d) but substituting ethyl iodide for the methyl iodide in part (b), one obtains (cis)-4-ethoxy-L-proline.

(b) (cis)-1-[D-3-(Acetylthio)-2-methyl-1-oxopropyl]-4-ethoxy-L-proline

The (cis)-4-ethoxy-L-proline is reacted with a solution of D-3-acetylthio-2-methylpropionyl chloride in the presence of sodium carbonate according to the procedure of Example 7(e) to yield (cis)-1-[D-3-(acetylthio)-2-methyl-1-oxopropyl]-4-ethoxy-L-proline.

(c) (cis)-4-Ethoxy-1-(D-3-mercapto-2-methyl-1-oxopropyl)-L-proline

The cis-1-[D-3-(acetylthio)-2-methyl-1-oxopropyl]-4-ethoxy-L-proline is hydrolyzed with a solution of aqueous ammonia according to the procedure of Example 8 to yield (cis)-4-ethoxy-1-(D-3-mercapto-2-methyl-1-oxopropyl)-L-proline.

EXAMPLE 14

(trans)-4-Allyloxy-1-(D-3-mercapto-2-methyl-1-oxopropyl)-L-proline (a) (trans)-4-Allyloxy-L-proline Using the procedure of Example 1, part b, but substituting allyl bromide for methyl iodide gives the (trans)-N-acetyl-4-allyl-L-proline, allyl ester. The latter is then hydrolyzed as described in Example 1, part c, to give (trans)-4-allyloxy-L-proline.

(b) (trans)-1-[D-3-(Acetylthio)-2-methyl-1-oxopropyl]-4-allyloxy-L-proline

Interaction of the (trans)-4-allyloxy-L-proline from part (a) with an equivalent quantity of D-3-(acetylthio)-2-methylpropionyl chloride according to the procedure of Example 3 gives (trans)-1-[D-3-(acetylthio)-2-methyl-1-oxopropyl]-4-allyloxy-L-proline.

(c) (trans)-4-Allyloxy-1-(D-3-mercapto-2-methyl-1-oxopropyl)-L-proline

The (trans)-1-[D-3-(acetylthio)-2-methyl-1-oxopropyl]-4-allyloxy-L-proline is hydrolyzed with an aqueous ammonia solution according to the procedure of Example 4 to give (trans)-4-allyloxy-1-(D-3-mercapto-2-methyl-1-oxopropyl)-L-proline.

EXAMPLE 15

1-(D-3-Mercapto-2-methyl-1-oxopropyl)-trans-4-propargyloxy-L-proline (a) (trans)-4-propargyloxy-L-proline Using the procedure of Example 1, part b, but substituting propargyl bromide for methyl iodide gives the (trans)-N-acetyl-4-propargyl-L-proline, propargyl ester. The latter is then hydrolyzed as described in Example 1, part c, to give the (trans)-4-propargyloxy-L-proline.

(b) (trans)-1-[D-3-(Acetylthio)-2-methyl-1-oxopropyl]-4-propargyloxy-L-proline

Interaction of the (trans)-4-propargyloxy-L-proline from part (a) with an equivalent quantity of D-3-(acetylthio)-2-methylpropionyl chloride according to the procedure of Example 3 gives (trans)-1-[D-3-(acetylthio)-2-methyl-1-oxopropyl]-4-propargyloxy-L-proline.

(c) 1-(D-3-Mercapto-2-methyl-1-oxopropyl)-trans-4-propargyloxy-L-proline

The (trans)-1-[D-3-(acetylthio)-2-methyl-1-oxopropyl]-4-propargyl-L-proline is hydrolyzed with an aqueous ammonia solution according to the procedure of Example 4 to give 1-(D-3-mercapto-2-methyl-1-oxopropyl)-trans-4-propargyloxy-L-proline.

EXAMPLE 16

(trans)-4-Benzyloxy-1-(D-3-mercapto-2-methyl-1-oxopropyl)-L-proline (a) (trans)-4-Benzyloxy-L-proline Using the procedure of Example 1, part b, but substituting benzyl chloride for methyl iodide gives the (trans)-N-acetyl-4-benzyloxy-L-proline, benzyl ester. The latter is then hydrolyzed as described in Example 1, part c, to give (trans)-4-benzyloxy-L-proline.

(b) (trans)-1-[D-3-(Acetylthio)-2-methyl-1-oxopropyl]-4-benzyloxy-L-proline

Interaction of the (trans)-4-benzyloxy-L-proline from part (a) with an equivalent quantity of D-3-(acetylthio)-2-methylpropionyl chloride according to the procedure of Example 3 gives (trans)-1-[D-3-(acetylthio)-2-methyl-1-oxopropyl]-4-benzyloxy-L-proline.

(c) (trans)-4-Benzyloxy-1-(D-3-mercapto-2-methyl-1-oxopropyl)-L-proline

The (trans)-1-[D-3-(acetylthio)-2-methyl-1-oxopropyl]-4-benzyloxyl-L-proline is hydrolyzed with an aqueous ammonia solution according to the procedure of Example 4 to give (trans)-4-benzyloxy-1-(D-3-mercapto-2-methyl-1-oxopropyl)-L-proline.

EXAMPLE 17

1-(D-3-Mercapto-2-methyl-1-oxopropyl)-trans-4-phenethyloxy-L-proline (a) (trans)-4-Phenethyloxy-L-proline Using the method of Example 1, part b, but substituting phenethyl bromide for methyl iodide gives the (trans)-N-acetyl-4-phenethyloxy-L-proline, phenethyl ester. The latter is then hydrolyzed as described in Example 1, part c, to give (trans)-4-phenethyloxy-L-proline.

(b) (trans)-1-[D-3-(Acetylthio)-2-methyl-1-oxopropyl]-4-phenethyloxy-L-proline

Interaction of the (trans)-4-phenethyloxy-L-proline from part (a) with an equivalent quantity of D-3-(acetylthio)-2-methylpropionyl chloride according to the procedure of Example 3 gives (trans)-1-[D-3-(acetylthio)-2-methyl-1-oxopropyl]-4-phenethyloxy-L-proline.

(c) 1-(D-3-Mercapto-2-methyl-1-oxopropyl)-trans-4-phenethyloxy-L-proline

The trans-1-[D-(acetylthio)-2-methyl-1-oxopropyl]-4-phenethyloxy-L-proline is hydrolyzed with an aqueous ammonia solution according to the procedure of Example 4 to give 1-(D-3-mercapto-2-methyl-1-oxopropyl)-trans-4-phenethyloxy-L-proline.

EXAMPLE 18

1-(D-3-Mercapto-2-methyl-1-oxopropyl)-cis-3-methoxy-L-proline (a) 1-[D-3-(Acetylthio)-2-methyl-1-oxopropyl]-cis-3-methoxy-L-proline Utilizing the procedure described in Example 7, but substituting an equivalent quantity of (cis)-3-methoxy-L-proline (J. Amer. Chem. Soc. 85, 3863 (1963)) for the (cis)-4-methoxy-L-proline, 1-[D-3-(acetylthio)-2-methyl-1-oxopropyl]-cis-3-methoxy-L-proline is obtained.

(b) 1-(D-3-Mercapto-2-methyl-1-oxopropyl)-cis-3-methoxy-L-proline

The 1-[D-3-(acetylthio)-2-methyl-1-oxopropyl]-cis-3-methoxy-L-proline is hydrolyzed with an aqueous ammonia solution according to the procedure of Example 4 to yield 1-(D-3-mercapto-2-methyl-1-oxopropyl)-cis-3-methoxy-L-proline.

EXAMPLE 19

1-(D,L-3-Mercapto-2-methyl-1-oxopropyl)-trans-3-methoxy-L-proline (a) 1-[D,L-3-(Acetylthio)-2-methyl-1-oxopropyl]-trans-3-methoxy-L-proline Interaction of equivalent quantities of (trans)-3-methoxy-L-proline (J. Amer. Chem. Soc. 85, 3863 (1963)) and D,L-3-(acetylthio)-2-methylpropionyl chloride according to the procedure described in Example 3 gives 1-[D,L-3-(acetylthio)-2-methyl-1-oxopropyl]-trans-3-methoxy-L-proline.

(b) 1-(D,L-3-Mercapto-2-methyl-1-oxopropyl)-trans-3-methoxy-L-proline

The 1-[D,L-3-(acetylthio)-2-methyl-1-oxopropyl]-trans-3-methoxy-L-proline is hydrolyzed with an aqueous ammonia solution according to the procedure of Example 4 to yield 1-(D,L-3-mercapto-2-methyl-1-oxopropyl)-trans-3-methoxy-L-proline.

EXAMPLE 20

1-(D-3-Mercapto-2-methyl-1-oxopropyl)-cis-4-methylthio-L-proline (a) 1-[D-3-(Acetylthio)-2-methyl-1-oxopropyl]-cis-4-methylthio-L-proline Interaction of equivalent quantities of cis-4-methylthio-L-proline [J. Amer. Chem. Soc., 79, 185 (1957)] and D-3-(acetylthio)-2-methylpropionyl chloride according to the procedure of Example 3 gives 1-[D-3-(acetylthio)-2-methyl-1-oxopropyl]-cis-4-methylthio-L-proline.

(b) 1-(D-3-Mercapto-2-methyl-1-oxopropyl)-cis-4-methylthio-L-proline

The 1-[D-3-(acetylthio)-2-methyl-1-oxopropyl]-cis-4-methylthio-L-proline is hydrolyzed with an aqueous ammonium solution according to the procedure of Example 4 to give 1-(D-3-mercapto-2-methyl-1-oxopropyl)-cis-4-methylthio-L-proline.

EXAMPLE 21

1-(D-3-Mercapto-2-methyl-1-oxopropyl)-trans-4-methylthio-L-proline (a) 1-[D-3-(Acetylthio)-2-methyl-1-oxopropyl]-trans-4-methylthio-L-proline Interaction of equivalent quantities of trans-4-methylthio-L-proline [J. Amer. Chem. Soc., 79, 185 (1957)] and D-3-(acetylthio)-2-methylpropionyl chloride according to the procedure of Example 3 gives 1-[D-3-(acetylthio)-2-methyl-1-oxopropyl]-trans-4-methylthio-L-proline.

(b) 1-(D-3-Mercapto-2-methyl-1-oxopropyl)-trans-4-methylthio-L-proline

The 1-[D-3-(acetylthio)-2-methyl-1-oxopropyl]-trans-4-methylthio-L-proline is hydrolyzed with an aqueous ammonia solution according to the procedure of Example 4 to give 1-(D-3-mercapto-2-methyl-1-oxopropyl)-trans-4-methylthio-L-proline.

EXAMPLE 22

1-(D-3-Mercapto-3-methyl-1-oxopropyl)-cis-4-(4-pentenylthio)-L-proline (a) (cis)-4-(4-Pentenylthio)-L-proline Interaction of (cis)-N-acetyl-4-mercapto-L-proline [Chem. Pharm. Bull., 20, 543 (1972)] with 5-bromo-1-pentene in acetone in the presence of silver oxide according to the procedure of Example 1, part b, gives the (cis)-N-acetyl-4-(4-pentenylthio)-L-proline, 4-pentenyl ester. The latter is then hydrolyzed as described in Example 1, part c, to give the cis-4-(4-pentenylthio)-L-proline.

(b) 1-[D-3-(Acetylthio)-3-methyl-1-oxopropyl]-cis-4-(4-pentenylthio)-L-proline

Interaction of cis-4-(4-pentenylthio)-L-proline with an equivalent amount of D-3-(acetylthio)-3-methylpropionyl chloride according to the procedure of Example 3 gives 1-[D-3-(acetylthio)-3-methyl-1-oxopropyl]-cis-4-(4-pentenylthio)-L-proline.

(c) 1-(D-3-Mercapto-3-methyl-1-oxopropyl)-cis-4-(4-pentenylthio)-L-proline

The 1-[D-3-(acetylthio)-3-methyl-1-oxopropyl]-cis-4-(4-pentenylthio)-L-proline is hydrolyzed with an aqueous ammonia solution according to the procedure of Example 4 to yield 1-(D-3-mercapto-3-methyl-1-oxopropyl)-cis-4-(4-pentenylthio)-L-proline.

EXAMPLE 23

(trans)-1-[D-3-(Acetylthio)-2-methyl-1-oxopropyl]-4-methoxy-L-proline, methyl ester A solution of the material from Example 3 in ether is treated with a slight excess of diazomethane. After standing at room temperature, the solvent is evaporated to give (trans)-1-[D-3-(acetylthio)-2-methyl-1-oxopropyl]-4-methoxy-L-proline, methyl ester.

Similarly, by employing the cis material from Example 7 in this procedure one obtains (cis)-1-[D-3-(acetylthio)-2-methyl-1-oxopropyl]-4-methoxy-L-proline, methyl ester.

EXAMPLE 24

1,1'-[Dithiodi-(1-D-3-mercapto-2-methyl-1-oxopropyl)]-bis-[(trans)-4-methoxy-L-proline]

A solution of the material from Example 4 is dissolved in ethanol, stirred and treated with a solution of one equivalent of iodine in ethanol. The pH of the solution is maintained at 6–7 by the addition of N-sodium hydroxide solution. The solvent is evaporated and the residue extracted with ethyl acetate. After drying over MgSO$_4$, the solution is filtered and the solvent is removed to give 1,1'-[dithiodi(1-D-3-mercapto-2-methyl-1-oxopropyl)]-bis-[(trans)-4-methoxy-L-proline].

Similarly, by employing the cis material from Example 8 in this procedure one obtains 1,1'-[dithiodi-(1-D-3-mercapto-2-methyl-1-oxopropyl)]-bis-[(cis)-4-methoxy-L-proline].

EXAMPLE 25

Sodium salt of (trans)-4-methoxy-1-(D-3-mercapto-2-methyl-1-oxopropyl)-L-proline A solution of 2.5 g. of material from Example 4 in 25 ml. of water is treated with 0.84 g. of sodium bicarbonate. The solution is freeze-dried to give the sodium salt of (trans)-4-methoxy-1-(D-3-mercapto-2-methyl-1-oxopropyl)-L-proline.

Similarly, by employing the cis material from Example 8 in this procedure one obtains the sodium salt of (cis)-4-methoxy-1-(D-3-mercapto-2-methyl-1-oxopropyl)-L-proline.

EXAMPLE 26

1-(4-Mercapto-1-oxobutyl)-cis-4-methoxy-L-proline (a) (cis)-1-(4-Acetylthio-1-oxobutyl)-4-methoxy-L-proline Interaction of an equivalent quantity of (cis)-4-methoxy-L-proline with 4-acetylthiobutyroyl chloride according to the procedure described in Example 1 gives (cis)-1-(4-acetylthio-1-oxobutyl)-4-methoxy-L-proline.

(b) 1-(4-Mercapto-1-oxobutyl)-cis-4-methoxy-L-proline

Hydrolysis of (cis)-1-(4-acetylthio-1-oxobutyl)-4-methoxy-L-proline with an aqueous ammonia solution according to the procedure of Example 2 yields 1-(4-mercapto-1-oxobutyl)-cis-4-methoxy-L-proline.

EXAMPLE 27

1-(L-3-Mercapto-2-ethyl-1-oxopropyl)-trans-4-methoxy-D-proline (a) (trans)-1-[L-(3-Acetylthio)-2-ethyl-1-oxopropyl]-4-methoxy-D-proline Utilizing the procedure of Example 1 but substituting (trans)-4-hydroxy-D-proline for the (trans)-4-hydroxy-L-proline in part (a) the (trans)-4-methoxy-D-proline is obtained. By interacting the latter compound with L-(3-acetylthio)-2-ethylpropionyl chloride according to the procedure of Example 3, (trans)-1-[L-(3-acetylthio)-2-ethyl-1-oxopropyl]-4-methoxy-D-proline is obtained.

(b) 1-(L-3-Mercapto-2-ethyl-1-oxopropyl)-trans-4-methoxy-D-proline

Hydrolysis of (trans)-1-[L-(3-acetylthio)-2-ethyl-1-oxopropyl]-4-methoxy-D-proline with an aqueous ammonia solution according to the procedure of Example 4 gives 1-(L-3-mercapto-2-ethyl-1-oxopropyl)-trans-4-methoxy-D-proline.

EXAMPLE 28

1-(2-Mercapto-1-oxoethyl)-trans-4-methoxy-L-proline (a) (trans)-1-(2-Acetylthio-1-oxoethyl)-4-methoxy-L-proline Utilizing the procedure of Example 1, but substituting 2-acetylthioacetyl chloride for the 3-acetylthiopropionyl chloride, (trans)-1-(2-acetylthio-1-oxoethyl)-4-methoxy-L-proline is obtained.

(b) 1-(2-Mercapto-1-oxoethyl)-trans-4-methoxy-L-proline

Hydrolysis of trans-1-(2-acetylthio-1-oxoethyl)-4-methoxy-L-proline with an aqueous ammonia solution according to the procedure of Example 2 yields 1-(2-mercapto-1-oxoethyl)-trans-4-methoxy-L-proline.

EXAMPLE 29

1-(2-Mercapto-1-oxoethyl)-cis-4-methoxy-L-proline (a) (cis)-1-(2-Acetylthio-1-oxoethyl)-4-methoxy-L-proline Following the procedure of Example 28, cis-4-methoxy-L-proline is treated with a solution of 2-acetylthioacetyl chloride in the presence of sodium carbonate to yield (cis)-1-(2-acetylthio-1-oxoethyl)-4-methoxy-L-proline.

(b) 1-(2-Mercapto-1-oxoethyl)-cis-4-methoxy-L-proline

Hydrolysis of (cis)-1-(2-acetylthio-1-oxoethyl)-4-methoxy-L-proline with an aqueous ammonia solution yields 1-(2-mercapto-1-oxoethyl)-cis-4-methoxy-L-proline.

EXAMPLE 30

1-(2-Mercapto-1-oxoethyl)-cis-4-methylthio-L-proline (a) (cis)-1-(2-Acetylthio-1-oxoethyl)-4-methylthio-L-proline Interaction of equivalent quantities of (cis)-4-methylthio-L-proline [J. Amer. Chem. Soc., 79, 185 (1957)] and 2-acetylthioacetyl chloride according to the procedure described in Example 1, yields (cis)-1-(2-acetylthio-1-oxoethyl)-4-methylthio-L-proline.

(b) 1-(2-Mercapto-1-oxoethyl)-cis-4-methylthio-L-proline

Hydrolysis of (cis)-1-(2-acetylthio-1-oxoethyl)-4-methylthio-L-proline with an aqueous ammonia solution according to the procedure of Example 2 yields 1-(2-mercapto-1-oxoethyl)-cis-4-methylthio-L-proline.

EXAMPLE 31

1-(D-3-Mercapto-3-methyl-1-oxopropyl)-cis-4-(4-pentynylthio)-L-proline (a) (cis)-1-[D-3-(Acetylthio)-3-methyl-1-oxopropyl]-4-(4-pentynylthio)-L-proline Interaction of (cis)-N-acetyl-4-mercapto-L-proline with 5-chloro-1-pentyne in acetone in the presence of silver oxide according to the procedure of Example 1, part b, gives (cis)-N-acetyl-4-(4-pentynylthio)-L-proline, 4-pentynyl ester. The latter is then hydrolyzed as described in Example 1, part c, to give the (cis)-N-acetyl-4-(4-pentynylthio)-L-proline. Interaction of this compound with an equivalent quantity of D-3-(acetylthio)-3-methylpropionyl chloride according to the procedure of Example 3 gives (cis)-1-[D-3-(acetylthio)-3-methyl-1-oxopropyl]-4-(4-pentynylthio)-L-proline.

(b) 1-(D-3-Mercapto-3-methyl-1-oxopropyl)-cis-4-(4-pentynylthio)-L-proline

Hydrolysis of (cis)-1-[D-3-(acetylthio)-3-methyl-1-oxopropyl]-4-(4-pentynylthio)-L-proline with an aqueous ammonia solution according to the procedure of Example 4 gives 1-(D-3-mercapto-3-methyl-1-oxopropyl)-cis-4-(4-pentynylthio)-L-proline.

EXAMPLE 32

(cis)-4-Benzylthio-1-(D,L-3-mercapto-3-ethyl-1-oxopropyl)-L-proline (a) (cis)-1-[D,L-3-(Acetylthio)-3-ethyl-1-oxopropyl]-4-benzylthio-L-proline Interaction of (cis)-N-acetyl-4-mercapto-L-proline with benzyl chloride in acetone in the presence of silver oxide according to the procedure of Example 1, part b, gives (cis)-N-acetyl-4-benzylthio-L-proline, benzyl ester. The latter is hydrolyzed as described in Example 1, part c, to give (cis)-N-acetyl-4-benzylthio-L-proline. Interaction of this compound with an equivalent amount of D,L-3-(acetylthio)valeroyl chloride according to the procedure of Example 3 gives (cis)-1-[D,L-3-(acetylthio)-3-ethyl-1-oxopropyl]-4-(benzylthio)-L-proline.

(b) (cis)-4-Benzylthio-1-(D,L-3-mercapto-3-ethyl-1-oxopropyl)-L-proline

Hydrolysis of (cis)-1-[D,L-3-(acetylthio)-3-ethyl-1-oxopropyl]-4-(benzylthio)-L-proline with an aqueous ammonia solution according to the procedure of Example 4 gives (cis)-4-benzylthio-1-(D,L-3-mercapto-3-ethyl-1-oxopropyl)-L-proline.

EXAMPLE 33

1,1′-[Dithiodi-(1-D-3-mercapto-2-methyl-1-oxopropyl)]-bis[(trans)-4-methylthio-L-proline]

The product of Example 21 is treated with iodine in ethanol according to the procedure described in Example 24 to give 1,1′-[dithiodi-(1-D-3-mercapto-2-methyl-1-oxopropyl)]bis[(trans)-4-methylthio-L-proline ].

EXAMPLE 34

(trans)-4-Cyclohexyloxy-1-(D-3-mercapto-2-methyl-1-oxopropyl)-L-proline (a) (trans)-4-Cyclohexyloxy-L-proline Using the procedure of Example 1, part b, but substituting cyclohexyl bromide for methyl iodide gives the (trans)-N-acetyl-4-cyclohexyl-L-proline, cyclohexyl ester. The latter is then hydrolyzed as described in Example 1, part c, to give (trans)-4-cyclohexyloxy-L-proline.

(b) (trans)-1-[D-3-(Acetylthio)-2-methyl-1-oxopropyl]-4-cyclohexyloxy-L-proline

Interaction of the (trans)-4-cyclohexyloxy-L-proline from part (a) with an equivalent quantity of D-3-(acetylthio)-2-methylpropionyl chloride according to the procedure of Example 3 gives (trans)-1-[D-3-(acetylthio)-2-methyl-1-oxopropyl]-4-cyclohexyloxy-L-proline.

(c) (trans)-4-Cyclohexyloxy-1-(D-3-mercapto-2-methyl-1-oxopropyl)-L-proline

The (trans)-1-[D-3-(acetylthio)-2-methyl-1-oxopropyl]-4-cyclohexyloxy-L-proline is hydrolyzed with an aqueous ammonia solution according to the procedure of Example 4 to give (trans)-4-cyclohexyloxy-1-(D)-3-mercapto-2-methyl-1-oxopropyl)-L-proline.

EXAMPLE 35

(cis)-4-(1,1-Dimethylethoxy)-1-(D-3-mercapto-2-methyl 1-oxopropyl)-L-proline (a) N-Carbobenzyloxy-cis-4-(1,1-dimethylethoxy)-L-proline, methyl ester A solution of 6.0 g. (0.021 mole) of N-carbobenzyloxy-cis-4-hydroxy-L-proline, methyl ester in 60 ml. of methylene chloride is placed in a Parr bomb, stirred magnetically, cooled in a dry ice-isopropanol bath, and treated with approximately 40 ml. of liquified isobutylene followed by 0.75 ml. of concentrated sulfuric acid. The bomb is sealed and the reaction mixture is allowed to warm to room temperature with continued stirring. There is no measurable pressure increase. After stirring at room temperature for four days the bomb is opened and the solution (80 ml.) is diluted with 120 ml. of methylene chloride and washed with 5 g. of sodium bicarbonate in 100 ml. of water. The aqueous phase is back-extracted with 50 ml. of methylene chloride the organic layers are combined and dried ($MgSO_4$), and the solvent evaporated to give 7.5 g. of N-carbobenzyloxy-cis-4-(1,1-dimethylethoxy)-L-proline, methyl ester as a pale yellow oil; $[\alpha]_D^{25}$ −46° (c, 1% in chloroform). TLC (on silica gel): $R_f$ 0.62 (ethyl acetate), $R_f$ 0.43 (7:1 benzene:acetic acid); visualized U.V., $I_2$ vapor.

(b) N-Carbobenzyloxy-cis-4-(1,1-dimethylethoxy)-L-proline

A stirred solution of the methyl ester product from part (a) (7.2 g., 0.02 mole) in 15 ml. of ether is cooled in ice-water and treated portionwise with 42 ml. (0.042 mole) of ice-cold N sodium hydroxide. After stirring and cooling for a total of six hours the cooling bath is removed and stirring is continued overnight at room temperature. The clear solution is washed with 40 ml. of ether (wash discarded), layered with 40 ml. of ethyl acetate, stirred, cooled, and acidified with 8 ml. of 6 N hydrochloric acid. After separating, the aqueous phase is extracted with additional ethyl acetate ($3 \times 40$ ml.), the organic layers are combined and dried ($MgSO_4$), and the solvent evaporated to give 6.8 g. of a pale yellow viscous oil. This oil is dissolved in 50 ml. of acetonitrile and treated with a warm solution of 3.2 g. of 1-adamantanamine in 20 ml. of acetonitrile. The solid adamantanamine salt rapidly separates. After cooling overnight, the colorless salt is filtered under nitrogen, washed with cold acetonitrile and ether, and dried in vacuo to yield 8.8 g. of N-carbobenzyloxy-cis-4-(1,1-dimethylethoxy)-L-proline, adamantanamine salt; m.p. 228°–230° (dec.), s. 215°, $[\alpha]_D^{25}$ −28° (c, 1% in methanol).

Anal. Calc'd. for $C_{17}H_{23}NO_5.C_{10}H_{17}N.0.25\ H_2O$: C, 67.96; H, 8.56; N, 5.87. Found: C, 67.77; H, 8.54; N, 5.93.

Treatment of the above adamantanamine salt (8.5 g.) with acid yields 5.5 g. of N-carbobenzyloxy-cis-4-(1,1-dimethylethoxy)-L-proline as a nearly colorless viscous syrup. TLC:$R_f$ 0.20 (85:15 toluene:acetic acid on silica gel; visualized $I_2$ vapor or PMA plus heat).

(c) cis-4-(1,1-Dimethoxyethoxy)-L-proline

The N-carbobenzyloxy product from part (b) (5.5 g., 0.017 mole) is hydrogenated in 165 ml. of 2:1 methanol:water under 3 atmospheres of hydrogen in the presence of 1.7 g. of 5% palladium/carbon catalyst to give 3.2 g. of a sticky, partly solid product. This material is suspended in 30 ml. of acetonitrile, rubbed, and cooled overnight to yield 1.35 g. of cis-4-(1,1-dimethylethoxy)-L-proline as a colorless solid; m.p. 240°–242° (dec.); preceded by gradual darkening and scintering; $[\alpha]_D^{25}$ −36° (c, 0.5% in methanol).

Anal. Calc'd. for $C_9H_{17}NO_3.0.25\ H_2O$: C, 56.37; H, 9.20; N, 7.31. Found: C, 56.26; H, 9.27; N, 7.26.

(d) 1-[D-3-(Acetylthio)-2-methyl-1-oxopropyl]-cis-4-(1,1-dimethylethoxy)-L-proline The cis-4-(1,1-dimethylethoxy)-L-proline from part (c) (1.3 g., 0.0069 mole) is reacted with 1.4 g. (0.0078 mole) of D-3-acetylthio-2-methylpropionyl chloride in 20 ml. of water in the presence of sodium bicarbonate according to the procedure of Example 3 to yield 2.2 g. of a nearly colorless viscous oil. The resulting crude product is dissolved in 50 ml. of ethyl acetate and treated with 1.3 g. of dicyclohexylamine in 20 ml. of ethyl acetate. The product crystallizes from the solution and is filtered and dried to yield 2.65 g. of dicyclohexylamine salt; m.p. 181°–183°, s. 170°, $[\alpha]_D^{25}$ −62° (c, 1% in ethanol). Trituration with 15 ml. of hot acetonitrile followed by cooling gives 2.4 g. of colorless solid dicyclohexylamine salt; m.p. 183°–185°, s. 175°, $[\alpha]_D^{25}$ −65° (c, 1% in ethanol).

Anal. Calc'd. for $C_{15}H_{25}NO_5S.C_{12}H_{23}N$: C, 63.24; H, 9.44; N, 5.46; S, 6.25. Found: C, 63.22; H, 9.61; N, 5.41; S, 6.02.

Utilizing the procedure of Example 3, the 2.4 g. of dicylcohexylamine salt is converted to the acid by suspending in ethyl acetate, cooling in an ice-bath and treating with 30 ml. of 10% potassium bisulfate. The layers are separated and the aqueous phase is extracted with 25 ml. of ethyl acetate (4 x). After removal of the solvent, the material, which becomes partly crystalline on standing, is rubbed under 10 ml. of ether to complete crystallization, diluted with 20 ml. of hexane, rubbed, and cooled to yield 1.3 g. of 1-[D-3-(acetylthio)-2-methyl-1-oxopropyl]-cis-4-(1,1-dimethylethoxy)-L-proline as a colorless solid; m.p. 96°–98° (s. 93°), $[\alpha]_D^{25}$ −109° (c, 1% in ethanol).

Anal. Calc'd. for $C_{15}H_{25}NO_5S$: C, 54.36; H, 7.60; N, 4.23; S, 9.68. Found: C, 53.92; H, 7.73; N, 4.30; S, 9.29.

(e) cis-4-(1,1-Dimethylethoxy)-1-(D-3-mercapto-2-methyl-1-oxopropyl)-L-proline

The 1-[D-3-(acetylthio)-2-methyl-1-oxopropyl]-cis-4-(1,1-dimethylethoxy)-L-proline from part (d) (1.3 g., 0.0039 mole) is hydrolyzed with 2.6 ml. of concentrated ammonia hydroxide in 6 ml. of water to give 1.1 g. of a glass-like residue. On standing, seed crystals appear in the product. The material is covered with 8 ml. of ether, seeded, and rubbed. As the glass goes into solution, a crystalline solid gradually separates. After 2 hours at room temperature, 20 ml. of hexane is added and the mixture is cooled overnight under argon. The solvent is removed to yield 1.0 g. of colorless solid cis-4-(1,1-dimethylethoxy)-1-(D-3-mercapto-2-methyl-1-oxopropyl)-L-proline; m.p. 106°–108° (s, 103°), $[\alpha]_D^{25}$ −78° (c, 1% in ethanol).

Anal. Calc'd. for $C_{13}H_{23}NO_4S \cdot 0.25\ H_2O$ C, 53.12; H, 8.06; N, 4.77; S, 10.91. Found: C, 53.30; H, 8.28; N, 4.76; S, 10.70.

EXAMPLE 36

(cis)-1-[D-3-(Benzoylthio)-2-methyl-1-oxopropyl]-4-methylthio-L-propline

Interaction of equivalent quantities of (cis)-4-methylthio-L-proline (J. Amer. Chem. Soc., 79, 185 (1957)) and D-3-(benzoylthio)-2-methyl-propionyl chloride according to the procedure of Example 3 gives (cis)-1-[D-3-(benzoylthio)-2-methyl-1-oxopropyl]-4-methylthio-L-proline.

EXAMPLE 37

(trans)-1-[D-3-(Phenylacetyl)-2-methyl-1-oxopropyl]-4-methylthio-L-proline

Interaction of equivalent quantities of (trans)-4-methylthio-L-proline (J. Amer. Chem. Soc., 79, 185 (1957)) and D-3-(phenylacetylthio)-2-methylpropionyl chloride according to the procedure of Example 3 gives (trans)-1-[D-3-(phenylacetyl)-2-methyl-1-oxopropyl]-4-methylthio-L-proline.

EXAMPLE 38

(cis)-4-(4-Fluorophenoxy)-1-(D-3-mercapto-2-methyl-1-oxopropyl)-L-proline (a) (cis)-4-(4-Fluorophenoxy)-L-proline To a solution of 8.4 g. (0.024 mole) of N-carbobenzoxy-trans-4-hydroxy-L-proline, benzyl ester [Baer et al., Can. J. Biochem. & Phys., 37, 583 (1959)], 4.0 g. (0.036 mole) of 4-fluorophenol and 9.27 g. (0.036 mole) of triphenylphosphine in 75 ml. of dry tetrahydrofuran there is added dropwise over one hour 6.2 g. (0.036 mole) of diethylazodicarboxylate in 25 ml. of tetrahydrofuran. The solution is allowed to stir overnight at room temperature. The mixture is evaporated to dryness and 100 ml. of ether is added to the residue. A precipitate of triphenylphosphine and diethylazodicarboxylate is filtered off. Column chromatography (silica gel) separates out 8.1 g. of a mixture containing about 70% N-carbobenzoxy-cis-4-(4-fluorophenoxy)-L-proline, benzyl ester.

A solution of 7.5 g. of the above benzyl ester containing mixture is hydrogenated at 1 atmosphere (room temperature) with 0.8 g. of 10% Pd/C. A white precipitate forms during the reaction. After uptake of hydrogen ceases, the mixture is filtered and the filter cake leached with three 125 ml. portions of hot methanol. The methanol solution is evaporated to dryness to yield 3.2 g. of cis-4-(4-fluorophenoxy)-L-proline; m.p. 235°–236°.

Anal. Calc'd. for $C_{11}H_{12}FNO_3 \cdot \frac{1}{3} H_2O$: C, 57.14; H, 5.48; N, 6.06; F, 8.22. Found: C, 56.94; H, 5.19; N, 5.94; F, 7.97.

(b) 1-[D-3-(Acetylthio)-2-methyl-1-oxopropyl]-cis-4-(4-fluorophenoxy)-L-proline

To a suspension of 2.25 g. (0.01 mole) of cis-4-(4-fluorophenoxy)-L-proline in 125 ml. of dry pyridine at room temperature there is added 1.0 g. (0.01 mole) of triethylamine and 2 g. (0.011 mole) of D-3-(acetylthio)-2-methylpropionylchloride. After stirring overnight at room temperature the mixture is evaporated to dryness. The residue is taken up in water, covered with ether and acidified with 10% hydrochloric acid. The water layer is repeatedly extracted with ether, the ether layers are combined, washed with water, dried ($Na_2SO_4$) and evaporated to dryness to yield 3.9 g. of residue. The residue is chromatographed on 250 ml. of silica gel with ether to yield a fraction containing the desired product. The column is washed with methanol and the methanol washing is rechromatographed on a short silica gel column to yield more product. This procedure is repeated once more to yield a total of 1.2 g. of pure 1-[D-3-(acetylthio)-2-methyl-1-oxopropyl]-cis-4-(4-fluorophenoxy)-L-proline.

(c) (cis)-4-(4-Fluorophenoxy)-1-(D-3-mercapto-2-methyl-1-oxopropyl)-L-proline 1.2 g. of 1-[D-3-(acetylthio)-2-methyl-1-oxopropyl]-cis-4-(4-fluorophenoxy)-L-proline is dissolved in 25 ml. of methanol and treated with 5 ml. of concentrated ammonia under argon for 40 minutes. The volatiles are stripped off and the residue is covered with ethyl acetate. The water layer is acidified with 10% hydrochloric acid. The layers are separated and the acid layer is washed with ethyl acetate. The combined organic layers are stripped with water (2x), saturated sodium chloride solution (2x), and dried ($Na_2SO_4$). The solvent is stripped off to yield 1.1 g. of a solid foam residue of cis-4-(4-fluorophenoxy)-1-(D-3-mercapto-2-methyl-1-oxopropyl)-L-proline.

Anal. Calc'd. for $C_{15}H_{18}FNO_4 \cdot \frac{1}{2} H_2O$: C, 54.05; H, 5.70; N, 4.20; F, 5.70; S, 9.60. Found: C, 54.04; H, 5.71; N, 4.05; F, 5.40; S, 9.61.

Thin layer chromatography showed the product at $R_f$ 0.30 as detected by UV-light, SH reagent (yellow spot) and vanillin (yellow spot). $[\alpha]_D^{25}$ −80° (c, 1% in chloroform).

EXAMPLE 39

1-(3-Mercapto-1-oxopropyl)-cis-4-phenoxy-L-proline (a) (cis)-4-Phenoxy-L-proline Following the procedure of Example 38(a) but substituting an equivalent amount of phenol for the 4-fluorophenol one obtains (cis)-4-phenoxy-L-proline.

(b) 1-[3-(Acetylthio)-1-oxopropyl]-cis-4-phenoxy-L-proline

The (cis-4-phenoxy-L-proline is reacted with a solution of 3-acetylthiopropionyl chloride in the presence of sodium carbonate according to the procedure of Example 1 to yield 1-[3-(acetylthio)-1-oxopropyl]-cis-4-phenoxy-L-proline.

(c) 1-(3-Mercapto-1-oxopropyl)-cis-4-phenoxy-L-proline

Hydrolysis of 1-[3-(acetylthio)-1-oxopropyl]-cis-4-phenoxy-L-proline with an aqueous ammonia solution according to the procedure of Example 2 yields 1-(3-mercapto-1-oxopropyl)-cis-4-phenoxy-L-proline.

EXAMPLE 40

1-(D-3-Mercapto-2-methyl-1-oxopropyl)-cis-4-(4-methylbenzyloxy)-L-proline

Following the procedure of Example 38 but substituting an equivalent amount of 4-methylbenzyl alcohol for the 4-fluorophenol in part (a) one obtains 1-(D-3-mercapto-2-methyl-1-oxopropyl)-cis-4-(4-methylbenzyloxy)-L-proline.

EXAMPLE 41

1-(D-3-Mercapto-2-methyl-1-oxopropyl)-cis-4-phenethyloxy-L-proline

Following the procedure of Example 38 but substituting an equivalent amount of phenethyl alcohol for the 4-fluorophenol in part (a) one obtains 1-(D-3-mercapto-2-methyl-1-oxopropyl)-cis-4-phenethyloxy-L-proline.

EXAMPLE 42

1-(D-3-Mercapto-2-methyl-1-oxopropyl)-cis-4-(3-methylthiophenoxy)-L-proline

Following the procedure of Example 38 but substituting an equivalent amount of 3-methylthiophenol for the 4-fluorophenol in part (a) one obtains 1-(D-3-mercapto-2-methyl-1-oxopropyl)-cis-4-(3-methylthiophenoxy)-L-proline.

EXAMPLE 43

(cis)-4-(4-Chlorophenoxy)-1-(D-3-mercapto-2-methyl-1-oxopropyl)-L-proline

Following the procedure of Example 38 but substituting an equivalent amount of 4-chlorophenol for the 4-fluorophenyl in part (a) one obtains (cis)-4-(4-chlorophenoxy)-1-(D-3-mercapto-2-methyl-1-oxopropyl)-L-proline.

EXAMPLE 44

1-(2-Mercapto-1-oxoethyl)-cis-4-(4-methoxyphenoxy)-L-proline (a) (cis)-4-(4-Methoxyphenoxy)-L-proline Following the procedure of Example 38(a) but substituting an equivalent amount of 4-methoxyphenol for the 4-fluorophenol one obtains (cis)-4-(4-methoxyphenoxy)-L-proline.

(b) 1-[2-(Acetylthio)-1-oxoethyl]-cis-4-(4-methoxyphenoxy)-L-proline

The (cis)-4-(4-methoxyphenoxy)-L-proline is reacted with a solution of 2-acetylthioacetyl chloride according to the procedure of Example 1, part (d), to yield 1-[2-(acetylthio)-1-oxoethyl]-cis-4-(4-methoxyphenoxy)-L-proline.

(c) 1-(2-Mercapto-1-oxoethyl)-cis-4-(4-methoxyphenoxy)-L-proline

Hydrolysis of 1-[2-(acetylthio)-1-oxoethyl]-cis-4-(4-methoxyphenoxy)-L-proline with an aqueous ammonia solution according to the procedure of Example 2 yields 1-(2-mercapto-1-oxoethyl)-cis-4-(4-methoxyphenoxy)-L-proline.

EXAMPLE 45

(cis)-4-(4-Fluorophenylthio)-1-(D-3-mercapto-2-methyl-1-oxopropyl)-L-proline

Following the procedure of Example 38 but substituting an equivalent amount of 4-fluorophenylmercaptan for the 4-fluorophenol in part (a) one obtains (cis)-4-(4-fluorophenylthio)-1-(D-3-mercapto-2-methyl-1-oxopropyl)-L-proline.

EXAMPLE 46

(cis)-4-[(4-Fluorophenyl)thio]-1-(D-3-mercapto-2-methyl-1-oxopropyl)-L-proline, L-arginine (1:1) salt (a) (trans)-1-[D-3-(Benzoylthio)-2-methyl-1-oxopropyl]-4-hydroxy-L-proline, methyl ester (D)-3-(Benzoylthio)-2-methylpropanoic acid (56.05 g., 0.25 mole) is suspended in 62.5 ml. of toluene. The temperature falls to 15° and then 0.386 ml. of dimethylformamide are added. Then 32.7 g. (0.25 mole+10% excess) of thionyl chloride are added all at once with stirring. The temperature of the reaction mixture falls to 12° and the container used to measure the thionyl chloride is rinsed with 21.2 ml. of toluene which is then added to the reaction mixture. The temperature is raised gradually to 35° and maintained there for one hour. The reaction mixture is allowed to stir at room temperature overnight. The solvent and excess thionyl chloride are removed and the residue is treated twice with 100 ml. of toluene after which the toluene is removed to yield 63.4 g. of (D)-3-(benzoylthio)-2-methylpropanoic acid chloride.

L-4-Hydroxyproline (32.7 g., 0.25 mole) is dissolved in 250 ml. of water at pH 5.8. About 60 ml. of 10% sodium carbonate are added to bring the pH to 9.3. The solution is warmed to 30° and a toluene solution (75 ml.) containing 63 g. of (D)-3-(benzoylthio)-2-methylpropanoic acid chloride is added simultaneously with 10% aqueous sodium carbonate over one hour at 30° maintaining the pH at 9.0. The solution is stirred at pH 9.0 for 1.5 hours and the toluene layer is separated off. The aqueous layer is made strongly acid with concentrated HCl and the crystalline solid is filtered, washed with water, and air-dried to yield 71.4 g. of (trans)-1-[D-3-(benzoylthio)-2-methyl-1-oxopropyl]-4-hydroxy-L-proline; m.p. 195°–196°. Recrystallization from alcohol gives a m.p. of 196°–197°; $[\alpha]_D^{25}$ −139° (c=1, methanol).

Anal. Calc'd. for $C_{16}H_{19}NO_5S$: N, 4.15; C, 56.95; H, 5.67; S, 9.50. Found: N, 3.96; C, 56.56; H, 5.77; S, 9.50.

A solution of 33.7 g. (0.1 mole) of (trans)-1-[D-3-(benzoylthio)-2-methyl-1-oxopropyl]-4-hydroxy-L-proline and 500 mg. of p-toluenesulfonic acid in 1 l. of methanol is gently refluxed for about 18 hours. The methanol is removed to yield 37 g. of a viscous residue which is dissolved in 1400 ml. of ether. The ether solution is washed twice with 250 ml. of water, twice with 250 ml. of 5% sodium bicarbonate, and once with 250 ml. of brine and dried over $MgSO_4$. The ether is removed to yield 27.3 g. of crystalline product (after trituration with petroleum ether); m.p. 64°–65°. Recrystallization from ether yields (trans)-1-[D-3-benzoylthio)-2-methyl-1-oxopropyl]-4-hydroxy-L-proline, methyl ester; m.p. 65.5°–67°; $[\alpha]_D^{25}$ −158° (c=1, methanol).

Anal. Calc'd. for $C_{17}H_{21}NO_5S$: N, 3.99; C, 58.10; H, 6.02; S, 9.12. Found: N, 3.96; C, 57.96; H, 6.09; S, 9.11.

(b) N-(p-Fluorophenylthio)succinimide

Following the procedure of Y. Abe et al., Bull. Chem. Soc. Japan, Vol. 46, p. 1898 (1973), a suspension of 12.1 g. (90.8 mmole) of N-chlorosuccinimide in 500 ml. of benzene under nitrogen is treated with a solution of 9.7 g. (75.7 mmole) of p-fluorothiophenol dissolved in 90 ml. of benzene. A modest temperature rise is observed and the reaction mixture turns yellow-orange. After 75 minutes, the solution is cooled to 15° C. and treated with 9.19 g. (90.8 mmole) of triethylamine in 90 ml. of benzene added over a period of 25 minutes. The cooling bath is removed and the reaction is stirred for 45 minutes, then filtered and the organic solution is rinsed with three 150 ml. portions of water, brine and dried ($MgSO_4$). Removal of the solvents in vacuo yields 15.8 g. of crude product. Recrystallization from chloroform/hexane yields 11.6 g. of N-(p-fluorophenylthio)succinimide; m.p. 130°–138°.

(c) (cis)-1-[D-3-(Benzoylthio)-2-methyl-1-oxopropyl]-4-[(4-fluorophenyl)thio]-L-proline, methyl ester A solution of 11.0 g. (48.8 mmole) of N-(p-fluorophenylthio)succinimide in 200 ml. of benzene under an atmosphere of nitrogen is treated with 9.87 g. (48.8 mmole) of tri-n-butylphosphine in 25 ml. of benzene. The resulting dark solution is stirred for 10 minutes at room temperature and then 15.6 g. (44.4 mmole) of (trans)-1-[D-3-(benzoylthio)-2-methyl-1-oxopropyl]-4-hydroxy-L-proline, methyl ester is added. After stirring overnight at room temperature, the reaction mixture is diluted with 200 ml. of ether and rinsed with four 75 ml. portions of water, brine, and dried ($MgSO_4$). Removal of the solvents in vacuo gives 32.6 g. of crude product which is absorbed onto about 70 g. of silica gel and chromatographed on 450 g. of Baker silica gel packed and eluted with two liters of 1:1 $Et_2O$: hexanes, then eluted with two liters of 2:1, $Et_2O$: hexanes and finally with 100% ether. The best product containing fractions are pooled to afford 16.7 g. of (cis)-1-[D-3-(benzoylthio)-2-methyl-1-oxopropyl]4-[(4-fluorophenyl)thio]-L-proline, methyl ester as an oil; $[\alpha]_D^{25}$ −80.2 (c=1, chloroform).

(d) (cis)-4-[(4-Fluorophenyl)thio]-1-(D-3-mercapto-2-methyl-1-oxopropyl)-L-proline, L-arginine (1:1) salt A solution of 15.7 g. (34.0 mmole) of (cis)-1-[D-3-(benzoylthio)-2-methyl-1-oxopropyl]-4-[(4-fluorophenyl)thio]-L-proline, methyl ester in a mixture of 50 ml. of methanol and 150 ml. of tetrahydrofuran is cooled in an ice-bath under an atmosphere of nitrogen. The cold solution is treated with 71.4 ml. of 1 N aqueous sodium hydroxide added over a period of ten minutes. The cold bath is removed and the reaction is stirred at room temperature for 5.5 hours, then diluted with 300 ml. of water and washed with three 200 ml. portions of ether. The aqueous layer is cooled under nitrogen in an ice-bath and acidified to pH 1–2 with concentrated aqueous HCl, then extracted with three 200 ml. portions of ether. The combined organic extracts are rinsed with 200 ml. of water, brine and dried ($MgSO_4$). Removal of solvents in vacuo gives 11.7 g. of crude product. This material is dissolved in ether and treated with a solution of 5.66 g. (37.4 mmole) of 1-adamantanamine in methanol. Dilution with ether gives 15.2 g. of the adamantanamine salt which is recrystallized by dissolving in (1:1) chloroform:methanol and diluting with ether. This procedure yields 13.3 g. of the adamantanamine salt; m.p. 238°–240° (d). Two further recrystallizations from chloroform-methanol-ether give 10.6 g. of (cis)-4-[(4-fluorophenyl)thio]-1-(D-3-mercapto-2-methyl-1-oxopropyl)-L-proline, adamantanamine salt; m.p. 242°–243° (d); $[\alpha]_D^{25}$ −51.8° (c=0.5, methanol).

A sample of this adamantanamine salt is extracted with ethyl acetate from 1 N aqueous HCl to yield (cis)-4-[(4-fluorophenyl)thio]-1-(D-3-mercapto-2-methyl-1-oxopropyl)-L-proline; $[\alpha]_D^{25}$ −42.5° (c=1, absolute ethanol).

A rapidly stirred mixture of 20 ml. of 1 N HCl, 40 ml. of water and 60 ml. of ethyl acetate is treated with 8.0 g. (16.2 mmole) of (cis)-4-[(4-fluorophenyl)thio]-1-(D-3-mercapto-2-methyl-1-oxopropyl)-L-proline, adamantanamine salt added portionwise. The above process is carried out under nitrogen with ice bath cooling. The aqueous layer is extracted with two more 60 ml. portions of ethyl acetate and the combined organic extracts are rinsed with dilute aqueous HCl, water, and brine. After drying ($MgSO_4$), removal of the solvents in vacuo yields 5.78 g. of the liberated acid as a crude oil. The oil is dissolved in a mixture of 40 ml. of ethyl acetate and 10 ml. of ether. This solution is shaken in a separatory funnel with 2.68 g. (15.4 mmole) of L-arginine dissolved in 50 ml. of water. The aqueous layer is rinsed again with ether, put on a rotary evaporator for 15 minutes at low vacuum, and finally lyophilized overnight to yield 7.97 g. of (cis)-4-[(4-fluorophenyl)thio]1-(D-3-mercapto-2-methyl-1-oxopropyl)-L-proline, L-arginine salt (1:1); $[\alpha]_D^{25}$ −42.7 (c=1, water). Anal. Calc'd. for $C_{15}H_{18}FNO_3S_2 \cdot C_6H_{14}N_4O_2$ C, 47.08; H, 6.40; N, 13.08; S, 11.97 F, 3.55; SH, 6.17. Found: C, 47.21; H, 6.74; N, 13.28; S, 11.71 F, 3.38; SH, 5.98.

EXAMPLE 47

(cis)-4-[(4-Chlorophenyl)thio]-1-(D-3-mercapto-2-methyl-1-oxopropyl)-L-proline, L-arginine salt (1:1)

(a) N-(p-Chlorophenylthio)succinimide

Following the procedure of Y. Abe et al., supra, 4.3 g. (33.2 mmole) of N-chlorosuccinimide and 1800 ml. of benzene are treated with 40.0 g. (27.7 mmole) of p-chlorothiophenol dissolved in 360 ml. of benzene. After one hour, the resulting orange solution is cooled to 15° and 33.6 g. (33.2 mmole) of triethylamine in 360 ml. of benzene is added over a period of 15 minutes. The cooling bath is removed and the reaction is stirred at room temperature for an additional 45 minutes. The reaction mixture is then filtered and the organic solution is rinsed with three 500 ml. portions of water, 500 ml. of brine and dried ($MgSO_4$). Removal of the solvents in vacuo yields 55.1 g. of crude product. Trituration with 900 ml. of petroleum ether gives 42.0 g. of N-(p-chlorophenylthio)succinimide; m.p. 135°–152°.

(b) (cis)-1-[D-3-(Benzoylthio)-2-methyl-1-oxopropyl]-4-[(4-chlorophenyl)thio]-L-proline, methyl ester 12.6 g. (62.3 mmole) of tri-n-butylphosphine dissolved in 25 ml. of benzene is added to a solution of 15.1 g. (62.3 mmole) of N-(p-chlorophenylthio)succinimide in 250 ml. of benzene at room temperature under a nitrogen atmosphere. After ten minutes, 20 g. (56.9 mmole) of (trans)-1-[D-3-(benzoylthio)-2-methyl-1-oxopropyl]-4-hydroxy-L-proline, methyl ester is added and the reaction is kept at room temperature under nitrogen for two days. At the end of this time, the reaction mixture is diluted with 300 ml. of ether and rinsed with four 100 ml. portions of water, brine and dried ($MgSO_4$). Removal of the solvents in vacuo gives 46 g. of crude material which is absorbed onto about 75 g. of silica gel and chromatographed on a 450 g. Baker silica gel column. The column is packed and eluted with ether and the best product containing fractions are pooled to afford 27.2 g. of product. A small amount (0.48 g.) of the above is flash chromatographed on 25 g. of EM9385 silica gel packed and eluted first with methylene chloride followed by 18:1 methylene chloride:ethyl acetate to yield 0.28 g. of (cis)-1-[D-3-(benzoylthio)-2-methyl-1-oxo-propyl]-4-[(4-chlorophenyl)thio]-L-proline, methyl ester; $[\alpha]_D^{25}$ −86.6° (c=1, chloroform).

(c) (cis)-4-[(4-Chlorophenyl)thio]-1-(D-3-mercapto-2-methyl-1-oxopropyl)-L-proline, L-arginine salt (1:1)

A solution of 24.3 g. (50.8 mmole) of (cis)-1-[D-3-(benzoylthio)-2-methyl-1-oxopropyl]-4-[(4-chlorophenyl)thio]-L-proline, methyl ester in a mixture of 80 ml. of methanol and 220 ml. of tetrahydrofuran is cooled in an ice-bath under nitrogen and treated with 106 ml. of 1 N aqueous sodium hydroxide added over a period of 10 minutes. The cooling bath is removed and the reaction mixture is stirred at room temperature for 5.5 hours, then diluted with 500 ml. of water and rinsed with three 300 ml. portions of ether. The aqueous solution is cooled in an ice-bath under nitrogen and acidified to pH 1–2 with concentrated HCl and extracted three times with 500 ml. portions of ether. The combined ether extracts are rinsed with 400 ml. of water and brine, then dried (MgSO$_4$) and concentrated in vacuo to 18.2 g. of crude product. This material is dissolved in ether and treated with a solution of 8.5 g. (55.9 mmole) of 1-adamantanamine in methanol. The mixture is diluted to about 1 liter with ether, refrigerated for 1.5 hours and filtered to afford 20.1 g. of adamantanamine salt, m.p. 239°–242°. This material is dissolved in 1:1 chloroform: methanol and diluted with ether to give 15.3 g. of (cis)-4-[(4-chlorophenyl)thio]-1-(D-3-mercapto-2-methyl-1-oxopropyl)-L-proline, 1-adamantanamine salt; m.p. 240°–241° (d); $[\alpha]_D^{25}$ −55.4° (c=0.5, methanol).

A small sample of this adamantanamine salt (0.5 g., 0.98 mmole) is partitioned between aqueous HCl and ethyl acetate to yield the corresponding free acid; $[\alpha]_D^{25}$ −38.1° (c=1, absolute ethanol).

To a rapidly stirred mixture of 18.8 ml. of 1 N aqueous HCl, 30 ml. of water and 50 ml. of ethyl acetate there is added 8 g. (15.6 mmole) of the adamantanamine salt portionwise. The solution is kept cold in an ice-bath and blanketed with nitrogen. After all the solid has dissolved, the aqueous layer is extracted with two additional 50 ml. portions of ethyl acetate. The organic extracts are combined and rinsed with 30 ml. of 0.5 N aqueous HCl, 30 ml. of water and finally brine. The solution is dried (MgSO$_4$) and concentrated in vacuo to yield 5.6 g. of liberated acid. The acid is dissolved in a mixture of 50 ml. of ethyl acetate and 15 ml. of ether and shaken with a solution of 2.57 g. (14.8 mmole) of L-arginine dissolved in 65 ml. of water. The aqueous layer is rinsed with 50 ml. of ether and lyophilized overnight to yield 8.0 g. of (cis)-4-[(4-chlorophenyl)thio]-1-(D-3-mercapto-2-methyl-1-oxopropyl)-L-proline, L-arginine salt (1:1); $[\alpha]_D^{25}$ −44.3 (c=1, water).

Anal. Calc'd. for: $C_{15}H_{18}ClNO_3S_2 \cdot C_6H_{14}N_4O_2$ C, 45.09; H, 6.27; N, 12.52; S, 11.46; Cl, 6.34; SH, 5.91. Found: C, 45.34; ;1 H, 6.34; N, 12,57; S, 11.48; Cl, 6.12; SH, 5.44.

EXAMPLE 48

(cis)-1-(D-3-Mercapto-2-methyl-1-oxopropyl)-4-[(4-methylphenyl)thio]-L-proline, L-arginine salt (1:1)

(a) (cis)-1-[D-3-(Benzoylthio)-2-methyl-1-oxopropyl]-4-[(4-methylphenyl)thio]-L-proline, methyl ester A solution of 12.6 g. (62.5 mmole) of tri-n-butylphosphine in 20 ml. of benzene is added over a five minute period to a solution of 20 g. (56.8 mmole) of (trans)-1-[D-3-(benzoylthio)-2-methyl-1-oxopropyl]-4-hydroxy-L-proline, methyl ester and 15.4 g. (62.5 mmole) of p-tolyldisulfide in 120 ml. of benzene at room temperature under an atmosphere of nitrogen. After sitting overnight, the reaction mixture is diluted with 300 ml. of Et$_2$O and the organic solution is rinsed with three 100 ml. portions of water, brine and dried (MgSO$_4$). Concentration in vacuo gives 49 g. of crude product mixture. This material is absorbed onto 75 g. of Baker silica gel and applied to a 450 g. Baker silica gel column packed in 1:1, hexanes:ether. The column is eluted with 3 liters of 1:1 followed by 2 liters of 2:1, ether:hexanes and finally with 100% ether. Pooling of the best product containing fractions yields 14.6 g. of (cis)-1-[D-3-(benzoylthio)-2-methyl-1-oxopropyl]-4-[(4-methylphenyl)thio]-L-proline, methyl ester. A small sample is purified by flash chromatography on EM9385 silica gel using methylene chloride:ethyl acetate; $[\alpha]_D^{25}$ −70.8° (c=1, chloroform).

(b) (cis)-1-(D-3-Mercapto-2-methyl-1-oxopropyl)4-[(4-methylphenyl)thio]-L-proline, L-arginine salt (1:1)

An ice-cold solution of 13.0 g. (28.4 mmole) of (cis)-1-[D-3-(benzoylthio)-2-methyl-1-oxopropyl]4-[(4-methylphenyl)thio]-L-proline, methyl ester in a mixture of 40 ml. of methanol and 130 ml. of tetrahydrofuran is continually purged with nitrogen while 59.6 ml. of 1 N aqueous sodium hydroxide is added over a period of ten minutes. At the end of this time, the cooling bath is removed and the reaction mixture is stirred under nitrogen at room temperature for 5.5 hours. The reaction mixture is then diluted with 250 ml. of water and rinsed twice with 200 ml. portions of ether. The aqueous layer is next cooled in an ice-bath under nitrogen and acidified to pH 1–2 with concentrated HCl and extracted with three 200 ml. portions of ether. The combined organic extract is rinsed with 200 ml. of water and brine, dried (MgSO$_4$) and concentrated in vacuo to 10.6 g. of colorless oil which is nearly homogeneous by tlc. The product is dissolved in ether and treated with 4.72 g. (31.2 mmole) of 1-adamantanamine dissolved in 20 ml. of methanol. Precipitation is rapid and the solution is diluted with ether to about 700 ml. total volume and the salt is collected. Retrituration with warm methanol-ether gives 12.4 g. of adamantanamine salt, m.p. 237°–240° (d). This salt is recrystallized by dissolving in a minimum amount of 1:1 chloroform:methanol and diluting with ether. After 10 minutes at room temperature, the solid is collected and dried to yield 8.2 g. of adamantanamine salt; m.p. 240°–241° (d); $[\alpha]_D^{25}$ −58.0° (c=0.5, methanol).

A small sample of this adamantanamine salt is partitioned between aqueous HCl and ethyl acetate to yield (cis)-1-(D-3-mercapto-2-methyl-1-oxopropyl)-4-[(4-methylphenyl)thio]-L-proline as an oil; $[\alpha]_D^{25}$ −45.1° (c=1, absolute ethanol).

To a mixture of 17.1 ml. of aqueous 1 N HCl, 30 ml. of water, and 50 ml. of ethyl acetate, there is added 7.0 g. (14.3 mmole) of the above adamantanamine salt in several portions. During the addition the solution is cooled in an ice-bath and kept blanketed with argon. When all the salt dissolves, the layers are separated and the ethyl acetate layer is combined with two further 50 ml. extractions of the aqueous solution. The combined ethyl acetate extract is rinsed with dilute HCl, water and brine, dried (MgSO$_4$) and concentrated in vacuo to give the liberated acid. The acid is dissolved in a mixture of 40 ml. of ethyl acetate and 10 ml. of ether and shaken with a solution of 2.37 g. (13.6 mmole) of L-arginine in 50 ml. of water. The aqueous layer is rinsed with 50 ml. of ether and then lyophilized to yield (cis)-1-(D-3-mercapto-2-methyl-1-oxopropyl)-4-[(4-methylphenyl)thio]-L-proline, L-arginine salt (1:1); $[\alpha]_D^{25}$ −45.3° (c=1, water).

Anal. Calc'd. for $C_{16}H_{21}NO_3S_2 \cdot C_6H_{14}N_4O_2$ C, 49.69; H, 7.01; N, 13.17; S, 12.06; SH, 6.22. Found: C, 49.55; H, 7.04; N, 13.28; S, 11.73; SH, 5.97.

EXAMPLE 49

(cis)-1-(D-3-Mercapto-2-methyl-1-oxopropyl)-4-[(4-methoxyphenyl)thio]-L-proline, L-arginine salt (1:1)

(a) N-(p-Methoxyphenylthio)succinimide

A mixture of 17.1 g. (128 mmole) of N-chlorosuccinimide and 700 ml. of benzene is treated with 15 g. (107 mmole) of p-methoxythiophenol dissolved in 125 ml. of benzene. After 75 minutes, the resulting orange solution is cooled to 15° and 13.0 g. (128 mmole) of triethylamine in 125 ml. of benzene is added over a period of 25 minutes. The cooling bath is removed and the reaction is stirred at room temperature for an additional 45 minutes. The reaction mixture is then filtered and the organic solution is rinsed with three 200 ml. portions of water, 200 ml. of brine and dried (MgSO$_4$). Removal of the solvents in vacuo gives 27.0 g. of crude product. Recrystallization from chloroform-hexane gives 21.2 g. of N-(p-methoxyphenylthio)succinimide; m.p. 100°–106°.

(b) (cis)-1-[D-3-(Benzoylthio)-2-methyl-1-oxopropyl]-4-[(4-methoxy)phenylthio]-L-proline, methyl ester To a solution of 14.0 g. (59.1 mmole) of N-(p-methoxyphenylthio)succinimide in 250 ml. of benzene at room temperature under nitrogen there is added 12.0 g. (59.1 mmole) of tri-n-butylphosphine dissolved in 25 ml. of benzene. After ten minutes, 18.9 g. (53.7 mmole) of (trans)-1-[D-3-(benzoylthio)-2-methyl-1-oxopropyl]-4-hydroxy-L-proline, methyl ester is added and the reaction is left at room temperature under nitrogen for 25 hours. At the end of this time, the reaction mixture is diluted with 300 ml. of ether and rinsed with three 100 ml. portions of water, brine and dried (MgSO$_4$). Removal of the solvents in vacuo gives 40 g. of crude material which is absorbed onto about 80 g. of silica gel and chromatographed on a 450 Baker silica gel column. The column is packed and eluted with a 4:1 mixture of hexane:ether, followed by 2:1 hexane:ether, and finally 1:1 hexane:ether. The best product containing fractions are pooled to afford 20.6 g. of product. A small sample (0.5 g.) of product is further purified by flash chromatograph on 50 g. of EM9385 silica gel packed and eluted with ether. The best product containing fractions are pooled and yield 480 mg. of (cis)-1-[D-3-(benzoylthio)-2-methyl-1-oxopropyl]-4-[(4-methoxyphenyl)thio]-L-proline, methyl ester; $[\alpha]_D^{25}$ 31 66.9° (c=1, chloroform).

(c) (cis)-1-(D-3-Mercapto-2-methyl-1-oxopropyl)-4-[(4-methoxyphenyl)thio]-L-proline, L-arginine salt (1:1)

A solution of 20.1 g. (42.4 mmole) of (cis)-1-[D-3-(benzoylthio)-2-methyl-1-oxopropyl]-4-[(4-methoxyphenyl)thio]-L-proline, methyl ester in a mixture of 70 ml. of methanol and 200 ml. of tetrahydrofuran is cooled in an ice bath under nitrogen and treated with 89 ml. of 1 N aqueous sodium hydroxide over a period of ten minutes. The cooling bath is removed and the reaction mixture is stirred at ambient temperature for 5.5 hours, then diluted with 500 ml. of water and rinsed with three 300 ml. portions of ether. The aqueous solution is cooled in an ice-bath under nitrogen and acidified to pH 1 with concentrated HCl and saturated with three 500 ml. portions of ether. The combined ether extracts are rinsed with 400 ml. of water and brine, dried (MgSO$_4$), and concentrated in vacuo to give 14.8 g. of crude product. This material is dissolved in ether and treated with a solution of 6.34 g. (42 mmole) of 1-adamantanamine in methanol. The mixture is diluted to about 1 liter with ether, left at room temperature for ten minutes and filtered to give 17.8 g. of adamantanamine salt; m.p. 235°–236° (dec.). This material is dissolved in 1:1, chloroform:methanol with gentle heating, and diluted with ether. This recrystallization procedure is repeated twice more to give 12.2 g. of (cis)-1-(D-3-mercapto-2-methyl-1-oxopropyl)-4-[(4-methoxyphenyl)thio]-L-proline, 1-adamantanamine salt; m.p. 237°–239° (d.); $[\alpha]_D^{25}$ −52.8°; (c=0.5, methanol).

A small sample of this 1-adamantanamine salt (500 mg., 0.99 mmole) is partitioned between aqueous HCl and ethyl acetate to yield the corresponding free acid; $[\alpha]_D^{25}$ −36.8° (C=1, absolute ethanol).

To a rapidly stirred mixture of 27.2 ml. of 1 N aqueous HCl, 45 ml. of water and 75 ml. of ethyl acetate is added portionwise 11.5 g. (22.7 mmole) of the above 1-adamantanamine salt. The solution is kept cold in an ice-bath and blanketed with nitrogen. After all the solid has dissolved, the aqueous layer is extracted with two further 75 ml. portions of ethyl acetate. The organic extracts are combined and rinsed with 50 ml. of 0.5 N aqueous HCl, 50 ml. of water, and finally brine. The solution is dried (MgSO$_4$) and concentrated in vacuo to yield 8.2 g. of liberated acid. The acid is dissolved in a mixture of 75 ml. of ethyl acetate and 20 ml. of ether and shaken with a solution of 3.76 g. (21.6 mmole) of L-arginine dissolved in 100 ml. of water. The aqueous layer is rinsed with 75 ml. of ether and lyophilized overnight to yield 11.2 g. of (cis)-1-(D-3-mercapto-2-methyl-1-oxopropyl)-4-[(4-methoxyphenyl)thio]-L-proline, L-arginine salt (1:1); $[\alpha]_D^{25}$ −46.0° (c=1, water).

Anal. Calc'd. for $C_{16}H_{21}NO_4S_2 \cdot C_6H_{14}N_4O_2$ C, 47.93; H, 6.84; N, 12.70; S, 11.63; SH, 6.00. Found: C, 47.99, H, 6.61, N, 12.66; S, 11.62; SH, 6.00.

EXAMPLE 50

(cis)-4-([1,1'-Biphenyl]-4-yloxy)-1-(D-3-mercapto-2-methyl-1-oxopropyl))-L-proline (a) (cis)-4-([1,1'-Biphenyl]-4-yloxy)-1-[(phenylmethoxy)carbonyl]-L-proline, phenylmethyl ester Diethylazodicarboxylate (13.3 g., 0.075 mole) is added dropwise over 30 minutes to a solution of 17.5 g. (0.05 mole) of N-carbobenzyloxy-trans-4-hydroxy-L-proline, benzyl ester, 12.75 g. (0.075 mole) of p-phenylphenol, and 19.32 g. (0.075 mole) of triphenylphosphine in 400 ml. of dry tetrahydrofuran. After stirring overnight at room temperature, the solvent is removed under vacuum and 400 ml. of ether is added. The resulting diethylazodicarboxylate precipitate is filtered off. The solution is concentrated to about 150 ml. and allowed to stand for about 30 minutes and the resulting triphenylphosphine precipitate is filtered off. The action of the air during filtration initiates crystallization in the filter flank. After standing at room temperature with occasional stirring, the precipitate is filtered off to yield 22.5 g. of crude product. Recrystallization of 2 g. from ethyl acetate yields 1.5 g. of (cis)-4-([1,1'-biphenyl]-4-yloxy)-1-[(phenylmethoxy)carbonyl]L-proline, phenylmethyl ester; m.p. 136°–137.5°.

Anal. Calc'd. for $C_{32}H_{29}NO_5$: C, 75.72; H, 5.76; N, 2.76. Found: C, 75.36; H, 5.48; N, 2.52.

(b) (cis)-1-[D-3-(Acetylthio)-2-methyl-1-oxopropyl]-4-([1,1'-biphenyl)-4-yloxy)-L-proline The benzyl ester product from part (a) (4.8 g., 9.47 mmole) and 0.5 g. 10% palladium/carbon catalyst are hydrogenated in 100 ml. of absolute ethanol overnight at atmospheric pressure. The mixture containing the precipitated product and the palladium/carbon is filtered out and taken up in pyridine. D-3-(Acetylthio)-2-methylpropionyl chloride (7.3 g., 40.3 mmole) is added and the mixture is stirred overnight. The catalyst is filtered off, the pyridine is evaporated, and the residue (0.8 g.) is crystallized from toluene:acetic acid (9:1), toluene, and methanol to yield 0.7 g. of (cis)-1-[D-3-(acetylthio)-2-methyl-1-oxopropyl]-4-([1,1'-biphenyl]-4-yloxy)-L-proline; m.p. 188°–190°.

Anal. Calc'd. for $C_{23}H_{25}NO_5S \cdot H_2O$: C, 62.00; H, 6.11; N, 3.14; S, 7.20. Found: C, 62.26; H, 6.27; N, 2.99; S, 7.16.

(c) (cis)-4-([1,1'-Biphenyl]-4-yloxy)-1-(D-3-mercapto-2-methyl-1-oxopropyl)-L-proline The product from part (b) in 8 ml. of methanol is treated with 4 ml. of concentrated ammonia under argon for one hour. The methanol is stripped off and the aqueous solution is washed with ethyl acetate. The aqueous solution is acidified and extracted with ethyl acetate which is, in turn, washed with water (twice), saturated sodium chloride, and dried ($Na_2SO_4$). The solution is concentrated and allowed to stand. The product crystallizes out and is filtered off, washed as a slurry with methanol, filtered off and dried under vacuum to yield 0.11 g. of (cis)-4-([1,1'-biphenyl]-4-yloxy)-1-(D-3-mercapto-2-methyl-1-oxopropyl)-L-proline; m.p. 188°–189°, $[\alpha]_D^{25}$ −71.1° (c, 0.4% in chloroform).

Anal. Calc'd. for $C_{21}H_{23}NO_4S \cdot \frac{1}{4} H_2O$: C, 64.67; H, 6.07; N, 3.59; S, 8.22. Found: C, 64.87; H, 5.92; N, 3.50; S, 8.42.

EXAMPLE 51

(cis)-4-([1,1'-Biphenyl]-4-yloxy)-1-(3-mercapto-1-oxopropyl)-L-proline (a) (cis)-4-([1,1'-Biphenyl]-4-yloxy)-1-(3-acetyl-thio-1-oxopropyl)-L-proline Following the procedure of Example 50 (b) but employing 3-acetylthiopropionyl chloride one obtains (cis)-4-([1,1'-biphenyl]-4-yloxy)-1-(3-acetylthio-1-oxopropyl)-L-proline.

(b) (cis)-4-([1,1'-Biphenyl]-4-yloxy)-1-(3-mercapto-1-oxopropyl)-L-proline

The product from part (a) is treated with concentrated ammonia according to the procedure of Example 50 (c) to yield (cis)-4-([1,1'-biphenyl]-4-yloxy)-1-(3-mercapto-1-oxopropyl)-L-proline.

EXAMPLE 52

(cis)-4-([1,1'-Biphenyl]-4-ylthio)-1-(D-3-mercapto-2-methyl-1-oxopropyl)-L-proline Following the procedure of Example 50 but substituting an equivalent anount of p-phenylphenylmercaptan for the p-phenylphenol in part (a), one obtains (cis)-4-([1,1'-biphenyl]-4-ylthio)-1-(D-3-mercapto-2-methyl-1-oxopropyl)-L-proline.

EXAMPLE 53

(cis)-1-(D-3-Mercapto-2-methyl-1-oxopropyl)-4-(2-naphthalenyloxy)-L-proline (a) (cis)-1-[(Phenylmethoxy)carbonyl]-4-(2-naphthalenyloxy)-L-proline, phenylmethyl ester Diethylazodicarboxylate (8.82 g., 0.05 mole) dissolved in 10 ml. of tetrahydrofuran is added dropwise over 10 minutes to a stirred solution of 12 g. (0.0338 mole) of N-carbobenzyloxy-trans-4-hydroxy-L-proline, benzyl ester, 7.3 g. (0.05 mole) of 2-hydroxynaphthalene, and 13.3 g. (0.05 mole) of triphenylphosphine in 100 ml. of tetrahydrofuran. After stirring overnight, the solvent is evaporated and the residue taken up in 400 ml. of ethyl ether. Material which crystallizes out overnight at 0° is filtered off, the filtrate is washed with 10% sodium hydroxide (twice), water (twice), dried ($Na_2SO_4$), and evaporated. The residue is stirred in 100 ml. of ethyl ether for one hour, filtered, and flash chromatographed on 600 ml. LP-1 silica gel eluted with ethyl ether/pentane. Pure fractions by thin layer chromatography (silica gel, ethyl ether, $R_f$ 0.9) are combined and evaporated to give 12.7 g. of (cis)-1-[(phenylmethoxy)carbonyl]-4-(2-naphthalenyloxy)-L-proline, phenylmethyl ester as an oil.

(b) (cis)-4-(2-Naphthalenyloxy)-L-proline

The benzyl ester product from part (a) (11 g., 0.0228 mole) and 1 g. of 10% palladium/carbon catalyst are hydrogenated in 200 ml. of absolute ethanol in a Parr bottle overnight at 20 psi. The catalyst and precipitated product are filtered off. The filter cake is leached twice with hot methanol. The combined methanol leachates are evaporated to give 1.6 g. of (cis)-4-(2-naphthalenyloxy)-L-proline; m.p. 258°–260° (dec.), $[\alpha]_{26}^D$ −14.3° [1, water, methanol, sodium hydroxide]. The ethanol filtrate is evaporated to yield an additional 3.0 g. of product.

(c) (cis)-1-[D-3-(Acetylthio)-2-methyl-1-oxopropyl]-4-(2-naphthalenyloxy)-L-proline D-3-Acetylthio-2-methylpropionyl chloride (0.3 g., 1.6 mmole) is added to 0.3 g. (1.16 mmole) of (cis)-4-(2-naphthalenyloxy)-L-proline from part (b) suspended in 4 ml. of dry pyridine. A clear solution results. After stirring for two hours another 0.15 g. of D-3-acetylthio-2-methylpropionyl chloride is added and the mixture is stirred for an additional hour. The mixture is evaporated to dryness and the residue partitioned between ethyl acetate and 5% hydrochloric acid. The ethyl acetate solution is washed with water (twice) and saturated sodium chloride solution, and then dried ($Na_2SO_4$). The ethyl acetate solution is evaporated to dryness and the residue is triturated with ether. The ether insoluble material is collected, taken up in about 20 ml. of ethyl acetate, filtered through celite and stripped to yield 0.2 g. of (cis)-1-[D-3-(acetylthio-2-methyl-1-oxopropyl]-4-(2-naphthalenyloxy)-L-proline.

(d) (cis)-1-(D-3-Mercapto-2-methyl-1-oxopropyl)-4-(2-naphthalenyloxy)-L-proline

The 0.2 g. of product from part (c) is dissolved in 2 ml. of methanol and treated with 2 ml. of concentrated ammonia under argon for 90 minutes. The methanol is removed under vacuum and the residual aqueous solution is washed with ethyl acetate. The aqueous layer is acidified and extracted with ethyl acetate which is, in turn, washed with water (twice) and saturated sodium chloride solution, dried ($Na_2SO_4$), and stripped to yield 0.11 g. of (cis)-1-(D-3-mercapto-2-methyl-1-oxopropyl)-4-(2-naphthalenyloxy)-L-proline as a white foam, $[\alpha]_D^{25}$ −97.7° (c, 0.3% in chloroform).

Anal. Calc'd. for $C_{19}H_{21}NO_4S.\frac{3}{8}H_2O$: C, 61.43; H, 6.05; N, 3.77; S, 8.63. Found: C, 61.52; H, 5.87; N, 3.51; S, 8.64.

EXAMPLE 54

(cis)-1-(D-3-Mercapto-2-methyl-1-oxopropyl)-4-(1-naphthalenyloxy)-L-proline

Following the procedure of Example 53 but substituting 1-hydroxynaphthalene for the 2-hydroxynaphthalene in part (a), one obtains (cis)-1-(D-3-mercapto-2-methyl-1-oxopropyl)-4-(1-naphthalenyloxy)-L-proline.

EXAMPLE 55

(cis)-1-(D-3-Mercapto-2-methyl-1-oxopropyl)-4-(2-naphthalenylthio)-L-proline

Following the procedure of Example 53 but substituting naphthalene-2-mercaptan for the 2-hydroxynaphthalene in part (a), one obtains (cis)-1-(D-3-mercapto-2-methyl-1-oxopropyl)-4-(2-naphthalenylthio)-L-proline.

EXAMPLE 56

(cis)-1-(D-3-Mercapto-2-methyl-1-oxopropyl)-4-(2-naphthalenyloxy)-L-proline, 1-adamantanamine salt (1:1)

(a) (cis)-1-[D-3-(Benzoylthio)-2-methyl-1-oxopropyl]-4-(2-naphthalenyloxy)-L-proline, methyl ester To a solution of 0.733 g. (5.07 mmole) of 2-naphthol, 1.328 g. (5.07 mmole) of triphenylphosphine, 1.186 g. (3.38 mole) of (trans)-1-[D-3-(benzoylthio)-2-methyl-1-oxopropyl]-4-hydroxy-L-proline, methyl ester in 10 ml. of dry tetrahydrofuran, there is added dropwise a solution of 0.882 g. of diethylazodicarboxylate dissolved in 2 ml. of dry tetrahydrofuran. After stirring for three days, the solution is absorbed on Baker silica and pumped free of solvent. This material is then flash chromatographed using peteroleum ether-ether mixtures (80/20 to 40/60) to yield 1.0 g. of (cis)-1-[D-3-(benzoylthio)-2-methyl-1-oxopropyl]-4-(2-naphthalenyloxy)-L-proline, methyl ester.

(b) (cis)-1-(D-3-Mercapto-2-methyl-1-oxopropyl)-4-(2-naphthalenyloxy)-L-proline, 1-adamantanamine salt (1:1)

The total quantity of (cis)-1-[D-3-(benzoylthio)-2-methyl-1-oxopropyl]-4-2-(naphthalenyloxy)-L-proline, methyl ester is stirred at room temperature with a mixture of 25 ml. methanol/6 ml. 1 N sodium hydroxide under a blanket of nitrogen. The solvent is evaporated, 50 ml. of water is added and the residue is extracted with three 5 ml. portions of ethyl acetate. Evaporation of the dried solvent yields an oil, which on standing begins to crystallize. Treatment of an ethyl acetate solution of this product with a clear, saturated ethyl acetate solution of 1-adamantanamine yields the desired salt product. Crystallization of the solid from methanol-ethyl ether yields 0.5 g. of (cis)-1-(D-3-mercapto-2-methyl-1-oxopropyl)-4-(2-naphthalenyloxy)-L-proline, 1-adamantanamine salt (1:1); m.p. 244°–246° (slow heating).

Anal. Calc'd. for $C_{19}H_{21}NO_4S.C_{10}H_{17}N$ C, 68.20; H, 7.50; N, 5.49. Found: C, 68.16; H, 7.53; N, 5.40.

EXAMPLE 57

(cis)-1-(D-3-Mercapto-2-methyl-1-oxopropyl)-4-(2-naphthalenylthio)-L-proline (a) N-Carbobenzyloxy-(cis)-4-(2-naphthalenylthio)-L-proline, methyl ester The sodium salt of 3.8 g. (0.024 mole) of 2-naphthalenethiol [prepared in 30 ml. of ethanol employing 0.6 g. (0.026 g. atom) of sodium metal] is reacted with 5.0 g. (0.0115 mole) of N-carbobenzyloxy-(trans)-4-tosyloxy-L-proline, methyl ester [J. Am. Chem. Soc., 79, 191 (1957)] to give 7.1 g. of a partly solid light yellow product. Stirring with 65 ml. of methanol left 0.6 g. of undissolved colorless solid. Following evaporation of the methanol, 6.0 g. of yellow oil N-carbobenzyloxy-(cis)-4-(2-naphthalenylthio)-L-proline, methyl ester are obtained.

(b) N-Carbobenzyloxy-(cis)-4-(2-naphthalenylthio)-L-proline 6.0 g. (0.0115 mole) of the above methyl ester are saponified with 13 ml. (0.026 mole) of 2 N sodium hydroxide in 55 ml. of methanol to give 5.4 g. of a pale yellow-orange viscous oil. The material is taken up in 100 ml. of ether, stirred for 20 minutes with a solution of 1.5 g. of sodium bicarbonate in 50 ml. of water, and the layers are separated. After extracting the ether layer with 50 ml. of water, the combined aqueous phases are layered with 50 ml. of ether, stirred, and acidified with 20 ml. of 1 N HCl. The layers are separated, the aqueous phase is extracted with ether (2×50 ml.), the combined organic layers are dried ($MgSO_4$), and the solvent evaporated to yield 3.4 g. of a nearly colorless brittle residue. The latter is dissolved in 15 ml. of ethanol and treated with 0.9 g. of cyclohexylamine and diluted with 150 ml. of ether. On seeding, 2.7 g. of crystalline cyclohexylamine salt separates; m.p. 126°–128° (s. 115°); $[\alpha]_D^{25}$ −20° (c=1.0, ethanol).

Anal. Calc'd. for $C_{23}H_{21}NO_4S.C_6H_{13}N.0.25\ H_2O$ C, 68.14; H, 6.80; N, 5.48; S, 6.27. Found: C, 68.04; H, 6.73; N, 5.46; S, 6.11.

2.6 g. of this cyclohexylamine salt is suspended in ethyl acetate, stirred and treated with 1 N HCl. The layers are separated and the aqueous phase is extracted with additional ethyl acetate. The combined organic layers are dried ($MgSO_4$) and the solvent evaporated to give 2.1 g. of N-carbobenzyloxy-(cis)-4-(2-naphthalenylthio)-L-proline as a colorless glass-like residue.

(c) (cis)-4-(2-Naphthalenylthio)-L-proline hydrobromide

N-Carbobenzyloxy-(cis)-4-(2-naphthalenylthio)-L-proline (2.1 g., 0.0052 mole) is treated with 14 ml. of hydrogen bromide in acetic acid (30–32%) over a period of 1.25 hours to give 1.3 g. of pale tan (cis)-4-(2-naphthalenylthio)-L-proline hydrobromide; m.p. 180°–183° (s. 167°); $[\alpha]_D^{25}$ −4° (c=1.0, methanol).

Anal. Calc'd. for $C_{15}H_{15}NO_2S.HBr$ C, 50.85; H, 4.55; N, 3.95; Br, 22.56. Found: C, 49.43; H, 4.48; N, 3.92; Br, 23.30.

(d) (cis)-1-[D-3-(Acetylthio)-2-methyl-1-oxopropyl]-4-(2-naphthalenylthio)-L-proline Interaction of 1.3 g. (0.0037 mole) of (cis)-4-(2-naphthalenylthio)-L-proline hydrobromide and 0.75 g. (0.0042 mole) of D-3-acetylthio-2-methylpropionyl chloride in 20 ml. of water in the presence of sodium carbonate yields 1.5 g. of viscous pale yellow product. The dicyclohexylamine salt (prepared in 10 ml. of ethyl acetate employing 0.7 g. of dicyclohexylamine) weighs 0.5 g.; m.p. 155°–158° (s. 153°). Evaporation of the filtrate gives a brittle amorphous residue which is crystallized from 7 ml. of acetonitrile to yield 1.05 g. of additional salt; m.p. 156°–159° (s. 154°). Following trituration of the combined crops with 7 ml. of acetonitrile and cooling for 30 minutes, 1.45 g. of colorless solid (cis)-1-[D-3-(acetylthio)-2-methyl-1-oxopropyl]-4-(2-naphthalenylthio)-L-proline, dicyclohexylamine salt; m.p. 157°–159° (s. 155°); $[\alpha]_D^{25}$ $-46°$ (c=1.0, ethanol).

Anal. Calc'd. for $C_{21}H_{23}NO_4S_2 \cdot C_{12}H_{23}N \cdot 0.5\ H_2O$: C, 65.20; H, 7.79; N, 4.61; S, 10.55. Found: C, 65.03; H, 7.58; N, 4.42; S, 10.52.

1.4 g. of this dicyclohexylamine salt is treated with 20 ml. of 10% potassium bisulfate and extracted into ethyl acetate as described in Example 1 to yield 0.9 g. of colorless brittle foam like (cis)-1-[D-3-(acetylthio)-2-methyl-1-oxopropyl]-4-(2-naphthalenylthio)-L-proline; $[\alpha]_D^{25}$ $-57°$ (c=1.0, ethanol).

(e) (cis)-1-(D-3-Mercapto-2-methyl-1-oxopropyl)-4-(2-naphthalenylthio)-L-proline The (cis)-1-[D-3-(acetylthio)-2-methyl-1-oxopropyl]-4-(2-naphthalenylthio)-L-proline (0.9 g., 0.0022 mole) is treated with 1.8 ml. of concentrated ammonia in 4.5 ml. of water to give 0.8 g. of colorless feathery amorphous solid (cis)-1-(D-3-mercapto-2-methyl-1-oxopropyl)-4-(2-naphthalenylthio)-L-proline; m.p. 48°–51° (s. 39°); $[\alpha]_D^{25}$ $-19°$ (c=1.0, ethanol).

Anal. Calc'd. for $C_{19}H_{21}NO_3S_2 \cdot 0.75H_2O$ C, 58.66; H, 5.83; N, 3.60; S, 16.48. Found: C, 58.47; H, 5.67; N, 3.62; S, 16.49.

EXAMPLE 58

1-(D-3-Mercapto-2-methyl-1-oxopropyl)-cis-4-phenylthio-L-proline (a) N-Carbobenzyloxy-cis-4-phenylthio-L-proline, methyl ester Sodium metal (0.85 g., 0.037 mole) is dissolved in 40 ml. of absolute ethanol. To this there is added with stirring 3.7 ml. (0.036 mole) of thiophenol followed by 7.5 g. (0.017 mole) of N-carbobenzyloxy-trans-4-tosyloxy-L-proline, methyl ester [J. Am. Chem. Soc., 79, 191 (1957)]. The latter gradually goes into solution but soon thereafter a solid product separates. After stirring for 4 hours and standing overnight at room temperature, the bulk of the ethanol is removed on a rotary evaporator. The mostly solid residue is stirred with 120 ml. of dichloromethane and 60 ml. of water. The layers are separated (some methanol is added to help break up emulsions) and the aqueous phase is extracted with additional dichloromethane (2×60 ml.). The combined organic phase are washed with 100 ml. of saturated sodium chloride solution, dried (MgSO₄), and the solvent evaporated to give 6.5 g. (100%) of N-carbobenzyloxy-cis-4-phenylthio-L-proline, methyl ester as a pale yellow viscous oil.

(b) N-Carbobenzyloxy-cis-4-phenylthio-L-proline

The methyl ester product from part (a) (6.5 g., 0.017 mole) is dissolved in 55 ml. of methanol, treated portionwise at −1° to 4° with 13 ml. (0.026 mole) of 2 N sodium hydroxide, stirred at 0° for one hour, and kept at room temperature for approximately 16 hours. After removing about half of the solvent on a rotary evaporator, the cooled solution is diluted with 100 ml. of water, washed with 60 ml. of ether (wash discarded), layered over with 70 ml. of ethyl acetate, stirred, cooled, and acidified with 4.8 ml. of 1:1 hydrochloric acid. After separating, the aqueous phase is extracted with additional ethyl acetate (3×40 ml.) and the combined organic layers are dried (MgSO₄) and evaporated to give 5.9 g. of a light yellow viscous oil. The latter is dissolved in 30 ml. of ethanol, treated with 1.9 g. of cyclohexylamine in 3 ml. of ethanol and diluted to 330 ml. with ether. On seeding, the crystalline cyclohexylamine salt separates. The latter, after cooling for approximately 16 hours, weighs 5.3 g.; m.p. 148°–151° (s. 135°). This material is combined with 1.5 g. of identical product from a previous experiment, stirred with 200 ml. of boiling acetonitrile, and cooled to yield 6.3 g. of colorless cyclohexylamine salt; m.p. 152°–155° (s. 137°) $[\alpha]_D^{26}$ $-24°$ (c, 1% in ethanol).

Anal. Calc'd. for $C_{19}H_{19}NO_4S \cdot C_6H_{13}N$ C, 65.76; H, 7.06; N, 6.14; S, 7.02. Found: C, 65.73; H, 6.88; N, 6.09; S, 6.67.

This cyclohexylamine salt is suspended in 25 ml. of ethyl acetate, stirred, and treated with 25 ml. of N hydrochloric acid. When two clear layers are obtained, they are separated and the aqueous phase is extracted with additional ethyl acetate (3×25 ml.). The combined organic layers are dried (MgSO₄) and the solvent evaporated to give 5.0 g. (65%) of N-carbobenzyloxy-cis-4-phenylthio-L-proline as a nearly colorless, very viscous syrup.

(c) (cis)-4-Phenylthio-L-proline hydrobromide

N-Carbobenzyloxy-cis-4-phenylthio-L-proline (4.9 g., 0.014 mole) is treated with 25 ml. of hydrogen bromide in acetic acid (30–32%), stoppered loosely, and stirred magnetically. After one hour the orange-yellow solution is diluted to 250 ml. with ether to precipitate the product as a heavy oil which gradually crystallizes on seeding, rubbing and cooling. After stirring in an ice-bath for one hour, the material is filtered under nitrogen, washed with ether, suspended in fresh ether, cooled for approximately 16 hours, and filtered again to give 3.2 g. (77%) of colorless solid (cis)-4-phenylthio-L-proline hydrobromide; m.p. 106°–109° (s. 99°), $[\alpha]_D^{26}$ $-3°$ (c, 1% in methanol).

Anal. Calc'd. for $C_{11}H_{13}NO_2S \cdot HBr \cdot 0.75\ H_2O$ C, 41.58; H, 4.92; N, 4.41; S, 10.09; L Br,25.15. Found: C, 41.87; H, 4.93; N, 4.43; S, 9.87; Br,25.32.

(d) 1-[D-3-(Acetylthio)-2-methyl-1-oxopropyl]-cis-4-phenylthio-L-proline

Interaction of 3.0 g. (0.0094 mole) of (cis)-4-phenylthio-L-proline hydrobromide and 2.0 g. (0.011 mole) of D-3-acetylthio-2-methylpropionyl chloride in 25 ml. of water as described in Example 1, part (d) (using approximately 15 ml. of 20% sodium carbonate solution to maintain the pH at 8.0 to 8.4), yields 3.8 g. of a pale yellow viscous oil. The dicyclohexylamine salt (prepared in 30 ml. of ethyl acetate employing 1.8 g. of dicyclohexylamine) weighs 2.9 g. (isolated in two crops); m.p. 184°–188° (s. 180°). Following trituration with 15 ml. of acetonitrile one obtains 2.4 g. of colorless solid dicyclohexylamine salt; m.p. 184°–186° (s. 180°), $[\alpha]_D^{26}$ $-75°$ (c, 1% in ethanol).

This dicyclohexylamine salt is treated with 30 ml. of 10% potassium bisulfate and extracted into ethyl acetate as described in Example 1 to yield 2.0 g. (59%) of glass-like 1-[D-3-(acetylthio)-2-methyl-1-oxopropyl]-cis-4- phenylthio-L-proline; m.p. 103°–105° (from ether-hexane); $[\alpha]_D^{25}$ −92° (c, 1% in ethanol).

Anal. Calc'd. for $C_{17}H_{21}NO_4S_2$ C, 55.56; H, 5.76; N, 3.81; S, 17.45. Found: C, 55.62; H, 5.94; N, 3.84; S, 17.40.

(e) 1-(D-3-Mercapto-2-methyl-1-oxopropyl)-cis-4-phenylthio-L-proline

The 1-[D-3-(acetylthio)-2-methyl-1-oxopropyl]-cis-4-phenylthio-L-proline (2.0 g., 0.0042 mole) is treated with 3.5 ml. of concentrated ammonia in 8.5 ml. of water according to the procedure of Example 2 (the solid ammonium salt of the product separates from the reaction mixture) to give 1.35 g. (100%) of viscous syrupy 1-(D-3-mercapto-2-methyl-1-oxopropyl)-cis-4-phenylthio-L-proline; $[\alpha]_D^{26}$ −43° (c, 1% in ethanol).

Anal. Calc'd. for $C_{15}H_{19}NO_3S.0.5\ H_2O$ C, 53.86; H, 6.03; N, 4.19; S, 19.17. Found: C, 54.05; H, 6.17; N, 4.18; S, 19.13.

EXAMPLE 59

(cis)-1-(D-3-Mercapto-2-methyl-1-oxopropyl)-4-(phenylthio)-L-proline, L-arginine salt (1:1)

A solution of 1-(D-3-mercapto-2-methyl-1-oxopropyl)-cis-4-phenylthio-L-proline (5.0 g., 0.01536 mole) dissolved in 286 ml. of absolute ethanol is treated with a solution of L-arginine (98%) (2.70 g., 0.0152 mole) in 28.6 ml. of water to form a clear solution. The solution is concentrated in vacuo to a clear viscous oil. The oil is dissolved in 286 ml. of absolute ethanol and again concentrated in vacuo to a viscous oil. The oil is rubbed under 280 ml. of ether to produce an amorphous solid. The solids are stirred thirty minutes and allowed to settle. The supernatant is removed and the treatment is repeated. Removal of the supernatant left 7.7 g. of amorphous solid (cis)-1-(D-3-mercapto-2-methyl-1-oxopropyl)-4-(phenylthio)-L-proline, L-arginine salt which becomes a free flowing powder on drying in vacuo; m.p. 126°–128°; $[\alpha]_D^{25}$ −43.5° (c=1.0, methanol).

Anal. Calc'd. for $C_{15}H_{19}NO_3S_2 \cdot C_6H_{14}N_4O_2 \cdot \frac{1}{4}H_2O$ C, 50.03; H, 6.70; N, 13.89; S, 12.72. Found: C, 49.89; H, 6.66; N, 14.24; S, 12.67.

EXAMPLE 60

(cis)-1-(D-3-Mercapto-2-methyl-1-oxopropyl)-4-(phenylthio)-L-proline, ethyl ester A stirred solution of 3.9 g. (0.012 mole) of 1-(D-3-mercapto-2-methyl-1-oxopropyl)-cis-4-phenylthio-L-proline in 40 ml. of ethanol is treated under argon with 0.3 ml. of concentrated sulfuric acid, stoppered, and kept at room temperature. After 24 hours, the solution is treated with an additional 0.3 ml. of concentrated sulfuric acid and after standing for three days thin layer chromatography shows the reaction to be completed. The bulk of the ethanol is removed on a rotary evaporator and the oily residue is taken up in 100 ml. of ethyl acetate, stirred, cooled, and treated under argon with 25 ml. of 5% sodium bicarbonate. The layers are separated, the organic phase is washed with 15 ml. of 5% sodium bicarbonate, followed by water (2×5 ml.), dried (MgSO_4), and the solvent evaporated. The oily residue is taken up in ether and the evaporation repeated, finally at 0.2 mm., to give 3.8 g. of nearly colorless viscous oily (cis)-1-(D-3-mercapto-2-methyl-1-oxopropyl)-4-(phenylthio)-L-proline, ethyl ester; $[\alpha]_D^{25}$ −49° (c=1.0, ethanol).

Anal. Calc'd. for $C_{17}H_{23}NO_3S_2$ C, 57.76; H, 6.56; N, 3.96; S, 18.14. Found: C, 57.66; H, 6.53; N, 3.96; S, 18.15.

EXAMPLE 61

1-(D-3-Mercapto-2-methyl-1-oxopropyl)-cis-4-(4-chlorophenylthio)-L-proline

Following the procedure of Example 58 but substituting an equivalent amount of 4-chlorophenylmercaptan for the thiophenol in part (a) one obtains 1-(D-3-mercapto-2-methyl-1-oxopropyl)-cis-4-(4-chlorophenylthio)-L-proline.

EXAMPLE 62

1-(D-3-Mercapto-2-methyl-1-oxopropyl)-cis-4-(3-trifluoromethylphenylthio)-L-proline Following the procedure of Example 54 but substituting an equivalent amount of 3-trifluoromethylphenylmercaptan for the thiophenol in part (a) one obtains 1-(D-3-mercapto-2-methyl-1-oxopropyl-cis-(3-trifluoromethylphenylthio)-L-proline.

EXAMPLE 63

(cis)-4-(4-Hydroxyphenylthio)-1-(3-mercapto-1-oxopropyl)-L-proline (a) (cis)-4-(4-Acetyloxyphenylthio)-L-proline hydrobromide Following the procedure of Example 58 (a) to (c) but substituting an equivalent amount of 4-acetyloxyphenylmercaptan for the thiophenol in part (a) one obtains (cis)-4-(4-acetyloxyphenylthio)-L-proline hydrobromide.

(b) (cis)-4-(4-Acetyloxyphenylthio)-1-[3-(acetylthio)-1-oxopropyl]-L-proline

Interaction of (cis)-4-(4-acetyloxyphenylthio)-L-proline hydrobromide and 3-acetylthiopropionyl chloride according to the procedure described in Example 1, part (d) yields (cis)-4-(4-acetyloxyphenylthio)-1-[3-(acetylthio)-1-oxopropyl]-L-proline.

(c) (cis)-4-(4-Hydroxyphenylthio)-1-(3-mercapto-1-oxopropyl)-L-proline

Hydrolysis of (cis)-4-(4-acetyloxyphenylthio)-1-[3-(acetylthio)-1-oxopropyl]-L-proline with an aqueous ammonia solution according to the procedure of Example 2 yields (cis)-4-(4-hydroxyphenylthio)-1-(3-mercapto-1-oxopropyl)-L-proline.

EXAMPLE 64

(cis)-4-Benzyloxy-1-(D-3-mercapto-2-methyl-1-oxopropyl)-L-proline

Following the procedure of Example 58 but substituting an equivalent amount of benzyl alcohol for the thiophenol in part (a) one obtains (cis)-4-benzyloxy-1-(D-3-mercapto-2-ethyl-1-oxopropyl)-L-proline.

EXAMPLE 65 cis-4-(1-Adamantyloxy)-1-(D-3-mercapto-2-methyl-1-oxopropyl)-L-proline.

(a) N-Carbobenzyloxy-cis-4-(1-adamantyloxy)-L-proline, methyl ester

A solution of 5.3 g. (0.035 mole) of 1-adamantanol in 40 ml. of dimethylformamide and 80 ml. of benzene is treated with 1.6 g. of sodium hydride (50% dispersion in mineral oil). The mixture is refluxed for 15 minutes, cooled, and treated with 7.5 g. (0.017 mole) of N-carbobenzyloxy-trans-4-tosyloxy-L-proline, methyl ester.

The resulting reaction mixture is stirred and refluxed for four hours, cooled, and the solvent removed under reduced pressure. The residue is dissolved in 100 ml. of chloroform and then washed with 25 ml. of water (3 times). The organic phase is dried (MgSO$_4$), filtered, and the solvent evaporated to give N-carbobenzyloxy-cis-4-(1-adamantyl)-L-proline, methyl ester.

(b) N-Carbobenzyloxy-cis-4-(1-adamantyloxy)-L-proline

Treatment of the methyl ester product from part (a) with sodium hydroxide according to the procedure of Example 58 (b) yields N-carbobenzyloxy-cis-4-(1-adamantyloxy)-L-proline.

(c) 1-[D-3-(Acetylthio)-2-methyl-1-oxopropyl]-cis-4-(1-adamantyloxy)-L-proline

Treatment of the product from part (b) with hydrogen bromide according to the procedure of Example 52 (c) and then reacting the resulting product with D-3-acetylthio-2-methylpropionyl chloride according to the procedure of Example 52 (d) yields 1-[D-3-(acetylthio)-2-methyl-1-oxopropyl]-cis-4-(1-adamantyloxy)-L-proline.

(d) cis-4-(1-Adamantyloxy)-1-(D-3-mercapto-2-methyl-1-oxopropyl)-L-proline

The product from part (c) is treated with concentrated ammonia according to the procedure of Example 52 (e) to yield cis-4-(1-adamantyloxy)-1-(D-3-mercapto-2-methyl-1-oxopropyl)-L-proline.

EXAMPLE 66 cis-4-(2-Adamantyloxy)-1-(D-3-mercapto-2-methyl-1-oxopropyl)-L-proline

Following the procedure of Example 65 but substituting 2-adamantanol for the 1-adamantanol in part (a), one obtains cis-4-(2-adamantyloxy)-1-(D-3-mercapto-2-methyl-1-oxopropyl)-L-proline.

EXAMPLE 67 cis-4-(1-Adamantylthio)-1-(D-3-mercapto-2-methyl-1-oxopropyl)-L-proline

Following the procedure of Example 65 but substituting 1-adamantanthiol for the 1-adamantanol, one obtains cis-4-(1-adamantylthio)-1-(D-3-mercapto-2-methyl-1-oxopropyl)-L-proline.

EXAMPLE 68 cis-4-(2-Adamantylthio)-1-(D-3-mercapto-2-methyl-1-oxopropyl)-L-proline

Following the procedure of Example 65 but substituting 2-adamantanthiol for the 1-adamantanol, one obtains cis-4-(2-adamantylthio)-1-(D-3-mercapto-2-methyl-1-oxopropyl)-L-proline.

EXAMPLE 69

(cis)-1-[D-3-(Benzoylthio)-2-methyl-1-oxopropyl]-4-(phenylthio)-L-proline 9.9 g. (0.031 mole) of cis-4-phenylthio-L-proline is suspended in 100 ml. of water (pH 5.6) and the pH is adjusted to 10.2 by the addition of about 20 ml. of 10% sodium bicarbonate to provide a clear solution. The pH is then adjusted to 9.5 by the addition of about 4.5 ml. of concentrated HCl. The solution is kept at 30° while 8.1 g. (0.033 mole) of (D)-3-(benzoylthio)-2-methyl-propanoic acid chloride in 30 ml. of toluene is added simultaneously with 100 ml. of 10% sodium bicarbonate to keep the pH at 9.3. After about ¼ of the acid chloride is added, a slimy precipitate begins to form which persists throughout the reaction. After stirring the reaction mixture at pH 9.3 for 2.5 hours, it is made strongly acidic by adding 20% HCl in the presence of ethyl acetate. The aqueous layer is extracted twice with 350 ml. portions of ethyl acetate and the combined organic layers are washed with 300 ml. of saturated brine and dried (MgSO$_4$). The solvent is removed to yield 11.8 g. of foamy solid crude product.

To a solution of this 11.8 g. (0.027 mole) of foamy solid in 70 ml. of acetonitrile there is added about 6 g. of dicyclohexylamine in 25 ml. of ether. A white crystalline precipitate forms immediately. After standing overnight in the cold room, the solid is filtered and washed with ether to yield (cis)-1-[D-3-(benzoylthio)-2-methyl-1-oxopropyl]-4-(phenylthio)-L-proline, dicyclohexylamine salt (1:1).

Anal. Calc'd. for $C_{22}H_{23}NO_4S_2 \cdot C_{12}H_{23}N$ C, 66.85; H, 7.59; N, 4.59. Found: C, 66.33; H, 7.30; N, 4.48.

The slightly moist dicyclohexylamine salt is stirred for 2.5 hours in a mixture of 300 ml. of ethyl acetate and 200 ml. of 10% potassium bisulfate. Two clear layers form. The aqueous layer is extracted with two 200 ml. portions of ethyl acetate and the combined organic layers are dried (MgSO$_4$). The solvent is removed to yield 10.1 g. of foamy solid (cis)-1-[D-3-(benzoylthio)-2-methyl-1-oxopropyl]-4-(phenylthio)-L-proline; m.p. 42°-44°; $[\alpha]_D^{25}$ −36.5° (c=1, methanol).

Anal. Calc'd. for $C_{22}H_{23}NO_4S_2$ C, 60.87; H, 5.46; N, 3.23. Found: C, 60.75; H, 5.35; N, 3.17.

EXAMPLE 70

(cis)-1-[D-3-(Benzoylthio)-2-methyl-1-oxopropyl]-4-(phenylthio)-L-proline, L-arginine salt (1:1)

2.3 g. (0.0054 mole) of (cis)-1-[D-3-(benzoylthio)-2-methyl-1-oxopropyl]-4-(phenylthio)-L-proline dissolved in 100 ml. of methanol is treated with 0.941 g. (0.0054 mole) of L-arginine. A clear solution forms after stirring for about ten minutes. The reaction mixture is stirred at room temperature for about five hours, the solvent is removed, and the resulting solid is triturated with ether and filtered to yield 2.5 g. of (cis)-1-[D-3-(benzoylthio)-2-methyl-1-oxopropyl]-4-(phenylthio)-L-proline, L-arginine salt (1:1); soft at 105°, m.p. 110°-112° (d); $[\alpha]_D^{25}$ −278° (c=1, methanol).

Anal. Calc'd. for $C_{22}H_{23}NO_4S_2 \cdot C_6H_{14}N_4O_2$ C, 54.88; H, 6.25; N, 11.43; S, 10.47. Found: C, 54.44; H, 6.21; N, 11.60; S, 10.40.

EXAMPLE 71

(cis)-1-[D-3-(Benzoylthio)-2-methyl-1-oxopropyl]-4-(phenylthio)-L-proline, sodium salt (1:1)

A solution of 4.29 g. (0.01 mole) of (cis)-1-[D-3-(benzoylthio)-2-methyl-1-oxopropyl]-4-(phenylthio)-L-proline in 25 ml. of methanol and a solution of 0.540 g. (0.01 mole) of sodium methoxide in 25 ml. of methanol are combined. About 50 ml. of ether are added and after stirring for about 10 minutes a precipitate begins to form. The mixture is allowed to stand overnight in the cold room. The gelatinous solid is filtered, washed with ether and desiccator dried to yield 2.5 g. of (cis)-1-[D-3-(benzoylthio)-2-methyl-1-oxopropyl]-4-(phenylthio)-L-proline, sodium salt (1:1); m.p. 218°-220° (d); $[\alpha]_D^{25}$ −105.2 (c=1, water).

Anal. Calc'd. for $C_{22}H_{22}NO_4S_2 \cdot Na$ C, 57.36; H, 5.03; N, 3.04; Na, 4.99. Found: C, 57.62; H, 5.08; N, 3.01; Na, 4.68.

EXAMPLE 72

(cis)-1-[D-3-(Benzoylthio)-2-methyl-1-oxopropyl]-4-(phenylthio)-L-proline, 2-amino-2-(hydroxymethyl)-1,3-propanediol salt (1:1)

A solution of 121.14 mg. (0.001 mole) of tris(hydroxymethyl)aminoethane in 5 ml. of n-butanol and a solution of 429.5 mg. of (cis)-1-[D-3-(benzoylthio)-2-methyl-1-oxopropyl]-4-(phenylthio)-L-proline in 5 ml. of n-butanol are combined. The resulting clear solution is allowed to stand for 48 hours. The solution is seeded and the entire mass crystallizes. It is allowed to stand for 3 hours, filtered, washed well with ether and dried to yield 400 mg. of (cis)-1-[D-3-(benzoylthio)-2-methyl-1-oxopropyl]-4-(phenylthio)-L-proline, 2-amino-2-hydroxymethyl-1,3-propanediol salt (1:1); m.p. 135°–136°; $[\alpha]_D^{25}$ −20.6 (c=1, water).

Anal. Calc'd. for $C_{22}H_{23}NO_4S_2 \cdot C_4H_{11}NO_3$ C, 56.70; H, 6.22; N, 5.09. Found: C, 56.66; H, 6.36; N, 5.00.

EXAMPLE 73

(cis)-1-[D-3-(Benzoylthio)-2-methyl-1-oxopropyl]-4-(phenylthio)-L-proline, potassium salt (1:1)

A solution of 21.5 g. (0.05 mole) of (cis)-1-[D-3-(benzoylthio)-2-methyl-1-oxopropyl]-4-(phenylthio)-L-proline in 100 ml. of ethanol and 50 ml. of 1 N alcoholic potassium hydroxide are combined and a crystalline solid begins to form almost immediately. The mixture is allowed to stand overnight in the cold room. The solid is filtered, washed with 60 ml. of cold ethanol, washed with two 100 ml. portions of ether, and dried in vacuo overnight to yield 16.5 g. of product that contains ethanol. 14.4 g. of this material is allowed to dry at room temperature over 60 hours to yield 14.2 g. [no alcohol present] of (cis)-1-[D-3-(benzylthio)-2-methyl-1-oxopropyl]-4-(phenylthio)-L-proline, potassium salt (1:1); m.p. 195°–205°; $[\alpha]_D^{25}$ −114° (c=1, water).

Anal. Calc'd. for $C_{22}H_{22}NO_4S_2K \cdot 1\frac{1}{2} H_2O$ C, 53.41; H, 5.09; N, 2.83; S, 12.96; K, 7.88. Found: C, 53.55; H, 4.89; N, 2.90; S, 12.88; K, 8.03.

EXAMPLE 73a (cis)-1-[D-3-(Benzoylthio)-2-methyl-1-oxopropyl]-4-(phenylthio)-L-proline potassium salt (1:1)

The product of Example 73 can also be made according to the following procedure:

(a) N-Benzoyl-cis-4-phenylthio-L-proline

N-Benzoyl-trans-4-tosyloxy-L-proline, methyl ester [prepared according to the procedure of Portoghese et al., Tetrahedron, Vol. 27, p 961–967] (750 g., 1.86 moles) is added to 2.5 liters of methanol and the mixture is heated and agitated at 35°. 200 ml. (1.95 mole) of thiophenol is added followed by a solution of 78 g. of sodium hydroxide (1.95 mole) in 500 ml. of methanol. The mixture is heated to reflux until TLC shows the reaction to be complete. The mixture is allowed to cool to room temperature and a solution of 80 g. of sodium hydroxide in 500 ml. of water is added with continued agitation for one hour. The solvent is removed in vacuo and the oily concentrate is diluted with 2.5 liters of water and extracted with 0.7 liters of isobutyl alcohol. The pH of the aqueous phase is adjusted to below 2 with 0.2 liters of concentrated HCl. The precipitated oil is extracted with 2 liters of isobutyl acetate in three portions. The organic layer is filtered and vacuum concentrated to 650 g. of N-benzoyl-cis-4-phenylthio-L-proline as a thick syrup.

(b) cis-4-Phenylthio-L-proline

The N-benzoyl-cis-4-phenylthio-L-proline is heated on a steam bath and 0.5 liters of glacial acetic acid are added. The mixture is swirled and 0.5 liters of water followed by 100 ml. of concentrated sulfuric acid are added. The turbid mixture is heated at reflux at an oil bath temperature of about 125° and maintained at reflux until the reaction is completed. The reaction liquid is cooled to room temperature and 0.75 liters of isobutyl acetate and 3 kg. of cracked ice are added with brisk agitation. 50 g. of concentrated aqueous sodium hydroxide solution are added and the product is collected and washed with methanol. The product is further purified by dissolution in aqueous sodium hydroxide, treatment with activated carbon, filtration, and careful crystallization with HCl. The crystals are collected, washed with water, and dried to yield cis-4-phenyl-thio-L-proline as a white crystalline powder; m.p. 240° (d); $[\alpha]_D^{23}$ −118° (C=1, N sodium hydroxide).

Anal. Calc'd. for $C_{11}H_{13}NO_2S$: C, 59.17; H, 5.87; N, 6.27; S, 14.36. Found: C, 58.58, H, 5.63; N, 6.28; S, 14.07.

(c) (cis)-1-[D-3-(Benzoylthio)-2-methyl-1-oxopropyl]-4-(phenylthio)-L-proline, potassium salt (1:1)

cis-4-Phenylthio-L-proline is acylated in water at pH 8.3 with an equimolar amount of (D)-3-(benzoylthio)-2-methylpropanoyl chloride. The pH is maintained at 8–8.5 by the addition of 5 N sodium hydroxide solution. The reaction mixture is acidified with hydrochloric acid and the product is extracted into isobutyl acetate. Concentration of the brine-washed extract furnishes crude (cis)-1-[D-3-(benzoylthio)-2-methyl-1-oxopropyl]-4-(phenylthio)-L-proline as a tacky resin.

This resinous material is dissolved in isopropanol and a solution of potassium 2-ethyl-hexanoate in isopropanol is added at a slow rate at elevated temperature. The isopropyl adduct of the desired potassium salt crystallizes.

The adduct is collected, washed with isopropanol and vacuum dried. Exposure of the dried adduct to moist air causes the exchange of water for the isopropanol and yields (cis)-1-[D-3-(benzoylthio)-2-methyl-1-oxopropyl]-4-(phenylthio)-L-proline, potassium salt (1:1).

EXAMPLE 74

(cis)-1-[D-3-(Benzoylthio)-2-methyl-1-oxopropyl]-4-(phenylthio)-L-proline, magnesium salt (2:1)

Mixtures of 429.5 mg. (0.01 mole) of cis-1-[D-3-(benzoylthio)-2-methyl-1-oxopropyl]-4-(phenylthio)-L-proline in 30 ml. of ethanol and 29.1 mg. (0.005 mole) of magnesium hydroxide in 30 ml. of water are combined and a clear solution results. The solution is stirred at room temperature overnight. The pH is 5.9. The ethanol is removed and a cloudy mixture forms. The aqueous layer is extracted with ether and then freed of residual ether on a flash evaporator and lyophillized to yield 150 mg. of (cis)-1-[D-3-(benzoylthio)-2-methyl-1-oxopropyl]-4-(phenylthio)-L-proline, magnesium salt (2:1); soft at 80°, m.p. 110°–120°.

Anal. Calc'd. for $C_{22}H_{22}NO_4S_2 \cdot 0.5$ Mg$\cdot$2 $H_2O$ C, 55.42; H, 5.49; N, 3.05. Found: C, 55.39; H, 4.93; N, 2.94.

EXAMPLE 75

(cis)-1-[D-3-(Benzoylthio)-2-methyl-1-oxopropyl]-4-(phenylthio)-L-proline, calcium salt (2:1)

Mixtures of 859 mg. (0.002 mole) of (cis)-1-[D-3-(benzoylthio)-2-methyl-1-oxopropyl]-4-(phenylthio)-L-proline in 50 ml. of ethanol and 56 mg. (0.001 mole) of calcium oxide suspended in 50 ml. of water are combined and a clear solution formed. The solution becomes cloudy and is allowed to stir at room temperature overnight. There is solid present. The ethanol is removed by flash evaporation and the suspension is extracted with ether and traces of ether are then removed from the aqueous suspension by flash evaporation. The suspension is lyophilized to yield 400 mg. of (cis)-1-[D-3-(benzoylthio)-2-methyl-1-oxopropyl]-4-(phenylthio)-L-proline, calcium salt (2:1); m.p. 235°–237° (d).

Anal. Calc'd. for $C_{22}H_{22}NO_4S_2 \cdot 0.5\ Ca \cdot 0.5\ H_2O$ C, 55.74; H, 5.06; N, 3.06. Found: C, 57.07; H, 5.02; N, 2.84.

This product can also be obtained according to the following procedure. (cis)-1-[D-3-(Benzoylthio)-2-methyl-1-oxopropyl]-4-(phenylthio)-L-proline, potassium salt is dissolved in water to a 5% solution. A moderate excess of 2 N aqueous calcium chloride is added very slowly with seeding. The desired calcium salt crystallizes in the form of very small platelets. These are collected on a filter and are washed with liberal amounts of water. Vacuum drying at slightly elevated temperature yields the desired calcium salt as a fine anhydrous powder; m.p. about 250°; $[\alpha]_D^{23}\ -67.6°$ (c=1, methanol/HCl).

EXAMPLE 76

1,1'-[Dithiodi-(1-D-3-mercapto-2-methyl-1-oxopropyl)]bis[(cis)-4-(phenylthio)-L-proline]

A mixture of 2.9 g. (0.089 mole) of (cis)-1-(D-3-mercapto-2-methyl-1-oxopropyl)-4-(phenylthio)-L-proline and 9 ml. of 1 N sodium hydroxide in 70 ml. of water is stirred and treated dropwise with a solution of 1.2 g. (0.047 mole) of iodine in 10 ml. of 95% ethanol while maintaining the pH of the solution at 5.5 to 6.5 with 1 N sodium hydroxide. After about 15 minutes the slight excess of iodine color is removed with dilute sodium thiosulfate and the reaction mixture is acidified with 6 N HCl and extracted with ethyl acetate (3×70 ml.). The organic phases are combined, dried (MgSO₄), filtered, and the solvent evaporated to give 2.4 g. of yellow foam-like solid, m.p. 75°–85° (s. 47°). This material is dissolved in 40 ml. of ethyl acetate and treated with a solution of 1.4 g. of dicyclohexylamine in 5 ml. of ethyl acetate. The product rapidly separates as a gelatinous material. After standing overnight at room temperature, the solid is filtered to give 4.2 g. of a pale yellow solid; m.p. 205°–207°. This material is crystallized from 40 ml. of ethanol to give 2.8 g. of colorless solid 1,1'-[dithiodi-(1-D-3-mercapto-2-methyl-1-oxopropyl)]bis[(cis)-4-(phenylthio)-L-proline], dicyclohexylamine salt; m.p. 207°–209°.

Anal. Calc'd. for $C_{30}H_{36}N_2O_6S_4 \cdot 2(C_{12}H_{23}N)$ C, 64.12; H, 8.17; N, 5.54; S, 12.68. Found: C, 63.87; H, 8.30; N, 5.45; S, 12.46.

The above dicyclohexylamine salt is crushed in a mortar, suspended in 30 ml. of ethyl acetate, treated with 30 ml. of 10% potassium bisulfate and shaken to give two layers. The organic phase is separated and the aqueous phase is extracted with ethyl acetate (3×30 ml.). The organic phases are combined, washed twice with 10 ml. of water, dried (MgSO₄), filtered and the solvent evaporated to give a foam-like solorless solid. The latter is treated with 25 ml. of ether (solid becomes an oil) and the solvent is removed on a rotary evaporator to give 1.8 g. of colorless granular 1,1'-[dithiodi-(1-D-3mercapto-2-methyl-1-oxopropyl)]bis[(cis)-4-(phenylthio)-L-proline]; m.p. 75°–90° (s. 65°); $[\alpha]_D^{25}\ -42°$ (c=1, ethanol).

Anal. Calc'd. for $C_{30}H_{36}N_2O_6S_4 \cdot \frac{1}{2}\ H_2O$ C, 54.77; H, 5.67; N, 4.26; S, 19.50. Found: C, 54.79; H, 5.95; N, 4.01; S, 19.52.

EXAMPLE 77

1,1'-[Dithiodi-(1-D-3-mercapto-2-methyl-1-oxopropyl)]bis[(cis)-4-(phenylthio)-L-proline], dipotassium salt A stirred solution of 7.0 g. of (0.0106 mole) of 1,1'-[dithiodi-(1-D-3-mercapto-2-methyl-1-oxopropyl)]bis[-(cis)-4-(phenylthio)-L-proline] in 200 ml. of ethanol is treated with 21.3 ml. of 1 N potassium hydroxide (2 equivalents) in ethanol. The resulting solution is seeded, allowed to crystallize at room temperature for several hours and placed in the cold room overnight. The solid is filtered, washed with ethanol and ether to give 5.2 g. of colorless solid; m.p. 275° (dec.). The material is then air dried overnight to yield 5.3 g. of 1,1'-[dithiodi-(1-D-3-mercapto-2-methyl-1-oxopropyl)]bis[(cis)-4-(phenylthio)-L-proline], dipotassium salt; m.p. 275° (dec.); $[\alpha]_D^{25}\ -227°$ (c=1, water).

Anal. Calc'd. for $C_{30}H_{34}N_2O_6S_4 \cdot 2K \cdot 3\ H_2O$ C, 46.24; H, 5.17; N, 3.59; S, 16.46; K, 10.04. Found: C, 45.98; H, 5.11; N, 3.36; S, 16.10; K, 10.03.

EXAMPLE 78

(cis)-4-(Cyclohexyloxy)-1-(D-3-mercapto-2-methyl-1-oxopropyl)-L-proline

Following the procedure of Example 58 but substituting the sodium salt of cyclohexanol for the sodium thiophenol, one obtains (cis)-4-(cyclohexyloxy)-1-(D-3-mercapto-2-methyl-1-oxopropyl)-L-proline.

EXAMPLE 79

(trans)-1-(3-Mercapto-1-oxopropyl)-3-methylthio-D,L-proline (a) 1,2-Dehydroproline, t-butyl ester To a stirred solution of 34.2 g. (0.20 mole) of proline t-butyl ester in 600 ml. of ether at −5° to 0° is added dropwise over ten minutes 21.7 g. (23.9 ml., 0.20 mole) of freshly prepared t-butyl hypochlorite [Org. Syn., Coll. Vol. V, 184 (1973)]. During the addition, the temperature is maintained at −5° to 0°. After the addition is complete, the solution is stirred at this temperature for an additional five minutes.

To the vigorously stirred solution is added rapidly (~3–5 min.) a solution of 7.8 g. (0.02 mole) of potassium in freshly distilled dry (CaH₂)t-butanol. After the addition, the temperature of the reaction mixture is about 18°. The reaction vessel is removed from the cooling bath and stirred for thirty minutes. The reaction mixture is filtered through Celite (diatomaceous earth) and the filtrate concentrated in vacuo. The residue is taken up in ether and washed with several portions of water. The ether solution is dried and concentrated in vacuo to 31.6 g. of yellow liquid. A trace of hydroquinone is added and the crude product distilled, affording 22.4 g. of 1,2-dehydroproline, t-butyl ester (66%) b.p. 60°–62°/0.1 mm.

(b) 1-Benzyloxycarbonyl-4,5-dihydro-1H-pyrrole-2-carboxylic acid, t-butyl ester

A solution of 16.9 g. (0.1 mole) of 1,2-dehydroproline, t-butyl ester in 70 ml. of dichloromethane is cooled to $-10°$ under argon. A solution of freshly distilled benzylchloroformate (14.2 ml., 0.1 mole, b.p. 62°–64° (0.4 mm)) in 70 ml. of dichloromethane is added dropwise over a period of 30 minutes. After stirring in the cold for another 30 minutes a solution of 15.22 g. (0.1 mole) of 1,5-diazabicyclo[5.4.0]undec-5-ene in 70 ml. of dichloromethane is added over a period of 20 minutes. The cooling bath is then removed and the mixture is stirred at room temperature for one hour. After washing twice with cold dilute hydrochloric acid and once with saturated sodium carbonate solution, the solution is dried in vacuo to yield 18.2 g. (60%) of 1-benzloxycarbonyl-4,5-dihydro-1H-pyrrole-2-carboxylic acid, t-butyl ester as a pale yellow oil.

(c) (trans)-1-Benzyloxycarboxy-3-methylthio-D,L-proline, t-butyl ester

A solution of 18.2 g. (0.06 mole) of 1-benzyloxycarbonyl-4,5-dihydro-1H-pyrrole-2-carboxylic acid, t-butyl ester in 180 ml. of dry methanol is treated with 3.24 g. (0.06 mole) of sodium methoxide and cooled in an ice-bath. Methanethiol is bubbled into the solution slowly for 30 minutes. The mixture is stirred overnight under argon at room temperature. Dilute aqueous acetic acid is added until the solution is slightly acidic. Argon is bubbled through the solution for one hour before it is taken to near dryness in vacuo. Ethyl acetate is added and the solution is washed twice with saturated sodium carbonate solution, dried and freed of solvent in vacuo to yield 17 g. of yellow oil. This oil is chromatographed using 300 g. of silica gel and petroleum ether: ether (4:1) to yield 11.1 g. of (trans)-1-benzyloxycarbonyl-3-methylthio-D,L-proline as a colorless oil.

(d) (trans)-3-Methylthio-D,L-proline 8.4 g. (0.024 mole) of (trans)-1-benzyloxycarbonyl-3-methylthio-D,L-proline are treated with 45 ml. of 4 N hydrobromic acid in acetic acid. After stirring for one hour at room temperature the solution is dried in vacuo. A small amount of water is added and this is washed twice with ether. The aqueous solution is applied to a column containing 300 ml. of an ion-exchange resin and water is passed through until the eluate is no longer strongly acidic. The product is then eluted with pH 6.5 (aqueous pyridine acetate) buffer. Fractions positive to ninhydrin are combined and lyophilized to give 3.4 g. (88%) of white fluff. A small sample of this material is crystallized from methanol to give (trans)-3-methylthio-D,L-proline; m.p. 196°–200° (dec.) (s. 192°).

Anal. Calc'd. for $C_6H_{11}O_2NS$: C, 44.70; H, 6.88; N, 8.69; S, 19.89. Found: C, 44.53; H, 7.10; N, 8.61; S, 19.95.

(e) (trans)-1-[3-(Acetylthio)-1-oxopropyl]-3-methylthio-D,L-proline 3.05 g. (0.019 mole) of (trans)-3-methylthio-D,L-proline is dissolved in 19 ml. of 1 N sodium carbonate and diluted with 10 ml. of water. The solution is cooled in an ice-bath and while stirring rapidly a solution of 3-acetylthiopropionyl chloride in 20 ml. of ether is added. The pH is maintained at 8 by adding 1 N sodium carbonate. At the end of 30 minutes the pH is holding constant and 45 ml. of sodium carbonate solution had been added. The layers are separated and the aqueous layer is washed once with ether. The aqueous layer is then acidified with 10% potassium bisulfate solution and the product is extracted into ethyl acetate, dried and freed of solvent in vacuo to give 5.2 g. of oil. The material is chromatographed on 150 g. silica gel using ethyl acetate for elution. 3.85 g. of somewhat crude (trans)-1-[3-(acetylthio)-1-oxopropyl]-3-methylthio-D,L-proline are obtained.

A small sample is dissolved in ether and converted to the dicyclohexylamine salt which is the recrystallized from ethyl acetate to give (trans)-1-[3-(acetylthio)-1-oxopropyl]-3-methylthio-D,L-proline, dicyclohexylamine salt; m.p. 153°–157°.

Anal. Calc'd. for $C_{11}H_{17}O_4NS$: $(C_6H_{11})_2NH$: C, 58.44; H, 8.53; N, 5.83; S, 13.57. Found: C, 58.77; H, 8.57; N, 5.68; S, 13.74.

(f) (trans)-1-(3-Mercapto-1-oxopropyl)-3-methylthio-D,L-proline 2.05 g. (0.007 mole) of (trans)-1-[3-(acetylthio)-1-oxopropyl]-3-methylthio-D,L-proline is cooled in an ice-bath under argon and treated with a cold argon saturated mixture of 7 ml. of water and 7 ml. of concentrated ammonia. After stirring for 30 minutes at 0° the solution is acidified with hydrochloric acid. The product is extracted into ethyl acetate, dried and freed of solvent in vacuo to give 1.85 g. of material which becomes partially crystalline on standing. Trituration with ether gives 1.0 g. (57%) of white crystalline product. Recrystallization from ethyl acetate (5 ml.) gives 0.85 g. of (trans)-1-(3-mercapto-1-oxopropyl)-3-methylthio-D,L-proline; m.p. 89°–93°.

Anal. Calc'd. for $C_9H_{15}O_3NS_2$: C, 43.35; H, 6.06; N, 5.62; S, 25.72. Found: C, 43.35; H, 6.27; N, 5.54; S, 25.91.

EXAMPLE 80

(trans)-1-(D-3-Mercapto-2-methyl-1-oxopropyl)-3-ethylthio-D,L-proline (a) (trans)-3-Ethylthio-D,L-proline Following the general procedure of Example 79 (a) to (d) but substituting an equivalent amount of ethyl mercaptan for the methanethiol one obtains (trans)-3-ethyl-D,L-proline.

(b) (trans)-1-[D-3-(Acetylthio)-2-methyl-1-oxopropyl]-3-ethylthio-D,L-proline

Interaction of the (trans)-2-ethylthio-D,L-proline and D-3-acetylthio-2-methylpropionyl chloride according to the procedure of Example 3 yields (trans)-1-[D-3-(acetylthio)-2-methyl-1-oxopropyl]-3-ethylthio-D,L-proline.

(c) (trans)-1-(D-3-Mercapto-2-methyl-1-oxopropyl)-3-ethylthio-D,L-proline

Hydrolysis of (trans)-1-[D-3-(acetylthio)-2-methyl-1-oxopropyl]-3-ethylthio-D,L-proline with an aqueous ammonia solution according to the procedure of Example 4 yields (trans)-1-(D-3-mercapto-2-methyl-1-oxopropyl)-3-ethylthio-D,L-proline.

EXAMPLE 81

(trans)-1-(3-Mercapto-1-oxopropyl)-3-phenylthio-D,L-proline

Following the general procedure of Example 79 but substituting an equivalent amount of thiophenol for the methanethiol yields (trans)-1-(3-mercapto-1-oxopropyl)-3-phenylthio-D,L-proline.

EXAMPLE 82

(cis)-4-Methoxy-1-(D-3-mercapto-2-trifluoromethyl-1-oxopropyl)-L-proline (a) 3-(4-Methoxybenzyl)thio-2-trifluoromethylpropionyl chloride A neat mixture of 1-trifluoromethylacrylic acid (3.9 g.) and 4-methoxybenzylthiol (4.3 g.) is stirred at 100°–110° for one hour. The mixture is allowed to cool to room temperature and the solid is recrystallized from cyclohexane to yield 3-(4-methoxybenzyl)thio-2-trifluoromethylpropanoic acid, m.p. 72°–74°.

Treatment of this acid with thionyl chloride yields 3-(4-methoxybenzyl)thio-2-trifluoromethylpropionyl chloride.

(b) (cis)-4-Methoxy-1-[D-3-(4-methoxybenzyl)thio-2-trifluoromethyl-1-oxopropyl]-L-proline The 3-(4-methoxybenzyl)thio-2-trifluoromethylpropionyl chloride is reacted with (cis)-4-methoxy-L-proline to yield (cis)-4-methoxy-1-[D-3-(4-methoxybenzyl)thio-2-trifluoromethyl-1-oxopropyl]-L-proline.

(c) (cis)-4-Methoxy-1-(D-3-mercapto-2-trifluoromethyl-1-oxopropyl)-L-proline

The (cis)-4-methoxy-1-[D-3-(4-methoxybenzyl)thio-2-trifluoromethyl-1-oxopropyl]-L-proline is mixed with trifluoroacetic acid and anisole and stirred under nitrogen. The solvents are removed under vacuum to yield as a residue (cis)-4-methoxy-1-(D-3-mercapto-2-trifluoromethyl-1-oxopropyl)-L-proline.

EXAMPLE 83

(trans)-4-Methoxy-1-(D-3-mercapto-2-trifluoromethyl-1-oxopropyl)-L-proline

Following the procedure of Example 82 but substituting (trans)-4-methoxy-L-proline for the cis isomer one obtains (trans)-4-methoxy-1-(D-3-mecapto-2-trifluoromethyl-1-oxopropyl)-L-proline.

EXAMPLE 84

(trans)-4-Ethoxy-1-(D-3-mercapto-2-trifluoromethyl-1-oxopropyl)-L-proline (a) 3-Acetylthio-2-trifluoromethylpropionyl chloride A mixture of thiolacetic acid and 2-(trifluoromethyl)acrylic acid is heated on a steam bath for one hour and then stored at room temperature for 18 hours. The reaction mixture is distilled in vacuo to give 3-acetylthio-2-trifluoromethylpropanoic acid.

Treatment of this acid with thionyl chloride yields 3-acetylthio-2-trifluoromethylpropionyl chloride.

(b) (trans)-4-Ethoxy-1-[D-3-(acetylthio)-2-trifluoromethyl-1-oxopropyl]-L-proline Reacting 3-acetylthio-2-trifluoromethylpropionyl chloride with trans-4-ethoxy-L-proline according to the procedure of Example 3 yields (trans)-4-ethoxy-1-[D-3-(acetylthio)-2-trifluoromethyl-1-oxopropyl]-L-proline.

(c) (trans)-4-Ethoxy-1-(D-3-mercapto-2-trifluoromethyl-1-oxopropyl)-L-proline

Treating (trans)-4-ethoxy-1-[D-3-(acetylthio)-2-trifluoromethyl-1-oxopropyl]-L-proline with an aqueous solution of ammonia according to the procedure of Example 4 yields (trans)-4-ethoxy-1-(D-3-mercapto-2-trifluoromethyl-1-oxopropyl)-L-proline.

EXAMPLE 85

(cis)-1-(D-3-Mercapto-2-methyl-1-oxopropyl)-3-phenoxy-D,L-proline (a) 3-Phenoxy-1,2-Dehydroproline, t-butyl ester A mixture of 9.25 g. (50 mmole) of 1,2-dehydroproline, t-butyl ester in 70 ml. of toluene with 8.9 g. (50 mmole) of n-bromosuccinimide is heated at reflux while exposed to a sunlamp (2 inches away) for one hour. During this time succinimide is produced and the reaction is cooled to room temperature. The succinimide is removed by filtration and the filtrate evaporated to dryness. The residue is distilled at 80° yielding 3.5 g. of crude 3-bromo-1,2-dehydroproline, t-butyl ester.

A mixture of this crude 3-bromo-1,2-dehydroproline, t-butyl ester and thallium phenoxide (3.9 g., 13 mmole) in 30 ml. of dry dimethylformamide is stirred at room temperature under argon for 24 hours. The solvent is removed under vacuum and the residue is diluted with ether to precipitate thallium bromide which is removed by filtration. The filtrate is concentrated yielding an oil that is purified by distillation. After two hours at 0.005 mm. and 80°, 1.48 g. of 3-phenoxy-1,2-dehydroproline, t-butyl ester are left in the distillation flask.

(b) (cis)-3-Phenoxy-D,L-proline

A mixture of the 1.48 g. of 3-phenoxy-1,2-dehydroproline, t-butyl ester, 5 ml. of 1 N sodium hydroxide and 20 ml. of 80% dioxane/water is stirred at room temperature for four hours. The solvents are removed in vacuo and the residue is dissolved in 25 ml. of water and treated with 168 mg. of sodium borohydride over a one hour period at room temperature. The mixture is acidified to pH 6 by the addition of 2 N HCl and the solution is kept at 0° for 16 hours whereupon crystals of (trans)-3-phenoxy-D,L-proline precipitate (about 25 mg.). These are removed by filtration and the filtrate is desalted by passage through a Dowex 50 W×8 column (1"×12") using 1 N ammonium hydroxide as the eluent. The UV active fractions are combined and concentrated to give 616 mg. of solid (cis)-3-phenoxy-D,L-proline.

(c) (cis)-1-[D-3-(Acetylthio)-2-methyl-1-oxopropyl]-3-phenoxy-D,L-proline

The 616 mg. of (cis)-3-phenoxy-D,L-proline is slurried in 20 ml. of water at 5° and the pH is adjusted to 8.0 with solid sodium carbonate. A solution of 550 mg. (2.5 mmole) of D-3-acetylthio-2-methylpropanoyl acid chloride in 1 ml. of ether is added and the pH of the reaction mixture is kept between 7.3 and 8.2 for the next 1.5 hours by the addition of sodium carbonate. The mixture is washed with ethyl acetate (2×20 ml.), acidified to pH 2 by the addition of 10% HCl and extracted with ethyl acetate (3×50 ml.). The extracts are combined, dried (MgSO$_4$) and concentrated to yield 810 mg. of an oil. This oil is purified by flash chromatography on silica gel (LP-1, 300 ml.) using 10–20% acetic acid-toluene mixtures as eluents and yields 530 mg. of (cis)-1-[D-3-(acetylthio)-2-methyl-1-oxopropyl]-3-phenoxy-D,L-proline.

(d) (cis)-1-(D-3-Mercapto-2-methyl-1-oxopropyl)-3-phenoxy-D,L-proline

The 530 mg. of (cis)-1-[D-3-(acetylthio)-2-methyl-1-oxopropyl]-3-phenoxy-D,L-proline is dissolved in 50/50 concentrated ammonia hydroxide/water (degassed by bubbling argon through the solution for 15 minutes) under argon and stirred at room temperature for 1.5 hours. The slightly cloudy solution is adjusted to pH 6.5 with concentrated HCl (some warming occurs) and extracted with methylene chloride (2×25 ml.). The pH is then adjusted to 1 and the solution again extracted with methylene chloride (3×50 ml.). The extracts are combined, dried (MgSO₄) and concentrated yielding 410 mg. of a glassy compound. Trituration with chloroform results in crystallization. The solid is recrystallized from ethyl acetate-hexane yielding 261 mg. of (cis)-1-(D-3-mercapto-2-methyl-1-oxopropyl)-3-phenoxy-D,L-proline; m.p. 134°-155°.

Anal. Calc'd. for $C_{15}H_{19}NO_4S$ C, 58.23; H, 6.19; N, 4.53; S, 10.36. Found: C, 58.07; H, 6.18; N, 4.45; S, 10.16.

EXAMPLE 86

(cis)-1-(D-3-Mercapto-2-methyl-1-oxopropyl)-3-phenylthio-D,L-proline

Following the procedure of Example 85 but substituting thallium thiophenol for the thallium phenoxide in part (a), one obtains (cis)-1-(D-3-mercapto-2-methyl-1-oxopropyl)-3-phenylthio-D,L-proline.

EXAMPLE 87

(cis)-1-[D-3-[[(Phenylmethyl)carbonyl]thio]-2-methyl-1-oxopropyl]-4-(phenylthio)-L-proline Following the procedure of Example 69 but employing (D)-3-(phenylacetylthio)-2-methylpropanoic acid chloride one obtains (cis)-1-[D-3-[[(phenylmethyl)carbonyl]thio]-2-methyl-1-oxopropyl]-4-phenylthio-L-proline.

EXAMPLE 88

(cis)-1-[D-3-[[(4-Methoxyphenyl)carbonyl]thio]-2-methyl-1-oxopropyl]-4-(phenylthio)-L-proline Following the procedure of Example 69 but employing (D)-3-(4-methoxybenzoylthio)-2-methylpropanoic acid chloride one obtains (cis)-1-[D-3-[[(4-(methoxyphenyl)carbonyl]thio]-2-methyl-1-oxopropyl]-4-(phenylthio)-L-proline.

EXAMPLE 89

1000 tablets each containing 100 mg. of 1-(D-3-mercapto-1-oxopropyl)-trans-4-methoxy-L-proline, sodium salt, are produced from the following ingredients:

| | |
|---|---|
| 1-(3-mercapto-1-oxopropyl)-trans-4-methoxy-L-proline, sodium salt | 100 g. |
| Corn starch | 50 g. |
| Gelatin | 7.5 g. |
| Avicel (microcrystalline cellulose) | 25 g. |
| Magnesium stearate | 2.5 g. |

The 1-(D-3-mercapto-1-oxopropyl)-trans-4-methoxy-L-proline salt and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg. of active ingredient.

EXAMPLE 90

Tablets each containing 200 mg. of 1-(D-3-mercapto-2-methyl-1-oxopropyl)-trans-4-methoxy-L-proline are produced as described in Example 89.

EXAMPLE 91

1000 tablets each containing 50 mg. of 1-(D-3-mercapto-2-methyl-1-oxopropyl)-cis-4-methoxy-L-proline, sodium salt, are produced from the following ingredients:

| | |
|---|---|
| 1-(D-3-mercapto-2-methyl-1-oxopropyl)-cis-4-methoxy-L-proline, sodium salt | 50 g. |
| Lactose | 25 g. |
| Avicel | 38 g. |
| Corn starch | 15 g. |
| Magnesium stearate | 2 g. |

The 1-(D-3-mercapto-2-methyl-1-oxopropyl)-cis-4-methoxy-L-proline, sodium salt, lactose and Avicel are admixed, then blended with the corn starch. Magnesium stearate is added. The dry mixture is compressed in a tablet press to form 1000 130 mg. tablets each containing 50 mg. of active ingredient. The tablets are coated with a solution of Methocel E 15 (methyl cellulose) including as a color a lake containing yellow #6.

EXAMPLE 92

Two piece #1 gelatin capsules each containing 100 mg. of 1-(D-3-mercapto-2-methyl-1-oxopropyl)-cis-4-methoxy-L-proline, sodium salt, are filled with a mixture of the following ingredients:

| | |
|---|---|
| 1-(D-3-mercapto-2-methyl-1-oxopropyl)-cis-4-methoxy-L-proline, sodium salt | 100 mg. |
| Magneium stearate | 7 mg. |
| USP Lactose | 193 mg. |

EXAMPLE 93

1000 tablets each containing the following ingredients:

| | |
|---|---|
| (cis)-1-[D-3-(Benzoylthio)-2-methyl-1-oxopropyl]-4-(phenylthio)-L-proline, calcium salt (2:1) | 50 mg. |
| Lactose | 25 mg. |
| Avicel | 38 mg. |
| Corn starch | 15 mg. |
| Magnesium stearate | 2 mg. |
| | 130 mg. | are prepared by admixing the (cis)-1-[D-3-(benzoylthio)-2-methyl-1-oxopropyl]-4-(phenylthio)-L-proline, calcium salt (2:1), lactose and Avicel and then blending with corn starch. Magnesium stearate is added. The dry mixture is compressed in a tablet press to form 1000 130 mg. tablets each containing 50 mg. of active ingredient. The tablets are coated with a solution of Methocel E 15 (methyl cellulose) including as a color a lake containing yellow #6.

EXAMPLE 94

1000 tablets each containing the following ingredients:

| | |
|---|---|
| (cis)-1-[D-3-(Benzoylthio)-2-methyl-1-oxopropyl]-4-(phenylthio)-L-proline, | |

| -continued | |
|---|---|
| potassium salt (1:1) | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are produced from sufficient bulk quantities by slugging the (cis)-1-[D-3-(benzoylthio)-2-methyl-1-oxopropyl]-4-(phenylthio)-L-proline, potassium salt (1:1), Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

EXAMPLE 95

An injectable solution is produced as follows:

| (trans)-4-methoxy-1-(D-3-mercapto-2-methyl-1-oxopropyl)-L-proline | 500 | g. |
|---|---|---|
| Methyl paraben | 5 | g. |
| Propyl paraben | 1 | g. |
| Sodium chloride | 25 | g. |
| Water for injection qs. | 5 | l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

The products of each example can be similarly formulated as in Examples 89–95.

What is claimed is:

1. A compound of the formula $$R_4-S-(CH)_n-\underset{\underset{R_3}{|}}{CH}-\underset{\underset{R_2}{|}}{CH}-CO-N\underset{\underset{H}{|}}{\overset{H_2C}{\diagup}}\overset{4}{\underset{3}{\diagdown}}\underset{C_*-COOR}{\overset{X-R_1}{|}}$$

or a basic salt thereof wherein
the X—R$_1$ group is located at the 3- or 4-position of the proline ring;
X is oxygen or sulfur;
R is hydrogen or lower alkyl;
R$_1$ is lower alkyl, lower alkenyl, lower alkynyl, cycloalkyl, 1- or 2-adamantyl, phenyl, phenyl-lower alkylene, 1- or 2-naphthyl, biphenyl, substituted phenyl, substituted phenyl-lower alkylene, substituted 1- or 2-naphthyl, or substituted biphenyl wherein said substituent is one or two groups on the phenyl ring selected from the group consisting of lower alkyl of 1 to 4 carbons, lower alkoxy of 1 to 4 carbons, lower alkylthio of 1 to 4 carbons, chloro, bromo, fluoro, iodo, trifluoromethyl, acetyloxy, and hydroxy;
R$_2$ and R$_3$ are independently selected from hydrogen, lower alkyl and trifluoromethyl;

R$_4$ is hydrogen, $$R_5-\overset{O}{\underset{\|}{C}}- \text{ or } -S-(CH)_n-\underset{\underset{R_3}{|}}{CH}-\underset{\underset{R_2}{|}}{CH}-CO-N\underset{\underset{H}{|}}{\overset{H_2C}{\diagup}}\overset{4}{\underset{3}{\diagdown}}\underset{C_*-COOR}{\overset{X-R_1}{|}}$$

R$_5$ is lower alkyl, phenyl, phenyl-lower alkylene, substituted phenyl, or substituted phenyl-lower alkylene wherein said substituent is one or two groups on the phenyl ring selected from the group consisting of lower alkyl of 1 to 4 carbons, lower alkoxy of 1 to 4 carbons, lower alkylthio of 1 to 4 carbons, chloro, bromo, fluoro, iodo, trifluoromethyl, acetyloxy, and hydroxy; and
n is 0, 1 or 2.

2. A compound of claim 1 wherein X is oxygen.
3. A compound of claim 1 wherein X is sulfur.
4. A compound of claim 1 wherein R$_4$ is hydrogen.
5. A compound of claim 1 wherein the proline ring is in the L-configuration.
6. A compound of the formula $$R_4-S-(CH_2)_n-\underset{\underset{R_2}{|}}{CH}-CO-N\underset{\underset{H}{|}}{\overset{H_2C}{\diagup}}\overset{4}{\underset{3}{\diagdown}}\underset{C_*-COOH}{\overset{O-R_1}{|}}$$

or a basic salt thereof wherein
the O—R$_1$ group is located at the 3- or 4- position of the proline ring;
R$_1$ is lower alkyl of 1 to 4 carbons, $$-(CH_2)_p-\underset{R_6}{\underset{|}{\bigcirc}}, \quad \underset{R_6}{\underset{|}{\bigcirc}}-\underset{R_6'}{\underset{|}{\bigcirc}},$$

or 1- or 2-naphthyl of the formula $$\underset{R_6}{\underset{|}{\overset{1}{\underset{2}{\bigcirc}}}}\underset{R_6'}{\underset{|}{\bigcirc}};$$

R$_2$ is hydrogen, methyl, or trifluoromethyl;
R$_4$ is hydrogen, acetyl, or benzoyl;
R$_6$ and R$_6'$ are independently selected from the group consisting of hydrogen, methyl, methoxy, methylthio, chloro, fluoro, trifluoromethyl and hydroxy provided that only one of R$_6$ and R$_6'$ is other than hydrogen;
n is zero or one; and
p is zero, one or two.

7. A compound of claim 6 of the formula

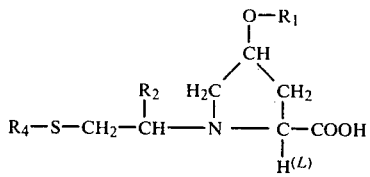

or a basic salt thereof wherein $R_2$ is hydrogen or methyl and when $R_2$ is methyl the asymmetric carbon to which $R_2$ is attached is in the D-configuration, and $R_1$ and $R_4$ are as defined in claim 6.

8. A compound of claim 7 wherein $R_2$ is methyl and the O—$R_1$ group is in the cis configuration.
9. A compound of claim 8 wherein $R_1$ is lower alkyl of 1 to 4 carbons.
10. A compound of claim 9 wherein $R_4$ is hydrogen.
11. A compound of claim 9 wherein $R_4$ is acetyl.
12. The compound of claim 10 wherein $R_1$ is methyl.
13. The compound of claim 10 wherein $R_1$ is t-butyl.
14. The compound of claim 7, (trans)-4-methoxy-1-(D-3-mercapto-2-methyl-1-oxopropyl)-L-proline.
15. The compound of claim 7, (trans)-4-methoxy-1-(3-mercapto-1-oxopropyl)-L-proline.
16. The compound of claim 7, (trans)-4-ethoxy-1-(D-3-mercapto-2methyl-1-oxopropyl)-L-proline.
17. The compound of claim 7, (trans)-4-propoxy-1-(D-3-mercapto-2-methyl-1-oxopropyl)-L-proline.
18. A compound of claim 8 wherein $R_1$ is

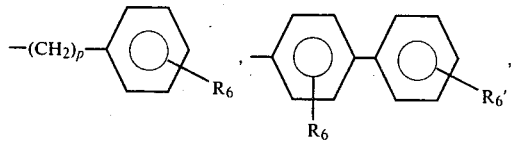

or a 1- or 2-naphthyl group of the formula

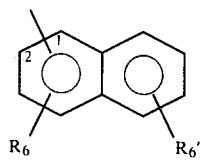

19. A compound of claim 18 wherein $R_4$ is hydrogen.
20. A compound of claim 18 wherein $R_4$ is acetyl.
21. A compound of claim 18 wherein $R_4$ is benzoyl.
22. The compound of claim 19 wherein $R_1$ is

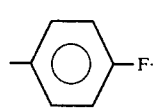

23. The compound of claim 19 wherein $R_1$ is

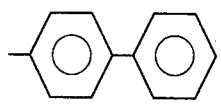

24. The compound of claim 19 wherein $R_1$ is

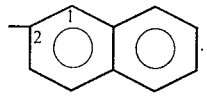

25. The compound of claim 6, (cis) -1-(3-mercapto-2-methyl-1-oxopropyl)-3-phenoxy-D,L-proline.
26. A compound of the formula

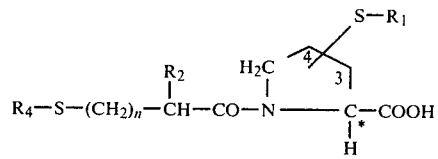

or a basic salt thereof wherein
the S—$R_1$ group is located at the 3- or 4-position of the proline ring;
$R_1$ is lower alkyl of 1 to 4 carbons,

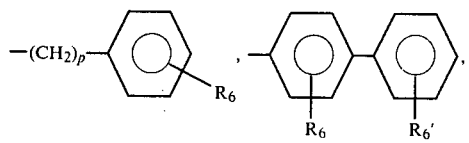

or 1- or 2-naphthyl of the formula

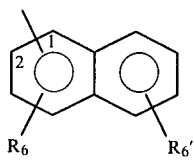

$R_2$ is hydrogen, methyl, or trifluoromethyl;
$R_4$ is hydrogen, acetyl, or benzoyl;
$R_6$ and $R_6'$ are independently selected from the group consisting of hydrogen, methyl, methoxy, methylthio, chloro, fluoro, trifluoromethyl and hydroxy provided that only one of $R_6$ and $R_6'$ is other than hydrogen;
n is zero or one; and
p is zero, one or two.

27. A compound of claim 26 of the formula

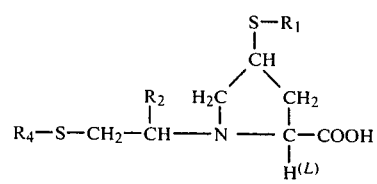

or a basic salt thereof wherein $R_2$ is hydrogen or methyl and when $R_2$ is methyl the asymmetric carbon to which $R_2$ is attached is in the D-configuration, and $R_1$ and $R_4$ are as defined in claim 26.

28. A compound of claim 27 wherein $R_2$ is methyl and the —S—$R_1$ group is in the cis configuration.
29. A compound of claim 28 wherein $R_1$ is lower alkyl of 1 to 4 carbons.
30. A compound of claim 28 wherein $R_1$ is

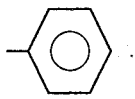

31. The compound of claim 30 wherein $R_4$ is hydrogen.
32. The compound of claim 30 wherein $R_4$ is acetyl.
33. The compound of claim 30 wherein $R_4$ is benzoyl.
34. A compound of claim 28 wherein $R_1$ is

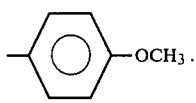

35. The compound of claim 34 wherein $R_4$ is hydrogen.
36. A compound of claim 28 wherein $R_1$ is

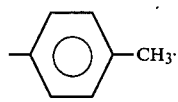

37. The compound of claim 36 wherein $R_4$ is hydrogen.
38. A compound of claim 28 wherein $R_1$ is

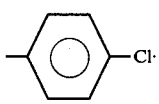

39. The compound of claim 38 wherein $R_4$ is hydrogen.
40. A compound of claim 28 wherein $R_1$ is

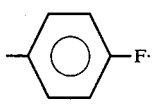

41. The compound of claim 40 wherein $R_4$ is hydrogen.
42. A compound of claim 28 wherein $R_1$ is

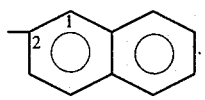

43. The compound of claim 42 wherein $R_4$ is hydrogen.
44. The compound of claim 26 (trans)-1-(3-mercapto-1-oxopropyl)-3-(methylthio)-D,L-proline.
45. A compound of claim 1 wherein $R_4$ is

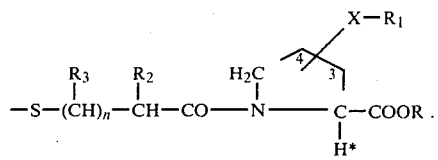

46. The compound of claim 45, 1,1'-[dithiodi-(1-D-3-mercapto-2-methyl-1-oxopropyl)]bis[(cis)-4-(phenylthio)-L-proline].
47. The potassium salt of the compound of claim 46.
48. The compound of claim 2, (cis)-4-(cyclohexyloxy)-1-(D-3-mercapto-2-methyl-1-oxopropyl)-L-proline.
49. The compound of claim 3, (cis)-1-(D-3-mercapto-2-methyl-1-oxopropyl)-4-(phenylthio)-L-proline, ethyl ester.
50. A compound of the formula

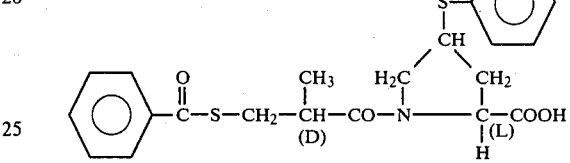

or a physiologically acceptable salt thereof.
51. The compound of claim 50 wherein the

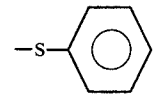

group is in the cis configuration.
52. The L-arginine salt of the compound of claim 51.
53. The sodium salt of the compound of claim 51.
54. The potassium salt of the compound of claim 51.
55. The magnesium salt of the compound of claim 51.
56. The calcium salt of the compound of claim 51.
57. A compound of the formula

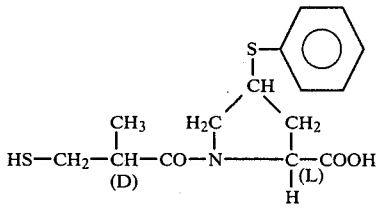

or a physiologically acceptable salt thereof.
58. The compound of claim 57 wherein the

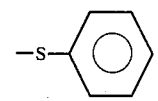

group is in the cis configuration.
59. The L-arginine salt of the compound of claim 58.
60. A composition useful in the treatment of hypertension comprising an effective amount of a compound of claim 1 including a physiologically acceptable salt thereof and a pharmaceutically acceptable carrier therefor.
61. A method for reducing blood pressure in hypertensive mammals which comprises administering an effective amount of the composition of claim 60.

* * * * *